United States Patent
Cropp et al.

(10) Patent No.: US 10,472,424 B2
(45) Date of Patent: Nov. 12, 2019

(54) TREATMENT WITH ANTI-PCSK9 ANTIBODIES

(71) Applicant: PFIZER INC., New York, NY (US)

(72) Inventors: Anne Barbara Cropp, Madison, CT (US); Albert Kim, Newton, MA (US); David Raymond Plowchalk, Waterford, CT (US); Kevin Richard Sweeney, East Lyme, CT (US); Ellen Qiao Wang, Brooklyn, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/510,600

(22) PCT Filed: Sep. 9, 2015

(86) PCT No.: PCT/IB2015/056906
§ 371 (c)(1),
(2) Date: Mar. 10, 2017

(87) PCT Pub. No.: WO2016/046684
PCT Pub. Date: Mar. 31, 2016

(65) Prior Publication Data
US 2017/0306051 A1  Oct. 26, 2017

Related U.S. Application Data

(60) Provisional application No. 62/054,226, filed on Sep. 23, 2014, provisional application No. 62/093,885, filed on Dec. 18, 2014.

(51) Int. Cl.
| | | |
|---|---|---|
| *A61K 39/395* | (2006.01) | |
| *C07K 16/40* | (2006.01) | |
| *A61K 31/351* | (2006.01) | |
| *A61K 31/40* | (2006.01) | |
| *A61K 31/505* | (2006.01) | |
| *A61K 45/06* | (2006.01) | |
| *A61K 39/00* | (2006.01) | |

(52) U.S. Cl.
CPC ............ *C07K 16/40* (2013.01); *A61K 31/351* (2013.01); *A61K 31/40* (2013.01); *A61K 31/505* (2013.01); *A61K 39/3955* (2013.01); *A61K 45/06* (2013.01); *A61K 2039/505* (2013.01); *A61K 2039/54* (2013.01); *A61K 2039/545* (2013.01); *C07K 2317/24* (2013.01); *C07K 2317/565* (2013.01); *C07K 2317/76* (2013.01)

(58) Field of Classification Search
CPC .................................................... C07K 16/40
See application file for complete search history.

(56) References Cited

U.S. PATENT DOCUMENTS

| | | |
|---|---|---|
| 8,030,457 B2 | 10/2011 | Jackson et al. |
| 8,062,640 B2 | 11/2011 | Sleeman et al. |
| 8,080,243 B2 | 12/2011 | Liang et al. |
| 8,188,234 B2 | 5/2012 | Condra et al. |
| 8,710,192 B2 * | 4/2014 | Rue .................. C07K 16/40 530/388.26 |
| 2010/0029513 A1 | 2/2010 | Myerson et al. |
| 2010/0068199 A1 | 3/2010 | Liang et al. |
| 2013/0064834 A1 | 3/2013 | Sleeman et al. |
| 2014/0161821 A1 | 6/2014 | Udata |

FOREIGN PATENT DOCUMENTS

| | | |
|---|---|---|
| EP | 2706070 | 3/2014 |
| WO | 2010029513 | 3/2010 |
| WO | 20120101251 | 8/2012 |
| WO | 2013008185 | 1/2013 |
| WO | 20150142668 | 9/2015 |

OTHER PUBLICATIONS

Ballantyne et al., ACC Abstract; ACC.14 63rd Annual Scientific Session & Expo; Mar. 29-31, 2014 Washington D.C.; 2 pages.
Ballantyne et al.; Poster: Efficacy and Safety of Bococizumab (RN316/PF-04950615), a Monoclonal Antibody Against Proprotein Convertase Subtilisin/Kexin Type 9, in Statin-Treated hypercholesterolemic Subjects: Results from a Randomized, Placebo-Controlled, Dose-Ranging Study (NCT: 01592240); ACC 63rd Annual Scientific Session; Mar. 29-31, 2014 Washington D.C.; 1 page.
Ballantyne et al., Poster: Bococizumab (RN316/PF-04950615), a monoclonal Antibody Against PCsK9, in Stalin-Treated Hypercholesterolemic subjects: Results from a Randomized, Placebo-Controlled, Dose-Ranging study (NCT: 01592240); 82nd European Atherosclerosis Society (EAS) Congress, May 31-Jun. 3, 2014; Madrid, Spain; 1 page.
Wang et al., Poster: Population Pharmacokinetic and Pharmacodynamic Modeling of Bococizumab (RN316/PF-04950615) in Hypercholesterolemic Subjects; 82nd European Atherosclerosis Society (EAS) Congress, May 31-Jun. 3, 2014; Madrid, Spain; 1 page.
Abifadel et al. "Mutations in PCSK9 cause autosomal dominant hypercholesterolemia" Nature Genetics; vol. 34; No. 2; pp. 154-156; 2003.

(Continued)

*Primary Examiner* — Albert M Navarro

(57) ABSTRACT

The present invention relates to therapeutic dosing regimens utilizing a dose reduction strategy for treating disorders characterized by marked elevations of low density protein cholesterol (LDL-C) in the plasma of a patient. The subject therapeutic dosing regimens involve delivering as a single administration or plurality of administrations of an anti-proprotein convertase subtilisin kexin type 9 (PCSK9) antagonist antibody as an initial dose of at least about 100 mg, and delivering as a single administration or plurality of administrations at a subsequent dose in an amount that is about the same as the initial dose, or at least half the initial dose after the patient has a LDL-C level at or below about 25, 20, 15 or 10 mg/dL, preferably at or below 10 mg/dL.

19 Claims, 8 Drawing Sheets

Specification includes a Sequence Listing.

(56) References Cited

OTHER PUBLICATIONS

Bangalore et al, "Visit-to-visit variability in low density lipoprotein-cholesterol and risk of cardiovascular outcomes: insights from the treating to new targets trial" Eur. Heart J.; 33(Suppl 1):958 abstract 5243; 2012.
Benn et al. "PCSK9 R46L, Low-Density Lipoprotein Cholesterol Levels, and Risk of Ischemic Heart Disease" Journal of the American College of Cardiology; vol. 55, No. 5, pp. 2833-2842; 2010.
Brautbar and Ballantyne; "Pharmacological strategies for lowering LDL cholesterol: statins and beyond" Nature Reviews Cardiology; vol. 8, pp. 253-265; 2011.
Cohen et al. "Low LDL cholesterol in individuals of African descent resulting from frequent nonsense mutations in PCSK9" Nature Genetics; vol. 37, No. 2; pp. 161-165; 2005.
Cohen et al. "Sequence Variations in PCSK9, Low LDL, and Protection against Coronary Heart Disease" N.E. J. o f Medicine; vol. 354; pp. 1264-1272; 2006.
Dadu and Ballantyne; "Lipid lowering with PCSK9 inhibitors" Nature Reviews Cardiology; vol. 11; pp. 563-575; 2014.
Davignon et al. "The Influence of PCSK9 Polymorphisms on Serum Low-Density Lipoprotein Cholesterol and Risk of Atherosclerosis" Curr. Atheroscler. Rep.; vol. 12; pp. 305-315; 2010.
Giugliano et al. "Efficacy, safety, and tolerability of a monoclonal antibody to proprotein convertase subtilisin/kexin type 9 in combination with a statin in patients with hypercholesterolaemia (LAPLACE-TIMI 57): a randomised, placebo-controlled, dose-ranging, phase 2 study" Lancet; vol. 380; pp. 2007-2017; 2012.
Hirayama et al. "Effects of Evolocumab (AMG 145), a Monoclonal Antibody to PCsK9, in Hypercholesterolemic, Statin-Treated Japanese Patients at High Cardiovascular Risk" Circulation Journal; vol. 78; No. 5; pp. 1074-1782; 2014.
Hooper et al. "The C679X mutation in PCSK9 is present and lowers blood cholesterol in a Southern African population" Atherosclerosis; vol. 193; pp. 445-448; 2007.
Horton et al. "PCSK9: a convertase that coordinates LDL catabolism" Journal of Lipid Research; vol. 50; pp. S172-S177; 2009.
Koren et al. "Efficacy, safety, and tolerability of a monoclonal antibody to proprotein convertase subtilisin/kexin type 9 as monotherapy in patients with hypercholesterolaemia (MENDEL): a randomised, double-blind, placebo-controlled, phase 2 study" Lancet; vol. 380; pp. 1995-2006; 2012.
Koren et al. "Anti-PCSK9 Monotherapy for Hypercholesterolemia The MENDEL-2 Randomized, Controlled Phase III Clinical Trial of Evolocumab" J. of the American College of Cardiology; vol. 63; No. 23; pp. 2531-2540; 2014.
Lambert et al. "Thematic Review Series: New Lipid and Lipoprotein Targets for the Treatment of Cardiometabolic Diseases the PCSK9 decade" Journal of Lipid Research; vol. 53; pp. 2515-2524; 2012.
LaRosa et al. "Safety and Effect of Very Low Levels of Low-Density Lipoprotein Cholesterol on Cardiovascular Events" Amer. J. Cardiol.; vol. 111; pp. 1221-1229; 2013.
Lo Surdo et al. "Mechanistic implications for LDLreceptor degradation from the PCSK9/LDLR structure at neutral pH" EMBO Reports; vol. 12; No. 12; pp. 1300-1305; 2011.
Piper et al. "The Crystal Structure of PCSK9: A Regulator of Plasma LDL-Cholesterol" Structure; vol. 15; pp. 545-552; 2007.
Seidah et al. "The secretory proprotein convertase neural apoptosis-regulated convertase 1 (NARC-1): Liver regeneration and neuronal differentiation" PNAS; vol. 100; No. 3; pp. 928-933; 2003.
Seidah and Prat "The biology and therapeutic targeting of the proprotein convertases" Nature Reviews Drug Discovery; vol. 11; pp. 367-383; 2012.
Stein et al. "Effect of a monoclonal antibody to PCSK9, REGN727/SAR236553, to reduce low-density lipoprotein cholesterol in patients with heterozygous familial hypercholesterolaemia on stable statin dose with or without ezetimibe therapy: a phase 2 randomised controlled trial" LANCET; vol. 380; pp. 29-36; 2012.
Stroes et al. "Anti-PCSK9 Antibody Effectively Lowers Cholesterol in Patients With Statin Intolerance The GAUSS-2 Randomized, Placebo-Controlled Phase 3 Clinical Trial of Evolocumab" Journal of the American College of Cardiology vol. 63; No. 23; pp. 2541-2548; 2014.
Sullivan et al. "Effect of a Monoclonal Antibody to PCSK9 on Low Density Lipoprotein Cholesterol Levels in Statin-Intolerant Patients" J. American Medical Association; vol. 308; No. 23; pp. 2497; 2012.
Tibolla et al. "Proprotein convertase subtilisin/kexin type 9 (PCSK9): From structure-function relation to therapeutic inhibition" Nutrition, Metabolism & Cardiovascular Diseases; vol. 21; pp. 835-843; 2011.
Zhao et al. "Molecular Characterization of Loss-of-Function Mutations in PCSK9 and Identification of a Compound Heterozygote" American J. of Human Genetics; vol. 79; pp. 514-523; 2006.
McKenney et al. "Safety and Efficacy of a Monoclonal Antibody to Proprotein Convertase Subtilisin/Kexin Type 9 Serine Protease, SAR236553/REGN727, in Patients With Primary Hypercholesterolemia Receiving Ongoing Stable Atorvastatin Therapy" J. of the American College of Cardiology; vol. 59; No. 25; pp. 2344-2353; 2012.
International Search Report and Written Opinion; PCT/IB2015/056906; dated Feb. 9, 2016; 15 pages.
Moriarty et al: "Efficacy and safety of alirocumab, a monoclonal antibody to PC5K9, in statin-intolerant patients: Design and rationale of Odyssey Alternative, a randomized phase 3 trial", J. of Clinical Lipidology, vol. 8, No. 6, Nov. 1, 2014, pp. 554-561.

* cited by examiner

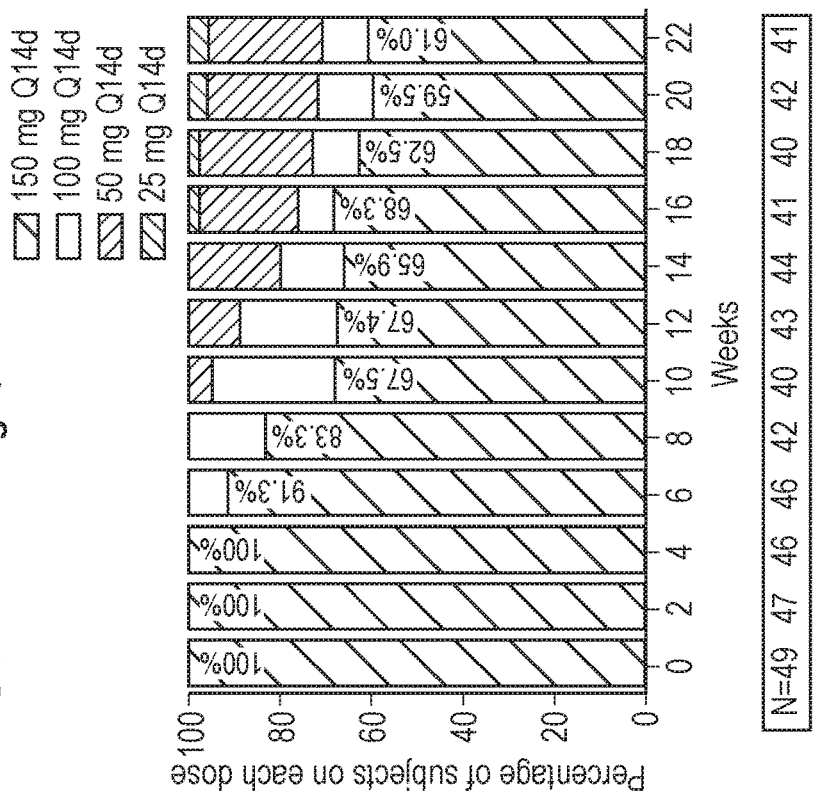
FIG. 2A 100 mg Q14d
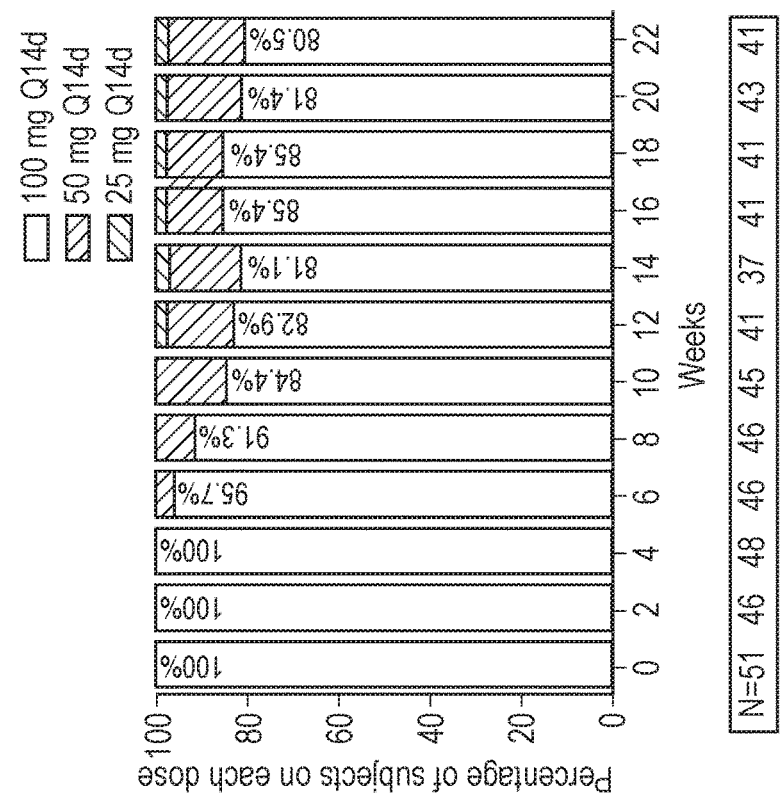
FIG. 2B 150 mg Q14d

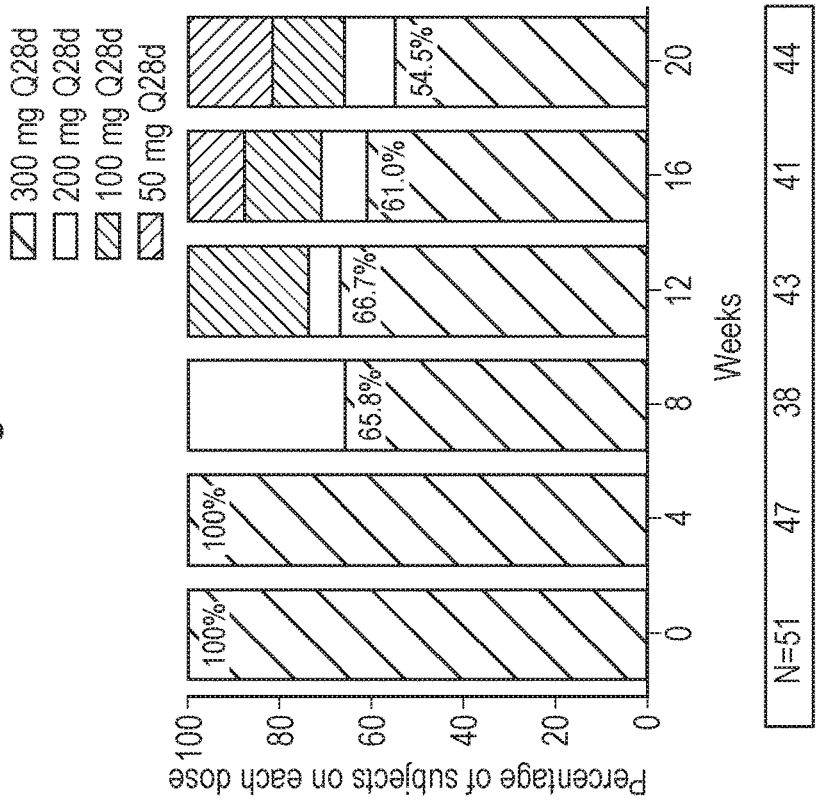
FIG. 2D 300 mg Q28d
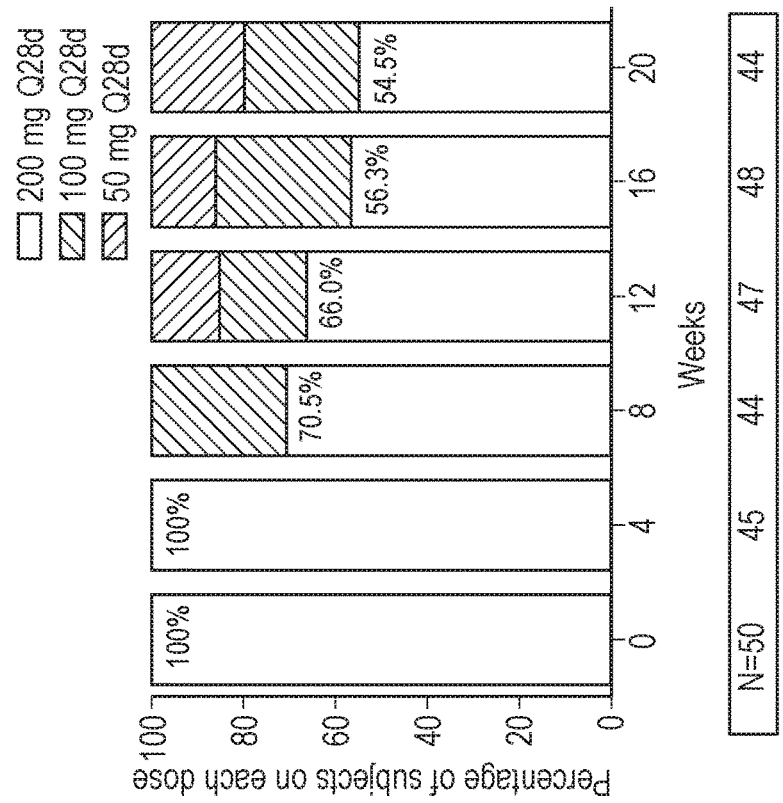
FIG. 2C 200 mg Q28d

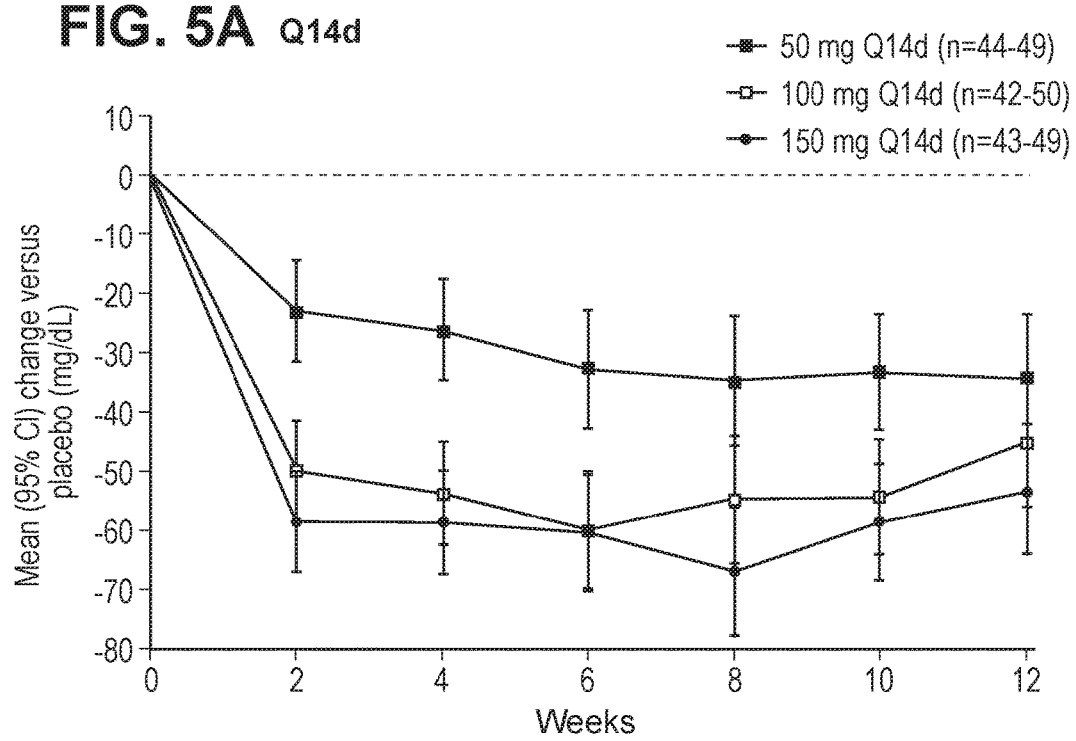
FIG. 5A Q14d
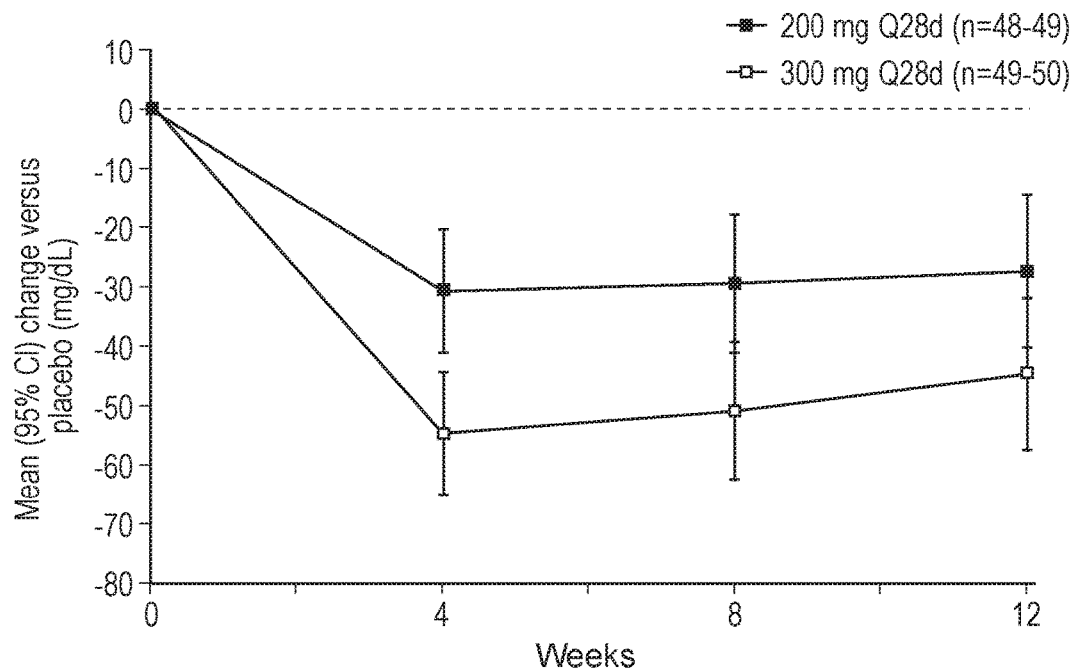
FIG. 5B Q28d

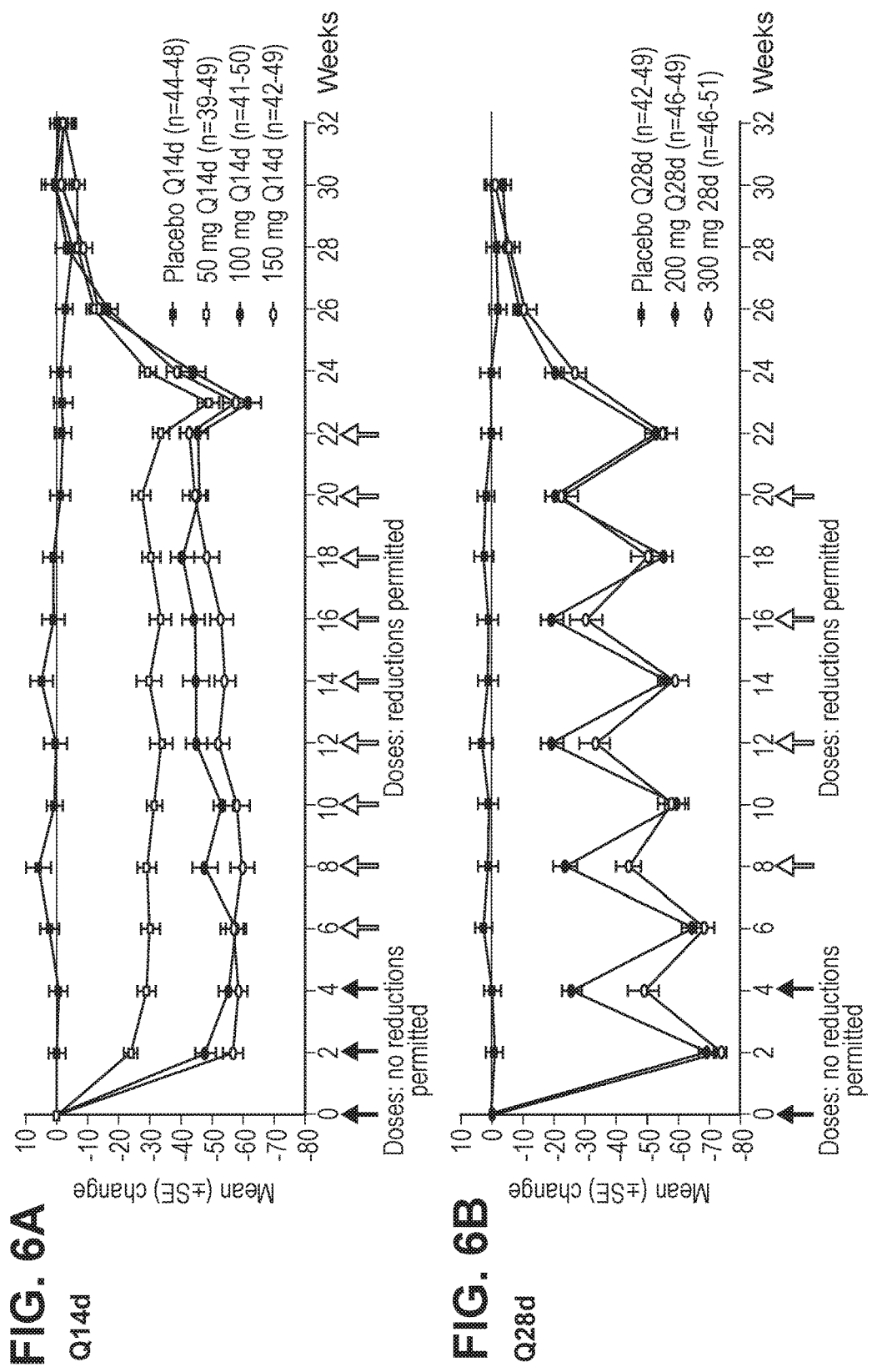

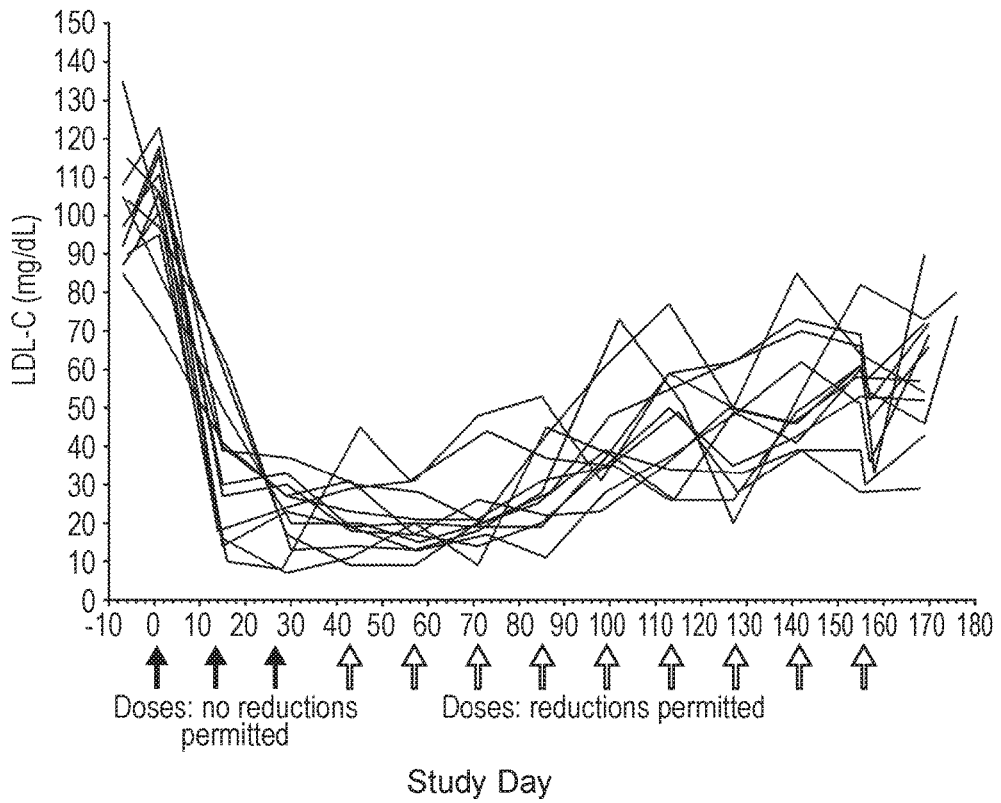

TREATMENT WITH ANTI-PCSK9 ANTIBODIES

CROSS-REFERENCE TO RELATED APPLICATIONS

This application is a 071 filing of PCT/IB2015/056906 filed Sep. 9, 2015, which claims the benefit of U.S. Provisional Application No. 62/054,226 filed Sep. 23, 2014, and U.S. Provisional Application No. 62/093,885 filed Dec. 18, 2014, both of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC72162A_SeqListing_ST25.txt" created on Mar. 9, 2017, and having a size of 42 KB. The sequence listing contained in this .txt file is part of the specification and is incorporated herein by reference in its entirety.

FIELD

The present invention relates to therapeutic dosing regimens utilizing a dose reduction strategy for reducing LDL-cholesterol levels in a patient using a therapeutically effective amount of a proprotein convertase subtilisin kexin type 9 (PCSK9) antagonist antibody which specifically binds to a human PCSK9 protein. The subject treatment can be used in the treatment of cholesterol and lipoprotein metabolism disorders, including hypercholesterolemia, dyslipidemia, hyperlipidemia, atherosclerosis, acute coronary syndrome and, more generally, cardiovascular disease (CVD).

BACKGROUND

Proprotein convertase subtilisin/kexin type 9 (PCSK9) has recently become recognized as a key player in regulating cholesterol metabolism and has emerged as a promising target for prevention and treatment of coronary heart disease (CHD) (see, e.g., Seidah et al., Proc. Natl. Acad. Sci. U.S.A 100:928-33, 2003). Gain-of-function (GOF) mutations in PCSK9 have been found to be associated with autosomal dominant hypercholesterolaemia (ADH) (see, e.g., Abifadel et al., Nat. Genet. 34:154-6, 2003), mild to severe hypercholesterolaemia, and an increased risk of CHD (see, e.g., Davignon et al., Curr. Atheroscler. Rep. 12:308-15, 2010). Conversely, the loss-of-function (LOF) mutations in PCSK9 are associated with lifelong reductions in low-density lipoprotein cholesterol (LDL-C) (see, e.g., Cohen et al., Nat. Genet. 37:161-5, 2005; and Tibolla et al., Nutr. Metab. Cardiovasc. Dis. 21:835-43, 2011). Further, the LOF mutations in PCSK9 have been found to reduce the atherosclerosis and CHD risk (see, e.g., Cohen et al., N Eng J Med 354: 1264-72, 2010; Benn et al., J Am Coll Cardiol 55:2833-42, 2010); whereas the complete loss of PCSK9 results in low serum LDL-C of <20 mg/dl in human health subjects (Hooper et al., Atheroscler. 193:445-8, 2007; and Zhao et al., Am. J. Hum. Genet. 79: 514-23, 2006).

The main way by which PCSK9 regulates LDL-C levels is modulating the degradation of the LDL receptor (LDLR) by direct interaction with the LDLR both within the cell and at the surface of the plasma membrane (see, e.g., Seidah et al., Nat. Rev. Drug. Discov. 11:367-83, 2012; and Lambert et al., J. Lipid. Res. 53:2515-24, 2012). Highly expressed in the liver and intestine, PCSK9 is secreted after the autocatalytic cleavage of the prodomain and can bind to the LDLR in a complex, which triggers modification of LDLR conformation, avoiding the normal recycling of LDLR to the plasma membrane, and increasing LDLR lysosomal degradation (see e.g., Horton et al, J. Lipid. Res. 50:S172-S177, 2009; Piper et al., Structure 15:545-52, 2007; and Lo Surdo et al., EMBO Rep. 12:1300-5, 2011).

Various therapeutic approaches for inhibiting PCSK9 are currently in development, including gene silencing by siRNA or anti-sense oligonucleotides and disruption of the PCSK9-LDLR interaction by antibodies. Brautbar et al., Nature Reviews Cardiology 8, 253-265, 2011. Further, various PCSK9 antagonist antibodies have also been reported for the treatment of serum cholesterol reduction as well as primary and secondary atherosclerotic cardiovascular disease (ASCVD). See, e.g., U.S. Pat. Nos. 8,080,243, 8,030,457, 8,062,640, and US20140161821.

While the lower levels of LDL-C achievable with currently available lipid-lowering therapies do not appear to be harmful (see, e.g., LaRosa et al., Am. J. Cardiol. 111:1221-1229, 2013), the safety of very low levels of LDL-C achievable with PCSK9 inhibitors, particularly when sustained over a prolonged period, is unclear (see LaRosa, supra., and Dadu et al., Nat. Rev. Cardiol. Doi:10.1038/nrcardio.2014.84, 2014). Previous epidemiological studies and data from earlier statin trials suggested an association between lower levels of LDL-C and increased risk of cancer, hemorrhagic stroke, and non-cardiac death: an association that has not been supported by subsequent outcome studies and large meta-analyses (see, e.g., La Rosa et al., supra; and Dadu et al., supra). Concerns have also been raised regarding possible cognitive symptoms associated with very low LDL-C levels. (See, e.g., Dadu et al., supra). Accordingly, it remains unclear what are the lower doses of PCSK9 antagonist antibody that would still be considered effective and efficacious to treat LDL-C related disorders in patients while preventing extremely low levels of LDL-C.

SUMMARY

The present invention relates to therapeutic dosing regimens utilizing a dose reduction strategy for treating disorders characterized by marked elevations of low density protein cholesterol (LDL-C) in the plasma of a patient. The subject therapeutic dosing regimens involve delivering as a single administration or plurality administrations of an anti-proprotein convertase subtilisin kexin type 9 (PCSK9) antagonist antibody as an initial dose of at least about 100 mg, and delivered as a single administration or plurality of administrations at a subsequent dose in an amount that is about the same as the initial dose, or at least half the initial dose after the patient has a LDL-C level at or below about 25, 20, 15, or 10 mg/dL, preferably lower than about 10 mg/dL.

Accordingly, in one aspect, this invention provides a PCSK9 antagonist antibody for use in the treatment of a disorder in a patient characterized by an elevated low-density lipoprotein cholesterol (LDL-C) level in the blood, wherein the PCSK9 antagonist antibody is delivered as a single administration or plurality of administrations at an initial dose of at least about 100 mg, and delivered as a single administration or plurality of administrations at a subsequent dose in an amount that is about the same as the initial dose, or at least half the initial dose after the patient has a LDL-C level at or below about 25, 20, 15, or 10 mg/dL, preferably lower than about 10 mg/dL, wherein all administrations are separated in time from each other by at least about two weeks.

In another aspect, this invention provides a method for treating a patient susceptible to or diagnosed with a disorder characterized by an elevated low-density lipoprotein cholesterol (LDL-C) level in the blood, comprising: delivering to the patient as a single administration or plurality of administrations an initial dose of at least about 100 mg of a PCSK9 antagonist antibody; and delivering to the patient a single administration or plurality of administrations at a subsequent dose that is about the same as the initial dose, or at least half the initial dose after the patient has a LDL-C level at or below about 25, 20, 15, or 10 mg/dL, preferably at or below about 10 mg/dL, wherein all administrations are separated in time from each other by at least about two weeks.

In another aspect, this invention provides a use of a single administration or plurality of administrations an initial dose of at least about 100 mg of a PCSK9 antagonist antibody, in the manufacture of a medicament for treating a patient susceptible to or diagnosed with a disorder characterized by an elevated low-density lipoprotein cholesterol (LDL-C) level in the blood, wherein a single administration or plurality of administrations at a subsequent dose is about the same as the initial dose, or at least half the initial dose after the patient has a LDL-C level at or below about 25, 20, 15, or 10 mg/dL, preferably at or below about 10 mg/dL, and wherein all administrations are separated in time from each other by at least about two weeks.

In another aspect, provided is an article of manufacture, comprising a container, a composition within the container comprising a PCSK9 antagonist antibody, and a package insert containing instructions to deliver as a single administration or plurality of administrations at an initial dose of PCSK9 antagonist antibody of at least about 100 mg, and delivered as a single administration or plurality of administrations at a subsequent dose in an amount that is about the same as the initial dose, or at least half the initial dose after the patient has a LDL-C level at or below about 25, 20, 15, or 10 mg/dL, preferably at or below about 10 mg/dL, wherein all administrations are separated in time from each other by at least about two weeks.

In some embodiments, the subsequent dose is about two thirds of the initial dose; in other embodiments, the subsequent dose is about one half the initial dose.

In some embodiments, the initial dose is 150 mg, and the subsequent dose is 150 mg every two weeks after the patient has a LDL-C level above about 25, 20, 15 or 10 mg/dL, preferably above about 10 mg/dL.

In some embodiments, the initial dose is 150 mg, and the subsequent dose is reduced below 150 mg every two weeks after the patient has a LDL-C level below about 25, 20, 15 or 10 mg/dL.

In some embodiments, the initial dose is 150 mg, and the subsequent dose is reduced to 75 mg after the patient has a LDL-C at or below about 25, 20, 15 or 10 mg/dL, preferably at or below about 10 mg/dL.

In some embodiments, the initial dose is 150 mg, and the subsequent dose is 100 mg after the patient has a LDL-C at or below about 25, 20, 15 or 10 mg/dL, preferably at or below about 10 mg/dL.

In some embodiments, the subsequent dose is administered to the patient after the patient has at least about two consecutive assessments of LDL-C at or below about 25, 20, 15 or 10 mg/dL, preferably at or below about 10 mg/dL.

In some embodiments, following an initial dose of at least about 100 mg, the subsequent dose is reduced to half the initial dose and is administered every two weeks after the patient has a LDL-C at or below 25, 20, 15 or 10 mg/dL, preferably at or below about 10 mg/dL, and a second subsequent dose is administered every two weeks and is even further reduced to one third or one quarter the initial dose, delivered as a single or plurality of administrations, after the patient has a LDL-C again at or below about 25, 20, 15 or 10 mg/dL, preferably at or below about 10 mg/dL, while on the subsequent dose.

In some embodiments, following an initial dose of at least about 100 mg, the subsequent dose is reduced to two thirds the initial dose and is administered every two weeks after the patient has a LDL-C at or below 25, 20, 15 or 10 mg/dL, preferably at or below about 10 mg/dL, and a second subsequent dose is administered every two weeks and is then even further reduced to one third or one quarter the initial dose, delivered as a single or plurality of administrations, after the patient had a LDL-C again at or below about 25, 20, 15 or 10 mg/dL, preferably at or below about 10 mg/dL, while on the subsequent dose.

In some embodiments, following an initial dose of at least about 100 mg, the subsequent dose is reduced to half the initial dose and is administered every two weeks after the patient has a LDL-C at or below 25, 20, 15 or 10 mg/dL, preferably at or below about 10 mg/dL, and the subsequent dose is then administered every four weeks after the patient has a LDL-C again at or below 25, 20, 15 or 10 mg/dL, preferably at or below about 10 mg/dL, while on the subsequent dose every two weeks.

In some embodiments, the initial dose is 150 mg and the subsequent dose is 75 mg. In some embodiments, following an initial dose of about 150 mg, the subsequent dose is reduced to 75 mg and is administered every two weeks after the patient has a LDL-C at or below 25, 20, 15 or 10 mg/dL, preferably at or below about 10 mg/dL, and the subsequent dose of 75 mg is then administered every four weeks after the patient has a LDL-C again at or below 25, 20, 15 or 10 mg/dL, preferably at or below about 10 mg/dL, while on the subsequent dose every two weeks. In some embodiments, following an initial dose of about 150 mg, the subsequent dose is reduced to 75 mg and is administered every two weeks after the patient has at least about two consecutive assessments of LDL-C level at or below 25, 20, 15 or 10 mg/dL, preferably at or below about 10 mg/dL, and said subsequent dose is then administered every four weeks after the patient has at least about another two consecutive assessments of LDL-C level again at or below 25, 20, 15 or 10 mg/dL, preferably at or below about 10 mg/dL, while on the subsequent dose every two weeks.

In one variation, the present invention provides a method of treatment of a disorder in a patient characterized by an elevated low-density lipoprotein cholesterol (LDL-C) level in the blood, comprising administering to the patient a proprotein convertase subtilisin kexin type 9 (PCSK9) antagonist antibody in a dosage regimen comprising an initial dose followed by one or more subsequent doses, characterized in that if the patient presents with an ophthalmic pathology during the dosage regimen, the amount of PCSK9 antagonist antibody in subsequent doses following the presentation of the ophthalmic pathology is reduced relative to the dose prior to the presentation of the ophthalmic pathology.

In another aspect, provided is a method of treatment of a disorder in a patient characterized by an elevated low-density lipoprotein cholesterol (LDL-C) level in the blood, comprising administering to the patient a proprotein convertase subtilisin kexin type 9 (PCSK9) antagonist antibody in a dosage regimen comprising an initial dose followed by one or more subsequent doses, and wherein all administrations are separated in time from each other by at least about two weeks, characterized in that if the patient presents with an ophthalmic pathology during the dosage regimen, the subsequent administration of PCSK9 antagonist antibody following the presentation of the ophthalmic pathology is separated in time from the preceding administration of PCSK9 antagonist antibody by at least one additional week.

In another aspect, provided is a method of treatment of a disorder in a patient characterized by an elevated low-density lipoprotein cholesterol (LDL-C) level in the blood, comprising administering to the patient a proprotein convertase subtilisin kexin type 9 (PCSK9) antagonist antibody in a dosage regimen comprising an initial dose followed by one or more subsequent doses, characterized in that the patient does not present with an ophthalmic pathology at the time of the initial administration.

In another aspect, provided is a method of treatment of a disorder in a patient characterized by an elevated low-density lipoprotein cholesterol (LDL-C) level in the blood, comprising administering to the patient a proprotein convertase subtilisin kexin type 9 (PCSK9) antagonist antibody in a dosage regimen comprising an initial dose followed by one or more subsequent doses, characterized in that the dosage regimen is altered in the event of the patient developing an ophthalmic pathology.

In another aspect, provided is a method of treatment of a disorder in a patient characterized by an elevated low-density lipoprotein cholesterol (LDL-C) level in the blood, comprising administering to the patient a proprotein convertase subtilisin kexin type 9 (PCSK9) antagonist antibody in a dosage regimen comprising an initial dose followed by one or more subsequent doses, characterized in that the dosage regimen is discontinued in the event of the patient developing an ophthalmic pathology.

In another aspect, provided is a method of treatment of a disorder in a patient characterized by an elevated low-density lipoprotein cholesterol (LDL-C) level in the blood, comprising administering to the patient a proprotein convertase subtilisin kexin type 9 (PCSK9) antagonist antibody in a dosage regimen comprising an initial dose followed by one or more subsequent doses, characterized in that the dosage regimen is postponed in the event of the patient developing an ophthalmic pathology.

In some embodiments, the ophthalmic pathology as described herein is selected from the group consisting of blepharitis, cataract, conjunctivitis, corneal erosion, glaucoma, ocular hyperaemia, vitreous floaters, dry eye, eye hemorrhage, eye pruritus, eyelid pain, trauma, infection, and corneal pathology.

In some embodiments, the ophthalmic pathology is a corneal pathology, and may be selected from the group consisting of corneal infection, corneal erosion, trauma to the cornea, bacterial corneal infection, fungal corneal infection, keratitis, corneal dystrophy, Fuchs' dystrophy, keratoconus, lattice dystrophy, map-dot-fingerprint dystrophy. herpes zoster, swelling of the corneal epithelium, iridocorneal endothelial syndrome, ocular herpes corneal transplant, and laser eye surgery.

In some embodiments, following the presentation of the ophthalmic pathology the amount of PCSK9 antagonist antibody is reduced relative to the dose prior to the presentation of the ophthalmic pathology.

In some embodiments, the subsequent dose prior to the presentation of the ophthalmic pathology is at least about any of 150 mg, 140 mg, 100 mg, 80 mg, or 50 mg every two weeks.

In some embodiments, the dose prior to the presentation of the ophthalmic pathology is at least about 420 mg or 300 mg every four weeks.

In some embodiments, wherein in the event of the patient developing an ophthalmic pathology, one or more subsequent doses are postponed. In some embodiments, wherein subsequent doses are resumed following treatment of the ophthalmic pathology to the satisfaction of the treating physician.

In some embodiments, the subsequent administration of PCSK9 antagonist antibody following the presentation of the ophthalmic pathology is separated in time from the preceding administration of PCSK9 antagonist antibody by at least one, two, or three additional week.

In some embodiments, the subsequent administration of PCSK9 antagonist antibody following the presentation of the ophthalmic pathology is separated in time from the preceding administration of PCSK9 antagonist antibody for the duration of the time to treat the ophthalmic pathology to the satisfaction of the treating physician.

In some embodiments, the dose prior to the presentation of the ophthalmic pathology is selected from the group consisting of at least about 150 mg every two weeks, at least 140 mg every two weeks, at least 300 mg every four weeks, at least 350 mg every four weeks, at least 400 every four weeks, and at least 420 mg every four weeks.

In some embodiments, the dose following the presentation of the ophthalmic pathology is about or less than a value selected from the group consisting of three quarters, a third, one half, one third, and one quarter of the previous dose.

In some embodiments, the dose following the presentation of the ophthalmic pathology is reduced by at least about any of 10%, 20%, 30%, 40%, 50%, or 60%.

In some embodiments, a statin can be administered prior to the initial dose of the PCSK9 antagonist antibody. In some embodiments, a daily dose of a statin is administered. In other embodiments, stable doses of the statin have been administered for at least about two, three, four, five, or six weeks prior to the initial dose of the PCSK9 antagonist antibody. Examples of a statin include atorvastatin, cerivastatin, fluvastatin, lovastatin, mevastatin, pitavastatin, pravastatin, rosuvastatin, simvastatin, or any pharmaceutically acceptable salts, or stereoisomers thereof.

In some embodiments, the PCSK9 antagonist antibody blocks LDLR binding to the PCSK9 antibody of SEQ ID NO: 1. In some embodiments, the PCSK9 antagonist antibody is alirocumab (PRALUENT™), evolocumab (REPATHA™), REGN728, LGT209, RG7652, LY3015014, J16, L1L3 (bococizumab), 31H4, 11F1, 12H11, 8A1, 8A3, 3C4, 300N, or 1D05. In some embodiments, the PCSK9 antagonist antibody is bococizumab, alirocumab (PRALUENT™), or evolocumab (REPATHA™). In some embodiments, the PCSK9 antagonist antibody is a full antagonist of the PCSK9-mediated effect LDL receptor (LDLR) levels as measured in vitro using an LDLR down-regulation assay in Huh7 cells. In some embodiments, the PCSK9 antagonist antibody comprises a heavy chain variable region (VH) comprising complementarity determining region one (CDR1), CDR2, and CDR3 of the amino acid sequence shown in SEQ ID NO: 2; and a light chain variable region (VL) comprising CDR1, CDR2, and CDR3 of the amino acid sequence shown in SEQ ID NO: 3. In some embodiments, the PCSK9 antagonist antibody comprises a VH CDR1 having the amino acid sequence shown in SEQ ID NO: 4, 5, or 6, a VH CDR2 having the amino acid sequence shown in SEQ ID NO:7 or 8, a VH CDR3 having the amino acid sequence shown in SEQ ID NO: 9, a VL CDR1 having the amino acid sequence shown in SEQ ID NO:10, a VL CDR2 having the amino acid sequence shown in SEQ ID NO:11, and a VL CDR3 having the amino acid sequence shown in SEQ ID NO: 12. In some embodiments, the PCSK9 antagonist antibody comprises a light chain having SEQ ID NO: 13 and a heavy chain having SEQ ID NO: 14, with or without the C-terminal lysine of SEQ ID NO: 14.

In some embodiments, the PCSK9 antagonist antibody comprises a heavy chain variable region (VH) comprising complementarity determining region one (CDR1), CDR2, and CDR3 of the amino acid sequence shown in SEQ ID NO: 19; and a light chain variable region (VL) comprising CDR1, CDR2, and CDR3 of the amino acid sequence shown in SEQ ID NO: 20. In some embodiments, the antibody comprises a VH CDR1 having the amino acid sequence shown in SEQ ID NO: 21, a VH CDR2 having the amino acid sequence shown in SEQ ID NO:22, a VH CDR3 having the amino acid sequence shown in SEQ ID NO: 23, or a variant thereof having one or more conservative amino acid substitutions in CDR1, CDR2, and/or CDR3; and a VL CDR1 having the amino acid sequence shown in SEQ ID NO:24, a VL CDR2 having the amino acid sequence shown in SEQ ID NO:25, and a VL CDR3 having the amino acid sequence shown in SEQ ID NO:26, or a variant thereof having one or more conservative amino acid substitutions in CDR1, CDR2, and/or CDR3. In some embodiments, the PCSK9 antagonist antibody comprises a light chain having SEQ ID NO: 18 and a heavy chain having SEQ ID NO: 17.

In some embodiments, the PCSK9 antagonist antibody comprises a heavy chain variable region (VH) comprising complementarity determining region one (CDR1), CDR2, and CDR3 of the amino acid sequence shown in SEQ ID NO: 29; and a light chain variable region (VL) comprising CDR1, CDR2, and CDR3 of the amino acid sequence shown in SEQ ID NO: 30. In some embodiments, the PCSK9 antagonist antibody comprises a VH CDR1 having the amino acid sequence shown in SEQ ID NO: 31, a VH CDR2 having the amino acid sequence shown in SEQ ID NO:32, a VH CDR3 having the amino acid sequence shown in SEQ ID NO: 33, or a variant thereof having one or more conservative amino acid substitutions in CDR1, CDR2, and/or CDR3; and a VL CDR1 having the amino acid sequence shown in SEQ ID NO:34, a VL CDR2 having the amino acid sequence shown in SEQ ID NO:35, and a VL CDR3 having the amino acid sequence shown in SEQ ID NO: 36, or a variant thereof having one or more conservative amino acid substitutions in CDR1, CDR2, and/or CDR3. In some embodiments, the PCSK9 antagonist antibody comprises a light chain having SEQ ID NO: 28 and a heavy chain having SEQ ID NO: 27.

In some embodiments, the LDL-C level is at least about 10% lower than before administration of the initial dose or both the initial dose and the subsequent dose.

In some embodiments, the LDL-C level is at least about or lower than 65, 60, 55, 50, 45, or 40 mg/dL after administration of the initial dose or both the initial dose and the subsequent dose.

In some embodiments, the PCSK9 antagonist antibody described herein is administered to a patient, for example, intravenously or subcutaneously.

The dosing regimen described herein can be used for treating or prophylactically treating a patient suffering from dyslipidemia, hyperlipidemia, hypercholesterolemia, atherosclerosis, cardiovascular disease, and/or coronary heart disease (CVD).

In some embodiments, provided is a use of an anti-PCSK9 antibody in a method of the invention, as set forth in any one of the preceding embodiments.

In some embodiments, provided is an anti-PCSK9 antagonist antibody for use as set forth in any one of the preceding embodiments.

In some embodiments, provided is an anti-PCSK9 antibody in manufacture of a medicament for use in a method as set forth in any one of the preceding embodiments.

BRIEF DESCRIPTION OF THE FIGURES/DRAWINGS

FIG. 1 depicts dose reduction scheme for the Q14d (every 14 days) or Q28d (every 28 days) dosing regimen.

FIGS. 2A and 2B show L1L3 (bococizumab) dose reduction. Subjects randomized to L1L3 100-mg Q14d, 150-mg Q14d, 200-mg Q28d, and 300-mg Q28d had their dose reduced during the study due to LDL-C levels≤25 mg/dL. The percentage of subjects on each dose at each dosing visit is shown for those receiving L1L3 (A) 100-mg Q14d; (B) 150-mg Q14d; (C) 200-mg Q28d; or (D) 300-mg Q28d.

FIG. 3 shows Mean Absolute Change from Baseline in LDL-C at Week 12—For the placebo Q14d, L1L3 Q14d, placebo Q28d, and L1L3 Q28d dose groups.

FIG. 4 shows Placebo-Adjusted Mean Change from Baseline in LDL-C at Week 12—A comparison of observed* (with dose reduction), model-predicted (assuming no dose reduction), and Q28d average* (with dose reduction) data. LS-mean (95% CI) change calculated using a repeated measures model for longitudinal data. Population pharmacokinetic/pharmacodynamic model predictions of mean ($2.5^{th}$, $97.5^{th}$ percentile) change for 100 trials (50 subjects/arm) using baseline demographics from this study. *LS-mean (95% CI) average placebo-adjusted change from days 71 to 85 in the Q28d L1L3 dose groups. †Placebo Q28d average: n=44. ††Placebo Q28d: n=46. †††Placebo Q14d: n=47.

FIG. 5 shows Placebo-Adjusted Mean Change from Baseline in LDL-C to Week 12—Adjusted LS-mean change from baseline in LDL-C versus placebo up to week 12 is shown for the (A) L1L3 Q14d and (B) L1L3 Q28d dose groups. Placebo Q14d: n=44-48; placebo Q28d: n=43-48.

FIGS. 6A and 6B show Mean Percentage Change from Baseline in LDL-C—Change over time is shown for the (A) Q14d and (B) Q28d placebo and L1L3 dose groups.

FIG. 7 shows individual subject LDL-C Levels—Individual subject LDL-C levels over time among those subjects receiving L1L3 150-mg Q14d who had their dose reduced but did not miss a dose are shown. The table shows the percentage of subjects on each L1L3 dose at each dosing visit.

DETAILED DESCRIPTION

Figure 1A:
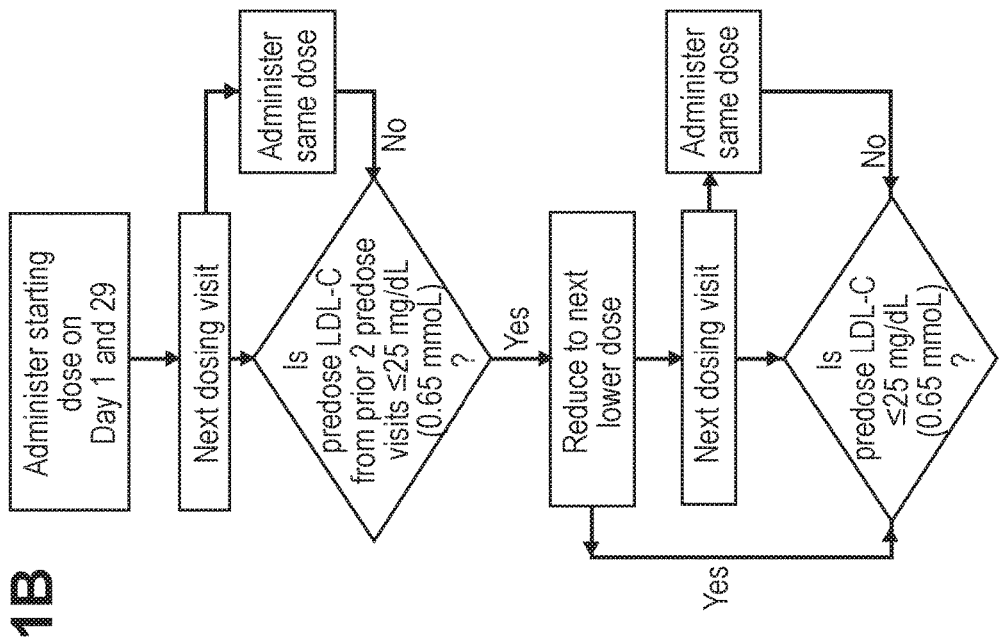

The present invention relates to therapeutic dosing regimens utilizing a dose reduction strategy for treating disorders characterized by marked elevations of low density protein cholesterol (LDL-C) in the plasma of a patient. The subject therapeutic dosing regimens involve delivering as a single administration or plurality administrations an anti-proprotein convertase subtilisin kexin type 9 (PCSK9) antagonist antibody as an initial dose of at least about 100 mg, and delivered as a single administration or plurality of administrations at a subsequent dose in an amount that is about the same as the initial dose, or at least half the initial dose after the patient has a LDL-C level at or below about 25, 20, 15 or 10 mg/dL, preferably at or below about 10 mg/dL. The dosing regimens described herein can be used in the prevention and/or treatment of cholesterol and lipoprotein metabolism disorders, such as, hypercholesterolemia (e.g., heterozygous familial hypercholesterolemia (HetFH) or homozygous familial hypercholesterolemia (HoFH)), dyslipidemia (e.g., mixed dyslipidemia), hyperlipidemia (e.g., heterozygous or homozygous familial and non-familial hyperlipidemia, primary hyperlipidemia), atherosclerosis, acute coronary syndrome and, more generally, and cardiovascular disease (CVD).

In another variation, the invention also relates to therapeutic dosing regimen utilizing a dose reduction strategy for treating disorders in a patient characterized by an elevated low-density lipoprotein cholesterol (LDL-C) level in the blood, comprising administering to the patient a proprotein convertase subtilisin kexin type 9 (PCSK9) antagonist antibody in a dosage regimen comprising an initial dose followed by one or more subsequent doses, characterized in that if the patient presents with an ophthalmic pathology during the dosage regimen, the amount of PCSK9 antagonist antibody in subsequent doses following the presentation of the ophthalmic pathology is reduced relative to the dose prior to the presentation of the ophthalmic pathology.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definition

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding portion") or single chain thereof, fusion proteins comprising an antibody, and any other modified configuration of the immunoglobulin molecule that comprises an antigen recognition site including, for example without limitation, scFv, single domain antibodies (e.g., shark and camelid antibodies), maxibodies, minibodies, intrabodies, diabodies, triabodies, tetrabodies, v-NAR and bis-scFv (see, e.g., Hollinger and Hudson, 2005, Nature Biotechnology 23(9): 1126-1136). An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" or "antigen binding fragment" of an antibody, as used herein, refers to one or more fragments of an intact antibody that retain the ability to specifically bind to a given antigen (e.g., PCSK9). Antigen binding functions of an antibody can be performed by fragments of an intact antibody. Examples of binding fragments encompassed within the term "antigen binding portion" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., 1989, Nature 341:544-546), and an isolated complementarity determining region (CDR).

The term "monoclonal antibody" (Mab) refers to an antibody that is derived from a single copy or clone, including e.g., any eukaryotic, prokaryotic, or phage clone, and not the method by which it is produced. Preferably, a monoclonal antibody of the invention exists in a homogeneous or substantially homogeneous population.

"Humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

As used herein, "human antibody" means an antibody having an amino acid sequence corresponding to that of an antibody that can be produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227: 381; Marks et al., 1991, J. Mol. Biol., 222:581). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al. Monoclonal Antibodies and Cancer Therapy, Alan R. Liss, p. 77, 1985; Boerner et al., 1991, J. Immunol., 147 (1):86-95; and U.S. Pat. No. 5,750,373.

A "bispecific," "dual-specific" or "bifunctional" antibody is a hybrid antibody having two different antigen binding sites. The two antigen binding sites of a bispecific antibody bind to two different epitopes, which may reside on the same or different protein targets (e.g., PCSK9 protein).

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J. Mol. Biol. 196(4): 901-917, 1987). When choosing FR to flank subject CDRs, e.g., when humanizing or optimizing an antibody, FRs from antibodies which contain CDR1 and CDR2 sequences in the same canonical class are preferred.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now ACCELRYS®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As known in the art a "constant region" of an antibody refers to the constant region of the antibody light chain or the constant region of the antibody heavy chain, either alone or in combination.

As used herein, the term "PCSK9" refers to any form of PCSK9 and variants thereof that retain at least part of the activity of PCSK9. Unless indicated differently, such as by specific reference to human PCSK9, PCSK9 includes all mammalian species of native sequence PCSK9, e.g., human, canine, feline, equine, and bovine. One exemplary human PCSK9 is found as Uniprot Accession Number Q8NBP7 (SEQ ID NO: 1).

As used herein, an "anti-PCSK9 antagonist antibody" or "PCSK9 antagonist antibody" refers to an anti-PCSK9 antibody that is able to inhibit PCSK9 biological activity and/or downstream pathway(s) mediated by PCSK9 signaling, including PCSK9-mediated down-regulation of the LDLR, and PCSK9-mediated decrease in LDL blood clearance. A PCSK9 antagonist antibody encompasses antibodies that block, antagonize, suppress or reduce (to any degree including significantly) PCSK9 biological activity, including downstream pathways mediated by PCSK9 signaling, such as LDLR interaction, or elicitation of a cellular response to PCSK9. For purpose of the present invention, it will be explicitly understood that the term "PCSK9 antagonist antibody" encompasses all the previously identified terms, titles, and functional states and characteristics whereby the PCSK9 itself, a PCSK9 biological activity (including but not limited to its ability to mediate any aspect of interaction with the LDLR, down regulation of LDLR, and decreased blood LDL clearance), or the consequences of the biological activity, are substantially nullified, decreased, or neutralized in any meaningful degree. In some embodiments, a PCSK9 antagonist antibody binds PCSK9 and prevents interaction with the LDLR. Examples of PCSK9 antagonist antibodies are provided in, e.g., U.S. Patent Application Publication No. 20100068199, which is herein incorporated by reference in its entirety.

As used herein, a "full antagonist" is an antagonist which, at an effective concentration, essentially completely blocks a measurable effect of PCSK9. By a partial antagonist is meant an antagonist that is capable of partially blocking a measurable effect, but that, even at a highest concentration is not a full antagonist. By essentially completely is meant at least about 80%, preferably, at least about 90%, more preferably, at least about 95%, and most preferably, at least about 98% or 99% of the measurable effect is blocked. The relevant "measurable effects" are described herein and include down regulation of LDLR by a PCSK9 antagonist as assayed in Huh7 cells in vitro, in vivo decrease in blood (or plasma) levels of total cholesterol, and in vivo decrease in LDL levels in blood (or plasma).

The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to PCSK9, e.g., the antibodies compete for binding to the antigen.

As used herein, the term "clinically meaningful" means at least a 10% reduction in blood LDL-cholesterol levels in humans or at least a 10% reduction in total blood cholesterol in mice. It is clear that measurements in plasma or serum can serve as surrogates for measurement of levels in blood.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a PCSK9 epitope is an antibody that binds this epitope with greater affinity, avidity, more readily, and/or with greater duration than it binds to other PCSK9 epitopes or non-PCSK9 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The residue designations in this application are based on the EU numbering scheme of the constant domain (Edelman et al., *Proc. Natl. Acad. Sci. USA*, 63(1):78-85 (1969).

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRII) subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976 J. Immunol., 117:587; and Kim et al., 1994, J. Immunol., 24:249).

By an antibody with an epitope that "overlaps" with another (second) epitope or with a surface on PCSK9 that interacts with the EGF-like domain of the LDLR is meant the sharing of space in terms of the PCSK9 residues that are interacted with. To calculate the percent of overlap, for example, the percent overlap of the claimed antibody's PCSK9 epitope with the surface of PCSK9 which interacts with the EGF-like domain of the LDLR, the surface area of PCSK9 buried when in complex with the LDLR is calculated on a per-residue basis. The buried area is also calculated for these residues in the PCSK9:antibody complex. To prevent more than 100% possible overlap, surface area for residues that have higher buried surface area in the PCSK9: antibody complex than in LDLR:PCSK9 complex is set to values from the LDLR:PCSK9 complex (100%). Percent surface overlap is calculated by summing over all of the LDLR:PCSK9 interacting residues and is weighted by the interaction area.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g., B cell receptor), etc. Such effector functions generally require the Fc region to be combined with a binding domain (e.g., an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g., from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, the terms "atorvastatin", "cerivastatin", "fluvastatin", "lovastatin", "mevastatin", "pitavastatin", "pravastatin", "rosuvastatin" and "simvastatin" include atorvastatin, cerivastatin, fluvastatin, lovastatin, mevastatin, pitavastatin, pravastatin, rosuvastatin, simvastatin, respectively, and any pharmaceutically acceptable salts, or stereoisomers, thereof. As used herein, the term "pharmaceutically acceptable salt" includes salts that are physiologically tolerated by a patient. Such salts are typically prepared from inorganic acids or bases and/or organic acids or bases. Examples of these acids and bases are well known to those of ordinary skill in the art.

As used herein, "treatment" is an approach for obtaining beneficial or desired clinical results. For purposes of this invention, beneficial or desired clinical results include, but are not limited to, one or more of the following: enhancement of LDL clearance and reducing incidence or amelioration of aberrant cholesterol and/or lipoprotein levels resulting from metabolic and/or eating disorders, or including hypercholesterolemia (e.g., HetFH or HoFH), dyslipidemia (e.g., mixed dyslipidemia), hyperlipidemia (e.g., heterozygous or homozygous familial and non-familial), atherosclerosis, acute coronary syndrome (ACS), and, more generally, cardiovascular disease (CVD).

"Reducing incidence" means any of reducing severity (which can include reducing need for and/or amount of (e.g., exposure to) other drugs and/or therapies generally used for this condition. As is understood by those skilled in the art, individuals may vary in terms of their response to treatment, and, as such, for example, a "method of reducing incidence" reflects administering the PCSK9 antagonist antibody as described herein based on a reasonable expectation that such administration may likely cause such a reduction in incidence in that particular individual.

"Ameliorating" means a lessening or improvement of one or more symptoms as compared to not administering a PCSK9 antagonist antibody. "Ameliorating" also includes shortening or reduction in duration of a symptom.

As used herein, an "effective dosage," "therapeutically effective," or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing hypercholesterolemia (e.g., HetFH or HoFH) or one or more symptoms of dyslipidemia (e.g., mixed dyslipidemia), hyperlipidemia (e.g., heterozygous or homozygous familial and non-familial, primary hyperlipidemia), atherosclerosis, cardiovascular disease, or coronary heart disease, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates (e.g., monkeys), horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy, 20th Ed., Mack Publishing, 2000).

The term "$k_{on}$", as used herein, refers to the rate constant for association of an antibody to an antigen. Specifically, the rate constants ($k_{on}$ and $k_{off}$) and equilibrium dissociation constants are measured using Fab antibody fragments (i.e., univalent) and PCSK9.

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Although the disclosed teachings have been described with reference to various applications, methods, and compositions, it will be appreciated that various changes and modifications can be made without departing from the teachings herein and the claimed invention below. The examples are provided to better illustrate the disclosed teachings and are not intended to limit the scope of the teachings presented herein. While the present teachings have been described in terms of these exemplary embodiments, numerous variations and modifications of these exemplary embodiments are possible without undue experimentation. All such variations and modifications are within the scope of the current teachings.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description and/or sequence listings and/or drawings.

In so far as specific examples found herein do not fall within the scope of an invention, said specific example may be explicitly disclaimed.

The use of the term "or" in the claims is used to mean "and/or" unless explicitly indicated to refer to alternatives only or the alternatives are mutually exclusive, although the disclosure supports a definition that refers to only alternatives and "and/or." As used herein the specification, "a" or "an" may mean one or more, unless clearly indicated otherwise. As used herein in the claim(s), when used in conjunction with the word "comprising", the words "a" or "an" may mean one or more than one. As used herein "another" may mean at least a second or more. Further, unless otherwise required by context, singular terms shall include pluralities and plural terms shall include the singular. The words "comprises/comprising" and the words "having/including" when used herein with reference to the present invention are used to specify the presence of stated features, integers, steps or components but does not preclude the presence or addition of one or more other features, integers, steps, components or groups thereof.

Unless otherwise defined, all technical and scientific terms used herein have the same meaning as commonly understood by one of ordinary skill in the art to which this invention belongs. Exemplary methods and materials are described herein, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. The materials, methods, and examples are illustrative only and not intended to be limiting.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

Published information related to anti-PCSK9 antibodies includes the following publications: PCT/IB2009/053990, published Mar. 18, 2010 as WO 2010/029513, U.S. patent application Ser. No. 12/558,312, published Dec. 20, 2011 as U.S. Pat. No. 8,080,243, and U.S. patent application Ser. No. 14/232,559, published Jun. 12, 2014 as US20140161821, each of which is herein incorporated by reference in its entirety.

Exemplary methods and materials are described herein, although methods and materials similar or equivalent to those described herein can also be used in the practice or testing of the present invention. The materials, methods, and examples are illustrative only and not intended to be limiting.
PCSK9 Antibody Dosing Regimens
Reduced Dosing Regimens In one aspect, the invention provides a therapeutic dosing regimen utilizing a dose reduction strategy for treating disorders characterized by marked elevations of LDL-C in the plasma of a patient. Accordingly, in some embodiments, provided is a PCSK9 antagonist antibody for use in the treatment of a disorder in a patient characterized by an elevated low-density lipoprotein cholesterol (LDL-C) level in the blood, wherein the PCSK9 antagonist antibody is delivered as a single administration or plurality of administrations at an initial dose of at least about 100 mg, and delivered as a single administration or plurality of administrations at a subsequent dose in an amount that is about the same as the initial dose, or at least half the initial dose after the patient has a LDL-C level at or below about 25, 20, 15 or 10 mg/dL, preferably at or below about 10 mg/dL, wherein all administrations are separated in time from each other by at least about two weeks.

In some embodiments, provided is a method for treating a patient susceptible to or diagnosed with a disorder characterized by an elevated low-density lipoprotein cholesterol (LDL-C) level in the blood, comprising: delivering to the patient as a single administration or plurality of administrations an initial dose of at least about 100 mg of a proprotein convertase subtilisin kexin type 9 (PCSK9) antagonist antibody; and delivering to the patient a single administration or plurality of administrations at a subsequent dose that is about the same as the initial dose, or at least half the initial dose after the patient has a LDL-C level at or below about 25, 20, 15 or 10 mg/dL, preferably at or below about 10 mg/dL, wherein all administrations are separated in time from each other by at least about two weeks.

In some embodiments, provided is a use of a single administration or plurality of administrations an initial dose of at least about 100 mg of a PCSK9 antagonist antibody, in the manufacture of a medicament for treating a patient susceptible to or diagnosed with a disorder characterized by an elevated low-density lipoprotein cholesterol (LDL-C) level in the blood, wherein a single administration or plurality of administrations at a subsequent dose is about the same as the initial dose, or at least half the initial dose after the patient has a LDL-C level at or below about 25, 20, 15, or 10 mg/dL, preferably at or below about 10 mg/dL, and wherein all administrations are separated in time from each other by at least about two weeks.

The cholesterol and lipoprotein metabolism related disorders include, but are not limited to, hypercholesterolemia (e.g., heterozygous familial hypercholesterolemia (HetFH) or homozygous familial hypercholesterolemia (HoFH)), dyslipidemia (e.g., mixed dyslipidemia), hyperlipidemia (e.g., heterozygous or homozygous familial and non-familial hyperlipidemia, primary hyperlipidemia), atherosclerosis, acute coronary syndrome, who are intolerant of statins or for whom statins are contraindicated, and cardiovascular disease (CVD). In some embodiments, CVD or cardiovascular events include, but are not limited to, myocardial infarction, hospitalization for heart failure (HF), hospitalization for unstable angina (e.g., needing revascularization), stroke, cardiovascular (CV) death, and hospitalization for revascularization.

In some embodiments, the dosing regimen comprises delivering as a single administration or plurality of administrations at an initial dose of at least about 100 mg to about 2000 mg of the PCSK9 antagonist antibody (e.g., which specifically binds to the human PCSK9 of SEQ ID NO: 1), and delivering as a single administration or plurality of administrations at a subsequent dose in an amount that is about the same as the initial dose, or at least half the initial dose after the patient has a LDL-C level at or below about 25, 20, 15 or 10 mg/dL, preferably at or below about 10 mg/dL, wherein all administrations are separated in time from each other by at least about two weeks. In some embodiments, the PCSK9 antagonist antibody blocks LDLR binding to the human PCSK9 of SEQ ID NO: 1. In some embodiments, the PCSK9 antagonist antibody interacts with the EGF-like domain of the LDLR (e.g., SEQ ID NO: 15 or amino acid residues 314-353 of SEQ ID NO: 16). In some embodiments, the PCSK9 antagonist antibody is alirocumab (PRALUENT™); evolocumab (REPATHA™); REGN728; LGT209; RG7652; LY3015014; J16, L1L3 (bococizumab); 31H4, 11F1, 12H11, 8A3, 8A1, or 3C4 (see, e.g., U.S. Pat. No. 8,030,457); 300N (see, e.g., U.S. Pat. No. 8,062,640); or 1D05 (see, e.g., U.S. Pat. No. 8,188,234). In some embodiments, the anti-PCSK9 antibody is bococizumab, alirocumab (PRALUENT™), or evolocumab (REPATHA™).

In some embodiments, the initial dose for the PCSK9 antagonist antibody is about any of 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg 192 mg, 193 mg, 194 mg, 195 mg, 196 mg, 199 mg, 198 mg, 199 mg, 200 mg, 250, 300, 350, 400, 450, or 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg. In some embodiments, the subsequent dose for the PCSK9 antagonist antibody is about any of 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 105 mg, 110 mg, 115 mg, 120 mg, 125 mg, 130 mg, 135 mg, 140 mg, 145 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 325 mg, 350 mg, 375 mg, 400 mg, 425 mg, 450 mg, 475 mg, 500 mg, 600 mg, 700 mg, 800 mg, 900 mg, or 1000 mg. In some embodiments, at least half of the initial dose is administered as a subsequent dose after the patient has a LDL-C level at or below about 10 mg/dL, 11 mg/dL, 12 mg/dL, 13 mg/dL, 14 mg/dL, 15 mg/dL, 16 mg/dL, 17 mg/dL, 18 mg/dL, 19 mg/dL, 20 mg/dL, 21 mg/dL, 22 mg/dL, 23 mg/dL, 24 mg/dL, 25 mg/dL, 26 mg/dL, 27 mg/dL, 28 mg/dL, 29 mg/dL, 30 mg/dL, 31 mg/dL, 32 mg/dL, 33 mg/dL, 34 mg/dL, 35 mg/dL, 36 mg/dL, 37 mg/dL, 38 mg/dL, 39 mg/dL, or 40 mg/dL. In some embodiments, all administrations are separated in time from each other every other week, every three weeks, every four weeks, every five weeks, every six weeks, every seven weeks, every eight weeks, every nine weeks, every ten weeks, every eleven weeks, or every twelve weeks. In some embodiments, all administrations are separated in time from each other about every other week weeks (e.g., two weeks or 13-16 days) or about every four weeks (e.g., 27-32 days).

In some embodiments, the subsequent dose is about two thirds of the initial dose, or one half the initial dose.

In one embodiment, the initial dose of PCSK9 antagonist antibody is administered at about 150 mg, and the subsequent dose is administered at 150 mg every two weeks after the patient has a LDL-C level above about 25, 20, 15 or 10 mg/dL, preferably at or above about 10 mg/dL. In other embodiment, the initial dose of PCSK9 antagonist antibody is administered at about 150 mg, and the subsequent dose is reduced below 150 mg every two weeks after the patient has a LDL-C level below about 25, 20, 15 or 10 mg/dL. In some embodiments, the subsequent dose is reduced to 100 mg after the patient has a LDL-C at or below about 25, 20, 15 or 10 mg/dL, preferably at or below about 10 mg/dL. In some embodiments, the subsequent dose is reduced to 75 mg after the patient has a LDL-C at or below about 25, 20, 15 or 10 mg/dL, preferably at or below about 10 mg/dL. For example, the subsequent dose of 75 mg is administered to the patient after the patient has at least about two consecutive assessments of LDL-C at or below about 25, 20, 15 or 10 mg/dL, preferably at or below about 10 mg/dL. In some embodiments, the patient receiving the dose reduction has at least about three, four, five, six, seven, or eight consecutive assessments of LDL-C at or below about 25, 20, 15 or 10 mg/dL, preferably at or below about 10 mg/dL.

In another embodiment, the initial dose of PCSK9 antagonist antibody is administered at about 140 mg, and the subsequent dose is administered at 140 mg every two weeks after the patient has a LDL-C level above about 25, 20, 15 or 10 mg/dL, preferably at or above 10 mg/dL. In some embodiments, the subsequent dose is reduced to 70 mg after the patient has a LDL-C at or below about 25, 20, 15 or 10 mg/dL, preferably at or below about 10 mg/dL. For example, the subsequent dose of 70 mg is administered to the patient after the patient has at least about two consecutive assessments of LDL-C at or below about 25, 20, 15 or 10 mg/dL, preferably at or below about 10 mg/dL. In some embodiments, the patient receiving the dose reduction has at least about three, four, five, six, seven, or eight consecutive assessments of LDL-C at or below about 25, 20, 15 or 10 mg/dL, preferably at or below about 10 mg/dL.

In one variation, provided is a dosing regimen, following an initial dose of at least about 100 mg, the subsequent dose is reduced to half the initial dose and is administered every two weeks after the patient has a LDL-C at or below 25, 20, 15 or 10 mg/dL, preferably at or below about 10 mg/dL, and a second subsequent dose is administered every two weeks and is even further reduced to one third or one quarter the initial dose, delivered as a single or plurality of administrations, after the patient has a LDL-C again at or below about 25, 20, 15 or 10 mg/dL, preferably at or below about 10 mg/dL, while on the subsequent dose.

In another variation, provided is a dosing regimen, following an initial dose of at least about 100 mg, the subsequent dose is reduced to two thirds the initial dose and is administered every two weeks after the patient has a LDL-C at or below 25, 20, 15 or 10 mg/dL, preferably at or below about 10 mg/dL, and a second subsequent dose is administered every two weeks and is then even further reduced to one third or one quarter the initial dose, delivered as a single or plurality of administrations, after the patient had a LDL-C again at or below about 25, 20, 15 or 10 mg/dL, preferably at or below about 10 mg/dL, while on the subsequent dose.

In another variation, provided is a dosing regimen, following an initial dose of at least about 100 mg, the subsequent dose is reduced to half the initial dose and is administered every two weeks after the patient has a LDL-C at or below 25, 20, 15 or 10 mg/dL, preferably at or below about 10 mg/dL, and the subsequent dose is then administered every four weeks after the patient has a LDL-C again at or below 25, 20, 15 or 10 mg/dL, preferably at or below about 10 mg/dL, while on the subsequent dose every two weeks. In some embodiments, the subsequent dose is administered to the patient every two weeks after the patient has at least about two consecutive assessments of LDL-C at or below about 25, 20, 15 or 10 mg/dL, preferably at or below about 10 mg/dL, and the subsequent dose is further administered to the patient every four weeks after the patient has at least about another two consecutive assessments of LDL-C at or below about 25, 20, 15 or 10 mg/dL, preferably at or below about 10 mg/dL, while on the subsequent dose every two weeks. In some embodiments, the patient receiving the longer dosing duration (e.g., every four weeks) has at least about three, four, five, six, seven, or eight consecutive assessments of LDL-C at or below about 25, 20, 15 or 10 mg/dL, preferably at or below about 10 mg/dL. Accordingly, in some embodiments, provided is a dosing regimen which comprises delivering an initial dose of about 150 mg of the PCSK9 antagonist antibody (e.g., specifically binding to the human PCSK9 of SEQ ID NO: 1), and delivering a subsequent dose of about 75 mg of the PCSK9 antagonist antibody every two weeks after the patient has at least about two consecutive assessments of LDL-C level at or below about 25, 20, 15 or 10 mg/dL, preferably at or below about 10 mg/dL, and delivering a subsequent dose of about 75 mg every four weeks after the patient has at least about another two consecutive assessments of LDL-C level at or below about 25, 20, 15 or 10 mg/dL, preferably at or below about 10 mg/dL. In some embodiments, provided is a dosing regimen which comprises delivering an initial dose of about 150 mg of the PCSK9 antagonist antibody (e.g., specifically binding to the human PCSK9 of SEQ ID NO: 1), and delivering a subsequent dose of about 75 mg of the PCSK9 antagonist antibody every two weeks after the patient has at least about two consecutive assessments of LDL-C level at or below about 10 mg/dL, and delivering a subsequent dose of about 75 mg every four weeks after the patient has at least about another two consecutive assessments of LDL-C level at or below about 10 mg/dL.

The PCSK9 antagonist antibody can further be administered according to one or more dosing regimens disclosed herein to an individual on stable doses of a statin. The stable doses can be, for example without limitation, a daily dose or an every-other-day dose of a statin. A variety of statins known to those of skill in the art, and include, for example without limitation, atorvastatin, simvastatin, lovastatin, pravastatin, rosuvastatin, fluvastatin, cerivastatin, mevastatin, pitavastatin, and statin combination therapies. Non-limiting examples of statin combination therapies include atorvastatin plus amlodipine (CADUET™), simvastatin plus ezetimibe (VYTORIN™), lovastatin plus niacin (ADVICOR™), and simvastatin plus niacin (SIMCOR™).

In some embodiments, an individual has been on stable doses of a statin for at least one, two, three, four, five or six weeks prior to administration of an initial dose of the PCSK9 antagonist antibody as described herein. Preferably, the individual on stable doses of a statin has a fasting LDL-C greater than or equal to about 70 mg/dL prior to administration of an initial dose of the PCSK9 antagonist antibody. In some embodiments, the individual on stable doses of a statin has a fasting LDL-C greater than or equal to about 80, 90, 100, 110, 120, 130, 140, 150, 160, 170, 180, 190 or 200 mg/dL prior to administration of an initial dose of the PCSK9 antagonist antibody.

In some embodiments, an individual had been on stable doses of a statin (e.g., 1 day, 14 days, 1 month, 2 months, 3 months, 1 year, 2 years ago, etc.) prior to administration of an initial dose of the PCSK9 antagonist antibody as described herein, and initiate the statin doses with the PCSK9 antagonist antibody dosing regimen at the same time.

For the purpose of the present invention, a typical statin dose might range from about 1 mg to about 80 mg, depending on the factors mentioned above. For example, a statin dose of about any of 0.3 mg, 0.5 mg, 1 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 30 mg, 31 mg, 32 mg, 33 mg, 34 mg, 35 mg, about 36 mg, about 37 mg, about 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, about 56 mg, about 57 mg, about 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, or 80 mg may be used.

In preferred embodiments, a dose of 40 mg or 80 mg atorvastatin is used. In other embodiments, a dose of 20 mg or 40 mg rosuvastatin is used. In other embodiments, a dose of 40 mg or 80 mg simvastatin is used.

Reduced Dosing Regimen in Patients Presented with Ophthalmic Pathology

In the eye, the cornea requires cholesterol for membrane formation associated with epithelial turnover and wound healing (see, e.g., Cenedella and Fleschner, J Lipid Res. 30:1079-1084 (1989)). Studies characterizing the origin of the cholesterol needed by the rabbit cornea suggest that most of the cornea's sterol synthesis occurs in the epithelial cell fraction and that the cornea has the capacity to satisfy all of its sterol requirements by de novo synthesis.

In some circumstances, de novo synthesis of cholesterol may be slightly lower in the peripheral cornea compared with central cornea, suggesting that some exogenous or circulating cholesterol is delivered to the peripheral cornea. This is consistent with the vasculature of the eye, in which the limbal blood supply is in contact with the peripheral cornea.

Cholesterol deposition in the peripheral cornea occurs in the context of lipoprotein disorders such as Tangier disease and Familial Apo A-I deficiency. In the context of atherosclerosis, it has been observed that cholesterol deposition in the peripheral cornea and blood vessel wall are similar in that the deposition process is accelerated in both tissues when atherogeneic lipoproteins such as low density lipoprotein (LDL) circulate at elevated levels (Gaynor et al "*Cholesterol accumulation in human cornea: evidence that extracellular cholesteryl ester-rich lipid particles deposit independently of foam cells.*" J Lipid Res. 1996; 37:1849-1861).

In some aspects, use of a PCSK9 inhibitor may result in extremely low levels of circulating cholesterol including LDL. Such low levels of LDL may limit the supply of exogenous cholesterol to the cornea, in particular the peripheral cornea. Although the de novo cholesterol synthesis capabilities of the cornea can buffer it from these low levels of circulating cholesterol, persistently low levels of cholesterol over time may affect the ability of the cornea (and the peripheral cornea especially) to regenerate its epithelial layer and heal from wounds and other ophthalmic pathologies.

In some aspects, the ophthalmic pathology relates to one or more symptoms or conditions selected from the group consisting of blepharitis, cataract, conjunctivitis, corneal erosion, glaucoma, ocular hyperaemia, vitreous floaters, dry eye, eye hemorrhage, eye pruritus, eyelid pain, and Miller Fisher Syndrome. In some aspects, the ophthalmic pathology is conjunctivitis. In some aspects, the ophthalmic pathology is Miller Fischer Syndrome. In some aspects, the ophthalmic pathology excludes Miller Fisher Syndrome. In some aspects, the ophthalmic pathology relates to one or more symptoms or conditions selected from the group consisting of corneal erosion or ocular hyperaemia. In some aspects, the ophthalmic pathology is ocular hyperaemia.

In some aspects, the ophthalmic pathology is a corneal pathology. In some aspects, the ophthalmic pathology is a pathology to either or both of the endothelium or epithelium of the cornea. In some aspects, the ophthalmic pathology is a trauma to the cornea (such as caused by a foreign body making contact with the cornea). In some aspects, the ophthalmic pathology may be an infection (for example, a bacterial or fungal infection; for example, such as an infection from a contaminated contact lens; situations like these can cause painful inflammation and corneal infections called keratitis; which can also lead to corneal erosion).

In some aspects, the ophthalmic pathology is a corneal pathology. In some aspects, the ophthalmic pathology is corneal dystrophy. The corneal dystrophy may be selected from the group consisting of Fuchs' dystrophy, keratoconus, lattice dystrophy, and map-dot-fingerprint dystrophy (epithelial basement membrane dystrophy). In some aspects, the ophthalmic pathology is herpes zoster (shingles). In some aspects, the ophthalmic pathology is swelling of the corneal epithelium. In some aspects, the ophthalmic pathology is iridocorneal endothelial syndrome. In some aspects, the ophthalmic pathology is epithelial erosion. In some aspects, the ophthalmic pathology is ocular herpes. In some aspects, the ophthalmic pathology is a corneal transplant. In some aspects, the ophthalmic pathology is laser eye surgery (LASIK, or "laser-assisted in situ keratomileusis").

Accordingly, in some aspects, the initial dose of PCSK9 antagonist antibody is administered at about 75 mg, and the subsequent dose is administered at less than about 75 mg every two weeks after the patient presents with an ophthalmic pathology.

In some aspects, the initial dose of PCSK9 antagonist antibody is administered at about 75 mg, and the subsequent dose is administered at less than about 50 mg every two weeks after the patient presents with an ophthalmic pathology.

In some aspects, the initial dose of PCSK9 antagonist antibody is administered at about 150 mg, and the subsequent dose is administered at less than about 150 mg every two weeks after the patient presents with an ophthalmic pathology.

In some aspects, the initial dose of PCSK9 antagonist antibody is administered at about 150 mg, and the subsequent dose is administered at less than about 100 mg every two weeks after the patient presents with an ophthalmic pathology.

In some aspects, the initial dose of PCSK9 antagonist antibody is administered at about 150 mg, and the subsequent dose is administered at less than about 75 mg every two weeks after the patient presents with an ophthalmic pathology.

In some aspects, the initial dose of PCSK9 antagonist antibody is administered at about 150 mg, and the subsequent dose is administered at less than about 50 mg every two weeks after the patient presents with an ophthalmic pathology.

In some aspects, the initial dose of PCSK9 antagonist antibody is administered at about 140 mg, and the subsequent dose is administered at less than about 140 mg every two weeks after the patient presents with an ophthalmic pathology.

In some aspects, the initial dose of PCSK9 antagonist antibody is administered at about 140 mg, and the subsequent dose is administered at less than about 100 mg every two weeks after the patient presents with an ophthalmic pathology.

In some aspects, the initial dose of PCSK9 antagonist antibody is administered at about 140 mg, and the subsequent dose is administered at less than about 70 mg every two weeks after the patient presents with an ophthalmic pathology.

In some aspects, the initial dose of PCSK9 antagonist antibody is administered at about 140 mg, and the subsequent dose is administered at less than about 50 mg every two weeks after the patient presents with an ophthalmic pathology.

In some aspects, the initial dose of PCSK9 antagonist antibody is administered at about 420 mg, and the subsequent dose is administered at less than about 420 mg every month after the patient presents with an ophthalmic pathology.

In some aspects, the initial dose of PCSK9 antagonist antibody is administered at about 420 mg, and the subsequent dose is administered at less than about 300 mg every month after the patient presents with an ophthalmic pathology.

In some aspects, the initial dose of PCSK9 antagonist antibody is administered at about 420 mg, and the subsequent dose is administered at less than about 250 mg every month after the patient presents with an ophthalmic pathology.

In some aspects, the initial dose of PCSK9 antagonist antibody is administered at about 420 mg, and the subsequent dose is administered at less than about 200 mg every month after the patient presents with an ophthalmic pathology.

In some aspects, the initial dose of PCSK9 antagonist antibody is administered at about 420 mg, and the subsequent dose is administered at less than about 150 mg every month after the patient presents with an ophthalmic pathology.

In some aspects, the initial dose of PCSK9 antagonist antibody is administered at about 420 mg, and the subsequent dose is administered at less than about 100 mg every month after the patient presents with an ophthalmic pathology.

In some aspects, the initial dose of PCSK9 antagonist antibody is administered at about 150 mg, and the subsequent dose is administered at about 75 mg every two weeks after the patient presents with an ophthalmic pathology.

In some aspects, the initial dose of PCSK9 antagonist antibody is administered at about 150 mg, and the subsequent dose is administered at about 75 mg every three weeks after the patient presents with an ophthalmic pathology.

In some aspects, the initial dose of PCSK9 antagonist antibody is administered at about 150 mg, and the subsequent dose is administered at about 75 mg every four weeks after the patient presents with an ophthalmic pathology.

In some aspects, the initial dose of PCSK9 antagonist antibody is administered at about 75 mg, and the subsequent dose is administered at about 75 mg every three weeks after the patient presents with an ophthalmic pathology.

In some aspects, the initial dose of PCSK9 antagonist antibody is administered at about 75 mg, and the subsequent doses are administered at about 75 mg every four weeks after the patient presents with an ophthalmic pathology.

In some aspects, the initial dose of PCSK9 antagonist antibody is administered at about 75 mg, and the subsequent dose is administered at about 75 mg every two weeks, and after the patient presents with an ophthalmic pathology, the subsequent doses are postponed until treatment of the ophthalmic pathology has been completed to the satisfaction of the treating physician.

In some aspects, the initial dose of PCSK9 antagonist antibody is administered at about 100 mg, and the subsequent dose is administered at about 100 mg every two weeks, and after the patient presents with an ophthalmic pathology, the subsequent doses are postponed until treatment of the ophthalmic pathology has been completed to the satisfaction of the treating physician.

In some aspects, the initial dose of PCSK9 antagonist antibody is administered at about 140 mg, and the subsequent dose is administered at about 140 mg every two weeks, and after the patient presents with an ophthalmic pathology, the subsequent doses are postponed until treatment of the ophthalmic pathology has been completed to the satisfaction of the treating physician.

In some aspects, the initial dose of PCSK9 antagonist antibody is administered at about 150 mg, and the subsequent dose is administered at about 150 mg every two weeks, and after the patient presents with an ophthalmic pathology, the subsequent doses are postponed until treatment of the ophthalmic pathology has been completed to the satisfaction of the treating physician.

In some aspects, the initial dose of PCSK9 antagonist antibody is administered at between about 100 mg and about 180 mg, and the subsequent dose is administered at between about 100 mg and about 180 mg every two weeks, and after the patient presents with an ophthalmic pathology, the subsequent doses are postponed until treatment of the ophthalmic pathology has been completed to the satisfaction of the treating physician.

In some aspects, the initial dose of PCSK9 antagonist antibody is administered at about 250 mg, and the subsequent dose is administered at about 250 mg every four weeks, and after the patient presents with an ophthalmic pathology, the subsequent doses are postponed until treatment of the ophthalmic pathology has been completed to the satisfaction of the treating physician.

In some aspects, the initial dose of PCSK9 antagonist antibody is administered at about 300 mg, and the subsequent dose is administered at about 300 mg every four weeks, and after the patient presents with an ophthalmic pathology, the subsequent doses are postponed until treatment of the ophthalmic pathology has been completed to the satisfaction of the treating physician.

In some aspects, the initial dose of PCSK9 antagonist antibody is administered at about 350 mg, and the subsequent dose is administered at about 350 mg every four weeks, and after the patient presents with an ophthalmic pathology, the subsequent doses are postponed until treatment of the ophthalmic pathology has been completed to the satisfaction of the treating physician.

In some aspects, the initial dose of PCSK9 antagonist antibody is administered at about 400 mg, and the subsequent dose is administered at about 400 mg every four weeks, and after the patient presents with an ophthalmic pathology, the subsequent doses are postponed until treatment of the ophthalmic pathology has been completed to the satisfaction of the treating physician.

In some aspects, the initial dose of PCSK9 antagonist antibody is administered at about 420 mg, and the subsequent dose is administered at about 420 mg every four weeks, and after the patient presents with an ophthalmic pathology, the subsequent doses are postponed until treatment of the ophthalmic pathology has been completed to the satisfaction of the treating physician.

In one embodiment, the initial dose of PCSK9 antagonist antibody is administered at about 150 mg, and the subsequent dose is administered at less than about 150 mg every two weeks after the patient presents with an ophthalmic pathology.

In one embodiment, the initial dose of PCSK9 antagonist antibody is administered at about 150 mg, and the subsequent dose is administered at less than about 100 mg every two weeks after the patient presents with an ophthalmic pathology.

In one embodiment, the initial dose of PCSK9 antagonist antibody is administered at about 150 mg, and the subsequent dose is administered at less than about 75 mg every two weeks after the patient presents with an ophthalmic pathology.

In one embodiment, the initial dose of PCSK9 antagonist antibody is administered at about 150 mg, and the subsequent dose is administered at less than about 50 mg every two weeks after the patient presents with an ophthalmic pathology.

In one embodiment, the initial dose of PCSK9 antagonist antibody is administered at about 140 mg, and the subsequent dose is administered at less than about 140 mg every two weeks after the patient presents with an ophthalmic pathology.

In one embodiment, the initial dose of PCSK9 antagonist antibody is administered at about 140 mg, and the subsequent dose is administered at less than about 100 mg every two weeks after the patient presents with an ophthalmic pathology.

In one embodiment, the initial dose of PCSK9 antagonist antibody is administered at about 140 mg, and the subsequent dose is administered at less than about 70 mg every two weeks after the patient presents with an ophthalmic pathology.

In one embodiment, the initial dose of PCSK9 antagonist antibody is administered at about 140 mg, and the subsequent dose is administered at less than about 50 mg every two weeks after the patient presents with an ophthalmic pathology.

In one embodiment, the initial dose of PCSK9 antagonist antibody is administered at about 420 mg, and the subsequent dose is administered at less than about 420 mg every month after the patient presents with an ophthalmic pathology.

In one embodiment, the initial dose of PCSK9 antagonist antibody is administered at about 420 mg, and the subsequent dose is administered at less than about 300 mg every month after the patient presents with an ophthalmic pathology.

In one embodiment, the initial dose of PCSK9 antagonist antibody is administered at about 420 mg, and the subsequent dose is administered at less than about 250 mg every month after the patient presents with an ophthalmic pathology.

In one embodiment, the initial dose of PCSK9 antagonist antibody is administered at about 420 mg, and the subsequent dose is administered at less than about 200 mg every month after the patient presents with an ophthalmic pathology.

In one embodiment, the initial dose of PCSK9 antagonist antibody is administered at about 420 mg, and the subsequent dose is administered at less than about 150 mg every month after the patient presents with an ophthalmic pathology.

In one embodiment, the initial dose of PCSK9 antagonist antibody is administered at about 420 mg, and the subsequent dose is administered at less than about 100 mg every month after the patient presents with an ophthalmic pathology.

In some embodiments, the dosing regimen comprises delivering as a single administration or plurality of administrations at an initial dose of at least about 100 mg to about 2000 mg of the PCSK9 antagonist antibody (e.g., which specifically binds to the human PCSK9 of SEQ ID NO: 1), and delivering as a single administration or plurality of administrations at a subsequent dose in an amount that is less than the initial dose after the patient presented with an ophthalmic pathology.

In one embodiment, the initial dose of PCSK9 antagonist antibody is administered at about 150 mg, and the subsequent dose is administered at 150 mg every two weeks after the ophthalmic pathology has been treated. In some aspects, the treatment of the ophthalmic pathology may be terminated under direction of a treating physician.

Advantageously, administration of the PCSK9 antagonist antibody using the dosing regimen as described herein results in lower blood LDL-cholesterol in patients. Preferably, blood LDL-cholesterol is at least about 10% or 15% lower than before administration of the initial dose or both the initial dose and the subsequent dose. More preferably, blood LDL-cholesterol is at least about 20% lower than before administration of the initial dose or both the initial dose and the subsequent dose. Yet more preferably, blood LDL-cholesterol is at least 30% lower than before administration of the initial dose or both the initial dose and the subsequent dose. Advantageously, blood LDL-cholesterol is at least 40% lower than before administration of the initial dose or both the initial dose and the subsequent dose. More advantageously, blood LDL-cholesterol is at least 50% lower than before administration of the initial dose or both the initial dose and the subsequent dose. Very preferably, blood LDL-cholesterol is at least 60% lower than before administration of the initial dose or both the initial dose and the subsequent dose. Most preferably, blood LDL-cholesterol is at least 70% lower than before administration of the initial dose or both the initial dose and the subsequent dose of the antibody.

Accordingly, in some embodiments, the blood LDL-cholesterol is at least about or lower than 65 mg/dL after administration of the initial dose or both the initial dose and the subsequent dose. In some embodiments, the blood LDL-cholesterol is at least about or lower than 65 mg/dL, 60 mg/dL, 55 mg/dL, 50 mg/dL, 45 mg/dL, 40 mg/dL, 35 mg/dL, or 30 mg/dL after administration of the initial dose or both the initial dose and the subsequent dose.

The PCSK9 antagonist antibody described herein can be administered to a subject via any suitable route. It should be apparent to a person skilled in the art that the examples described herein are not intended to be limiting but to be illustrative of the techniques available. Accordingly, in some embodiments, the PCSK9 antagonist antibody is administered to an individual in accord with known methods, such as intravenous administration, e.g., as a bolus or by continuous infusion over a period of time, by subcutaneous, intramuscular, intraperitoneal, intracerebrospinal, transdermal, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the PCSK9 antagonist antibody can be aerosolized using a fluorocarbon formulation and a metered dose inhaler, or inhaled as a lyophilized and milled powder.

In some embodiments, the PCSK9 antagonist antibody is administered via site-specific or targeted local delivery techniques. Examples of site-specific or targeted local delivery techniques include various implantable depot sources of the PCSK9 antagonist antibody or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publ. No. WO 00/53211 and U.S. Pat. No. 5,981,568.

With respect to all methods described herein, reference to any PCSK9 antagonist antibody also includes compositions comprising one or more additional agents. These compositions may further comprise suitable excipients, such as pharmaceutically acceptable excipients including buffers, which are well known in the art. The present invention can be used alone or in combination with other conventional methods of treatment.

Various formulations of an PCSK9 antagonist antibody may be used for combination administration. In some embodiments, the PCSK9 antagonist antibody can be administered neat. In some embodiments, the PCSK9 antagonist antibody can also be administered via inhalation. In some embodiments, the PCSK9 antagonist antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy, 21st Ed., Mack Publishing (2005).

These agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing the PCSK9 antagonist antibody are prepared by methods known in the art, such as described in Epstein, et al., 1985, Proc. Natl. Acad. Sci. USA 82:3688; Hwang, et al., 1980, Proc. Natl Acad. Sci. USA 77:4030; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy, 21st Ed., Mack Publishing (2005).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for in vivo administration must be sterile. This is readily accomplished by, for example, filtration through sterile filtration membranes. Therapeutic PCSK9 antagonist antibodies are generally placed into a container having a sterile access port, for example, an intravenous solution bag or vial having a stopper pierceable by a hypodermic injection needle.

Suitable emulsions may be prepared using commercially available fat emulsions, such as Infralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing an PCSK9 antagonist antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

PCSK9 Antagonist Antibodies

A description follows as to an exemplary technique for the production of the antibodies used in accordance with the present invention. The PCSK9 antigen to be used for production of antibodies may be, e.g. full-length human PCSK9, full length mouse PCSK9, and various peptides fragments of PCSK9. Other forms of PCSK9 useful for generating antibodies will be apparent to those skilled in the art.

As will be appreciated, antibodies for use in the present invention may be derived from hybridomas but can also be expressed in cell lines other than hybridomas. Sequences encoding the cDNAs or genomic clones for the particular antibodies can be used for transformation of suitable mammalian or nonmammalian host cells. Mammalian cell lines available as hosts for expression are well known in the art and include many immortalized cell lines available from the American Type Culture Collection (ATCC), including but not limited to Chinese hamster ovary (CHO) cells, NSO, HeLa cells, baby hamster kidney (BHK) cells, monkey kidney cells (COS), and human hepatocellular carcinoma cells (e.g., Hep G6). Non-mammalian cells can also be employed, including bacterial, yeast, insect, and plant cells. Site directed mutagenesis of the antibody CH6 domain to eliminate glycosylation may be preferred in order to prevent changes in either the immunogenicity, pharmacokinetic, and/or effector functions resulting from non-human glycosylation. The glutamine synthase system of expression is discussed in whole or part in connection with European Patents 616 846, 656 055, and 363 997 and European Patent Application 89303964.4. Further, a dihydrofolate reductase (DHFR) expression system, including those known in the art, can be used to produce the antibody.

In some embodiments, the invention is practiced using the PCSK9 antagonist antibody blocking the LDLR binding of the human PCSK9 (e.g., SEQ ID NO: 1). In some embodiments, the PCSK9 antagonist antibody interacts with the EGF-like domain of the LDLR (e.g., SEQ ID NO: 15 or amino acid residues 314-353 of SEQ ID NO: 16). In some embodiments, the PCSK9 antagonist antibody is alirocumab (PRALUENT™); evolocumab (REPATHA™); REGN728; LGT209; RG7652; LY3015014; J16, L1L3 (bococizumab); 31H4, 11F1, 12H11, 8A3, 8A1, or 3C4 (see, e.g., U.S. Pat. No. 8,030,457); 300N (see, e.g., U.S. Pat. No. 8,062,640); or 1D05 (see, e.g., U.S. Pat. No. 8,188,234). In some embodiments, the anti-PCSK9 antibody is bococizumab, alirocumab (PRALUENT™), or evolocumab (REPATHA™).

In some embodiments, the invention is practiced using the PCSK9 antagonist antibody recognizing an epitope of human PCSK9 comprising amino acid residues 153-155, 194, 195, 197, 237-239, 367, 369, 374-379 and/or 381 of the human PCSK9 (e.g., SEQ ID NO: 1).

In some embodiments, the invention is practiced using the PCSK9 antagonist antibody recognizing an epitope of human PCSK9 comprising amino acid residues 153, 154, 194, 238, 369, 374, 377, and/or 379 of the human PCSK9 (e.g., SEQ ID NO: 1).

In some embodiments, the invention is practiced using an antibody comprising three CDRS from a heavy chain variable region having the amino acid sequence shown in SEQ ID NO: 2 and three CDRS from a light chain variable region having the amino acid sequence shown in SEQ ID NO: 3.

In some embodiments, the invention is practiced using an antibody that specifically binds PCSK9 comprising a VH complementary determining region one (CDR1) having the amino acid sequence shown in SEQ ID NO: 4 (SYYMH), SEQ ID NO: 5 (GYTFTSY), or SEQ ID NO: 6 (GYTFT-SYYMH); a VH CDR2 having the amino acid sequence shown in SEQ ID NO: 7 (EISPFGGRTNYNEKFKS) or SEQ ID NO: 8 (SPFGGR), and/or VH CDR3 having the amino acid sequence shown in SEQ ID NO: 9 (ERPLY-ASDL), or a variant thereof having one or more conservative amino acid substitutions in said sequences of CDR1, CDR2, and/or CDR3, wherein the variant retains essentially the same binding specificity as the CDR defined by said sequences. Preferably, the variant comprises up to about ten amino acid substitutions and, more preferably, up to about four amino acid substitutions.

In some embodiments, the invention is practiced using an antibody comprising a VL CDR1 having the amino acid sequence shown in SEQ ID NO: 10 (RASQGISSALA), a CDR2 having the amino acid sequence shown in SEQ ID NO: 11 (SASYRYT), and/or CDR3 having the amino acid sequence shown in SEQ ID NO: 12 (QQRYSLWRT), or a variant thereof having one or more conservative amino acid substitutions in said sequences of CDR1, CDR2, and/or CDR3, wherein the variant retains essentially the same binding specificity as the CDR1 defined by said sequences. Preferably, the variant comprises up to about ten amino acid substitutions and, more preferably, up to about four amino acid substitutions.

In some embodiments, the invention is practiced using an antibody having a heavy chain sequence comprising or consisting of SEQ ID NO: 14, with or without the C-terminal lysine of SEQ ID NO: 14, and a light chain sequence comprising or consisting of SEQ ID NO: 13.

In some embodiments, the invention is practiced using an antibody having a heavy chain variable region comprising or consisting of the amino acid sequence shown in SEQ ID NO: 11 and a light chain variable region comprising or consisting of the amino acid sequence shown in SEQ ID NO: 12.

In some embodiments, the invention is practiced using an antibody that specifically binds PCSK9 comprising a VH complementary determining region one (CDR1) having the amino acid sequence shown in SEQ ID NO: 21 (GYTLT-SYGIS); a VH CDR2 having the amino acid sequence shown in SEQ ID NO: 22 (VSFYNGNTNYAQ) and/or VH CDR3 having the amino acid sequence shown in SEQ ID NO: 23 (CARGYGMDV), or a variant thereof having one or more conservative amino acid substitutions in said sequences of CDR1, CDR2, and/or CDR3, wherein the variant retains essentially the same binding specificity as the CDR defined by said sequences. Preferably, the variant comprises up to about ten amino acid substitutions and, more preferably, up to about four amino acid substitutions.

In some embodiments, the invention is practiced using an antibody comprising a VL CDR1 having the amino acid sequence shown in SEQ ID NO: 24 (TGTSSDVGG-YNSVS), a CDR2 having the amino acid sequence shown in SEQ ID NO: 25 (NSYTSTSMV), and/or CDR3 having the amino acid sequence shown in SEQ ID NO: 26 (EVSNRPS), or a variant thereof having one or more conservative amino acid substitutions in said sequences of CDR1, CDR2, and/or CDR3, wherein the variant retains essentially the same binding specificity as the CDR1 defined by said sequences. Preferably, the variant comprises up to about ten amino acid substitutions and, more preferably, up to about four amino acid substitutions.

In some embodiments, the invention is practiced using an antibody having a heavy chain sequence comprising or consisting of SEQ ID NO: 17, with or without the C-terminal lysine of SEQ ID NO: 17, and a light chain sequence comprising or consisting of SEQ ID NO: 18.

In some embodiments, the invention is practiced using an antibody having a heavy chain variable region comprising or consisting of the amino acid sequence shown in SEQ ID NO: 19 and a light chain variable region comprising or consisting of the amino acid sequence shown in SEQ ID NO: 20.

In some embodiments, the invention is practiced using an antibody that specifically binds PCSK9 comprising a VH complementary determining region one (CDR1) having the amino acid sequence shown in SEQ ID NO: 31 (GFTFN-NYAMN); a VH CDR2 having the amino acid sequence shown in SEQ ID NO: 32 (ISGSGGTTNY ADSVKG) and/or VH CDR3 having the amino acid sequence shown in SEQ ID NO: 33 (DSNWGNFDL), or a variant thereof having one or more conservative amino acid substitutions in said sequences of CDR1, CDR2, and/or CDR3, wherein the variant retains essentially the same binding specificity as the CDR defined by said sequences. Preferably, the variant comprises up to about ten amino acid substitutions and, more preferably, up to about four amino acid substitutions.

In some embodiments, the invention is practiced using an antibody comprising a VL CDR1 having the amino acid sequence shown in SEQ ID NO: 34 (KSSQSVLYRSNNRN-FLG), a CDR2 having the amino acid sequence shown in SEQ ID NO: 35 (WASTRES), and/or CDR3 having the amino acid sequence shown in SEQ ID NO: 36 (QYYTTPYTF), or a variant thereof having one or more conservative amino acid substitutions in said sequences of CDR1, CDR2, and/or CDR3, wherein the variant retains essentially the same binding specificity as the CDR1 defined by said sequences. Preferably, the variant comprises up to about ten amino acid substitutions and, more preferably, up to about four amino acid substitutions.

In some embodiments, the invention is practiced using an antibody having a heavy chain sequence comprising or consisting of SEQ ID NO: 17, with or without the C-terminal lysine of SEQ ID NO: 27, and a light chain sequence comprising or consisting of SEQ ID NO: 28.

In some embodiments, the invention is practiced using an antibody having a heavy chain variable region comprising or consisting of the amino acid sequence shown in SEQ ID NO: 29 and a light chain variable region comprising or consisting of the amino acid sequence shown in SEQ ID NO: 30.

In one embodiment, the antibody or antigen-binding fragment thereof according to the present invention comprises a variable region which comprises framework regions, wherein the framework regions are selected from the group consisting of IgG, IgA, IgM IgE and IgD framework regions. In another embodiment, the antibody or antigen-binding fragment thereof according to the present invention comprises a variable region which comprises framework regions, wherein the framework regions are selected from the group consisting of $IgG_1$, $IgG_2$, $IgG_3$, $IgG_4$ framework regions. The framework regions may be selected from the group consisting of a human, humanized and chimeric framework region In some embodiments, the invention is practiced using an antibody that recognizes a first epitope of PCSK9 that is the same as or overlaps with a second epitope that is recognized by a monoclonal antibody selected from the group consisting of 5A10, which is produced by a hybridoma cell line deposited with the American Type Culture Collection and assigned accession number PTA-8986; 4A5, which is produced by a hybridoma cell line deposited with the American Type Culture Collection and assigned accession number PTA-8985; 6F6, which is produced by a hybridoma cell line deposited with the American Type Culture Collection and assigned accession number PTA-8984, and 7D4, which is produced by a hybridoma cell line deposited with the American Type Culture Collection and assigned accession number PTA-8983. In preferred embodiments, the invention is practiced using the PCSK9 antagonist antibody L1L3 (see, PCT/IB2009/053990, published Mar. 18, 2010 as WO 2010/029513, and U.S. patent application Ser. No. 12/558, 312, published Mar. 18, 2010 as US 2010/0068199).

In some embodiments, a variant of the PCSK9 antagonist antibody as described herein comprises up to about twenty amino acid substitutions and more preferably, up to about eight amino acid substitutions. Preferably, the antibody further comprises an immunologically inert constant region, and/or the antibody has an isotype that is selected from the group consisting of $IgG_2$, $IgG_4$, $IgG_{2\Delta a}$, $IgG_{4\Delta a}$, $IgG_4$ S228P, $IgG_{4\Delta b}$ S228P and $IgG_{4\Delta c}$ S228P. In another preferred embodiment, the constant region is a glycosylated Fc.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), human antibodies, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the PCSK9 antagonist antibody is a monoclonal antibody. The PCSK9 antagonist antibody can also be humanized. In other embodiments, the antibody is human.

In some embodiments, the antibody comprises a modified constant region, such as a constant region that is immunologically inert, that is, having a reduced potential for provoking an immune response. In some embodiments, the constant region is modified as described in Eur. J. Immunol., 1999, 29:2613-2624; PCT Publ. No. WO99/58572; and/or UK Patent Application No. 9809951.8. The Fc can be human $IgG_2$ or human $IgG_4$. The Fc can be human $IgG_2$ containing the mutation A330P331 to S330S331 ($IgG_{2\Delta a}$), in which the amino acid residues are numbered with reference to the wild type IgG2 sequence. Eur. J. Immunol., 1999, 29:2613-2624. In some embodiments, the antibody comprises a constant region of $IgG_4$ comprising the following mutations (Armour et al., 2003, Molecular Immunology 40 585-593): E233F234L235 to P233V234A235 ($IgG_{4\Delta c}$), in which the numbering is with reference to wild type IgG4. In yet another embodiment, the Fc is human $IgG_4$ E233F234L235 to P233V234A235 with deletion G236 ($IgG_{4\Delta b}$). In another embodiment the Fc is any human $IgG_4$ Fc ($IgG_4$, $IgG_{4\Delta b}$ or $IgG_{4\Delta c}$) containing hinge stabilizing mutation S228 to P228 (Aalberse et al., 2002, Immunology 105, 9-19). In another embodiment, the Fc can be a glycosylated Fc.

In some embodiments, the constant region is a glycosylated by mutating the oligosaccharide attachment residue (such as Asn297) and/or flanking residues that are part of the glycosylation recognition sequence in the constant region. In some embodiments, the constant region is a glycosylated for N-linked glycosylation enzymatically. The constant region may be a glycosylated for N-linked glycosylation enzymatically or by expression in a glycosylation deficient host cell.

The PCSK9 antagonist antibody as described herein can also be used in conjunction with other PCSK9 antagonists or PCSK9 receptor antagonists. For example, one or more of the following PCSK9 antagonists may be used: an antisense molecule directed to a PCSK9 (including an anti-sense molecule directed to a nucleic acid encoding PCSK9), a PCSK9 inhibitory compound, and a PCSK9 structural analog. A PCSK9 antagonist antibody can also be used in conjunction with other agents that serve to enhance and/or complement the effectiveness of the agents.

Kits

The invention also provides kits or an article of manufacture comprising a PCSK9 antagonist antibody and instructions for use. Accordingly, in some embodiments, provided is a kit or an article of manufacture, comprising a container, a composition within the container comprising a PCSK9 antagonist antibody, and a package insert containing instructions to deliver as a single administration or plurality of administrations at an initial dose of PCSK9 antagonist antibody of at least about 100 mg, and delivered as a single administration or plurality of administrations at a subsequent dose in an amount that is about the same as the initial dose, or at least half the initial dose after the patient has a LDL-C level at or below about 25, 20, 15, or 10 mg/dL, preferably at or below about 10 mg/dL, wherein all administrations are separated in time from each other by at least about two weeks.

Kits of the invention include one or more containers comprising a PCSK9 antagonist antibody described herein and instructions for use in accordance with the dosing regimen of the invention described herein. Generally, these instructions comprise a description of administration of the PCSK9 antagonist antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

The instructions relating to the use of a PCSK9 antagonist antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a PCSK9 antagonist antibody. The container may further comprise a second pharmaceutically active agent.

Kits may optionally provide additional components such as buffers and interpretive information. Normally, the kit comprises a container and a label or package insert(s) on or associated with the container.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

The present invention is illustrated in further details by the following non-limiting examples. It is understood that other embodiments may be practiced given the general description provided here.

Example 1—Randomized, Placebo-Controlled, Dose-Ranging Study of L1L3 in Statin-Treated Subjects with Hypercholesterolemia This phase 2b study was a 24-week, multicenter, double-blind, placebo-controlled trial randomized hypercholesterolemic subjects with LDL-C≥30 mg/dL on stable statin therapy to Q14d (every 14 days) subcutaneous placebo or L1L3 50 mg, 100 mg or 150 mg; or Q28d (every 28 days) subcutaneous placebo or L1L3 200 mg or 300 mg. Doses of study drug were reduced if LDL-C fell to ≤25 mg/dL. The primary endpoint was the absolute change in LDL-C from baseline to week 12 following treatment with placebo or L1L3.

Methods

Subjects

Enrolled subjects included men and women≥18 years of age with hypercholesterolemia, on stable statin therapy (>6 weeks before screening), with a fasting LDL-C≥30 mg/dL and triglycerides≤400 mg/dL. Subjects were excluded if they had a cardiovascular event during the prior 6 months, received treatment with systemic corticosteroids or a mAb during the prior 6 months, had congestive heart failure (New York Heart Association Class III or IV), poorly controlled diabetes mellitus or hypertension, or diagnosis of cancer, human immunodeficiency virus, or other serious diseases.

Study Design and Conduct

Subjects were randomized using an Interactive Voice Response System (IVRS) in a 1:1:1:1:1:1:1 ratio to Q14d subcutaneous placebo or L1L3 50 mg, 100 mg, or 150 mg; or Q28d subcutaneous placebo or L1L3 200 mg or 300 mg. Follow-up was for 6 to 8 weeks after the last dose of study drug. Cholesterol levels were measured prior to next dose.

Figure 1B:
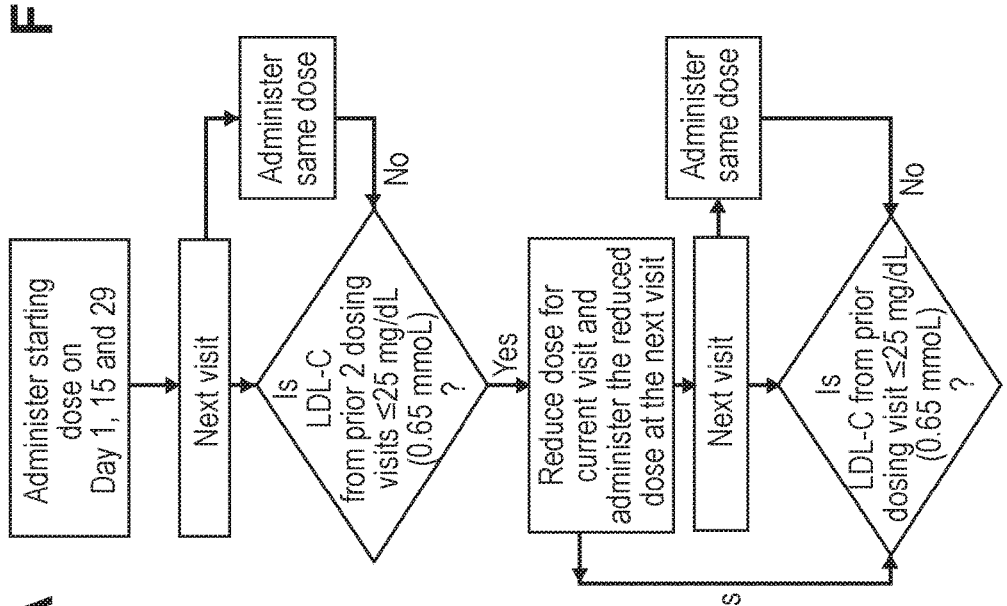

For both the Q14d and Q28d regimens, the L1L3 dose was reduced if LDL-C levels fell to ≤25 mg/dL: the first dose reduction required two consecutive LDL-C levels≤25 mg/dL; all further dose reductions required one LDL-C level≤25 mg/dL. LDL-C data collected at 14 days post-dose provided information on whether dose reduction of L1L3 was required. For the Q14d regimen, dosing was on days 1, 15, 29, 43, 57, 71, 85, 99, 113, 127, 141 and 155. Day 43 was the first opportunity for dose reduction. The L1L3 dose reduction sequence for this cohort was 150 mg→100 mg→50 mg→25 mg→placebo; or 100 mg→50 mg→25 mg→placebo; or 50 mg→25 mg→placebo. For the Q28d regimen, dosing was on days 1, 29, 57, 85, 113, and 141. Day 57 was the first opportunity for dose reduction. The L1L3 dose reduction sequence for this cohort was 300 mg→200 mg→100 mg→50 mg→placebo; or 200 mg→100 mg→50 mg→placebo. See FIG. 1.

Selection of Doses of Study Drug

The doses selected were based on a preliminary population pharmacokinetic/pharmacodynamic (PK/PD) analysis of the lipid-lowering effect of L1L3. PK/PD modeling was performed on data from phase 1 studies, together with interim data from a phase 2a study. The simulations assumed that the distribution of baseline LDL-C and other demographic characteristics in this study were identical to those in the phase 2a study. Doses of 50 mg, 100 mg, and 150 mg subcutaneous (SC) administered Q14d, and 200 mg and 300 mg SC administered Q28d, were selected based on the simulation results.

Administration of Study Drug

Placebo or L1L3 was administered as a single subcutaneous (SC) injection of 2 mL for the Q14D dose group and as two SC injections of 2 mL each for the Q28D dose groups, into a quadrant of the abdomen, over approximately 20 seconds. The subject was blinded to all dosing.

Laboratory Evaluations

The LDL-C values used in the analyses were based on calculated LDL-C reported in the Lipid Research Panel, which utilized the Friedewald calculation. Reflex ultracentrifugation was used for all LDL-C values≤25 mg/dL. Furthermore, if ultracentrifugation results were available for any other time point they were used in the analysis instead of those derived using the Friedewald calculation. The decision was made to use calculated LDL-C rather than reflex ultracentrifugation values for most readings due to the quicker timelines for the receipt of calculated versus ultracentrifugation values. This ensured that data were available at the time of the next subject visit. The 'reflex' approach selected for this study permitted more certainty at the lower end of the range of the observed LDL-C values as a precautionary measure. Moreover, the intention was for the data from this study to be meaningful to the physicians involved in day-to-day practice.

Endpoints and Statistical Analyses

The primary endpoint was the absolute change in LDL-C from baseline to week 12 following treatment with placebo or L1L3, with the primary statistical analysis reporting this change as the placebo-adjusted treatment difference. Secondary endpoints included percentage change in LDL-C, and absolute change and percentage change in non-HDL-C, HDL-C, total cholesterol, and triglycerides, from baseline at 12 and 24 weeks. The average placebo-adjusted change in LDL-C from week 10 to week 12 in the Q28d L1L3 dose groups was assessed as a tertiary endpoint. Safety endpoints included the incidence of AEs, serious AEs, laboratory abnormalities, incidence of anti-drug antibodies (ADAs), and injection site reactions.

L1L3 dose groups were compared with their respective placebo group using a mixed model repeated measures analysis with the dependent variable being change from baseline (in LDL-C for the primary analysis) and including the fixed effect terms treatment group, study visit time point, baseline value, treatment×study visit time point interaction, and baseline value×study visit time point interaction. An unstructured covariance matrix was used for the within-subject errors. The analyses of efficacy data was applied to the full analysis set population, which included all randomized subjects. However, the statistical analyses only incorporated subjects who had a baseline and at least one post-baseline efficacy measurement. The analyses of safety data included all subjects who had received at least one dose of study medication. For all efficacy analyses, subjects remained in the dose group to which they were randomized, regardless of any subsequent dose reductions. Demographic and baseline data were summarized as mean±SD for continuous variables and n (%) for categorical variables.

Laboratory Evaluations

Total cholesterol and triglyceride levels were assayed using standard enzymatic methods. LDL-C was measured by Friedewald and reflex ultracentrifugation for LDL-C levels≤25 mg/dL.

Pharmacokinetic/Pharmacodynamic Modeling

Due to protocol-stipulated dose reductions of L1L3 in this study, a population pharmacokinetic/pharmacodynamic (PK/PD) model was developed using data from seven phase 1 and phase 2 clinical studies to construct a predictor of L1L3 LDL-C lowering in the absence of dose reductions. The population PK/PD dataset consisted of 7574 L1L3 PK observations and 10,177 LDL-C measurements from 674 subjects. The model accounted for dose interruptions or dose reductions implemented in the phase 2 trials, as well as any missed doses that may have occurred during the trials. A two-compartment PK model with parallel first-order and non-linear (Michaelis-Menten) elimination was linked to an indirect PD response model describing LDL-C response. Performance of the final PK/PD model was verified with model diagnostics and visual predictive checks and was found to accurately capture the observed pharmacokinetics of L1L3 and LDL-C response in all studies, as well as in this phase 2b study, which included dose reductions triggered by LDL-C levels 25 mg/dL. Clinical trial simulations using subject demography data from this study were performed with the final PK/PD model to estimate the expected LDL-C response in this phase 2b study assuming no missed doses or dose reductions.

Results

Subject Disposition and Demographics

Overall, 354 subjects were randomized and 351 received treatment with either placebo (n=100) or L1L3 (n=251). The three subjects who were randomized but not treated did not have post-baseline efficacy measurements and so were excluded from further analysis (one each from the placebo, 100-mg, and 150-mg Q14d groups). A total of 299 subjects (85.2% of those treated) completed treatment. The baseline demographics and clinical characteristics of subjects randomized to the various treatment groups were well balanced, including baseline LDL-C levels.

L1L3 Dose Reduction

Overall, 15.7%, 34.7%, 44.0%, and 39.2% of subjects randomized to L1L3 100-mg Q14d, 150-mg Q14d, 200-mg Q28d, and 300-mg Q28d, respectively, had their dose reduced at any time during the study. No dose reductions occurred in the L1L3 50-mg Q14d group. At the week 10 visit (the Q14d dosing time point prior to LDL-C measurement for the primary endpoint), 15.6% of available subjects in the L1L3 100-mg Q14d and 32.5% of subjects in the 150-mg Q14d dose groups had their dose reduced. FIGS. 2A and 2B. At the week 8 visit (the Q28d dosing time point prior to LDL-C measurement for the primary endpoint), 29.5% of available subjects in the L1L3 200-mg Q28d and 34.2% of subjects the 300-mg Q28d group had their dose reduced. FIGS. 2C and 2D.

Efficacy Outcomes—LDL-C

Figure 3:
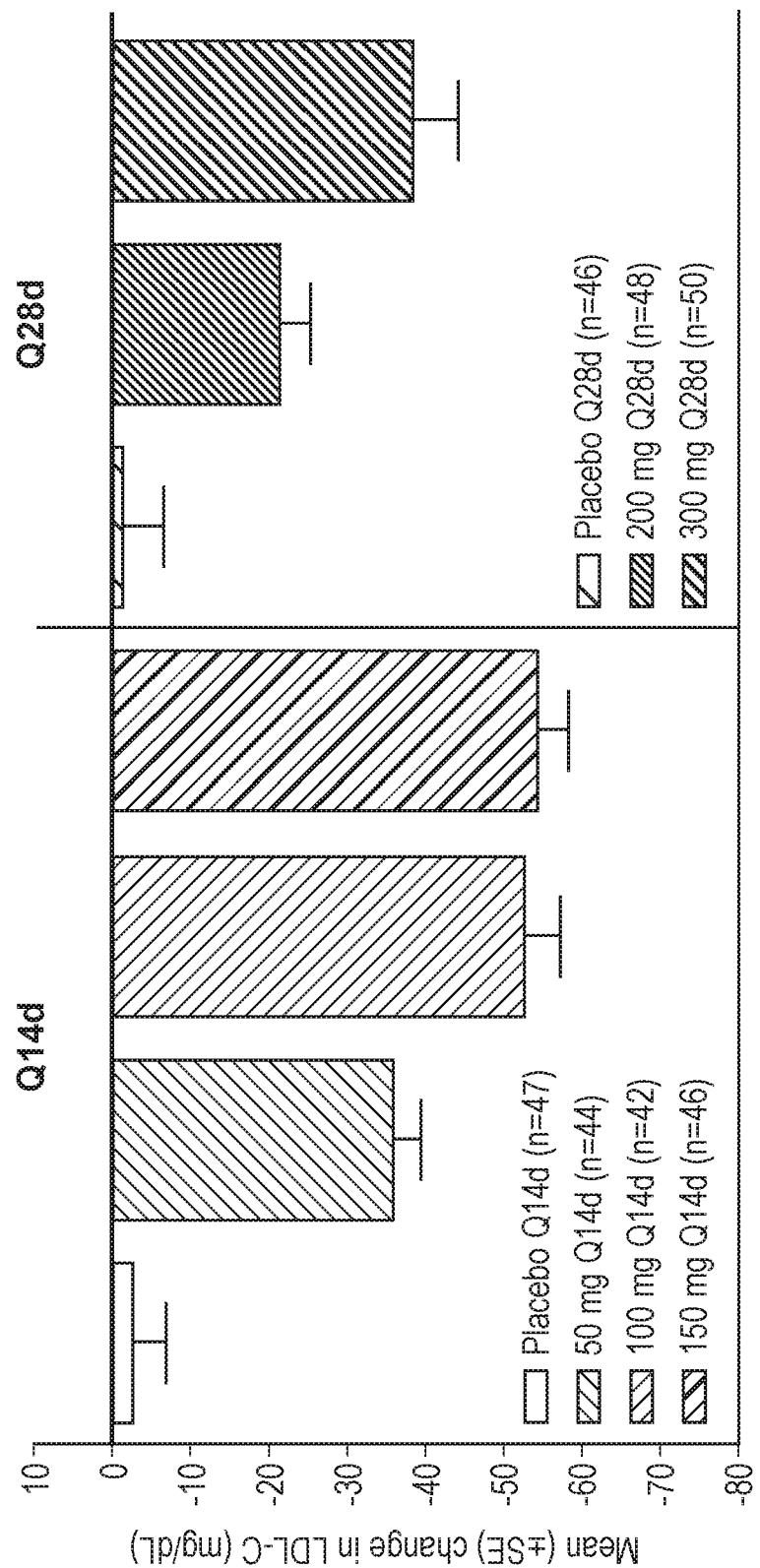

Starting at week 2, Q14d and Q28d L1L3 dose regimens significantly reduced LDL-C levels, and this effect was sustained for the duration of the study. At week 12, the primary endpoint of mean absolute change from baseline in LDL-C was greatest in subjects receiving L1L3 150 mg Q14d (FIG. 3, Table 4).

Figure 4:
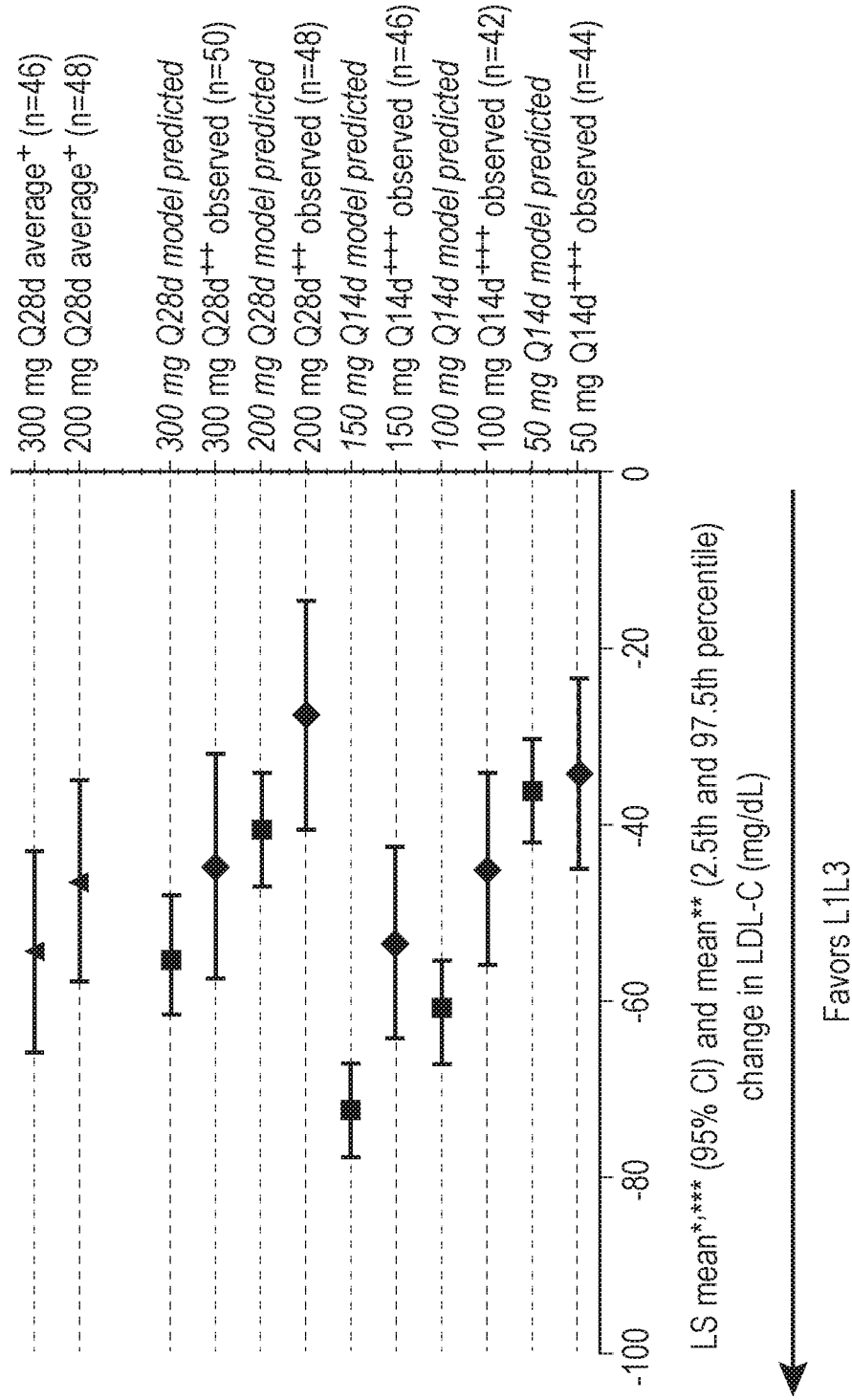

The placebo-adjusted mean change from baseline in LDL-C in all subjects, including those with dose reductions, at week 12 ranged from −34.28 mg/dL to −53.42 mg/dL for those receiving L1L3 Q14d, and from −27.58 mg/dL to −44.85 mg/dL for those receiving L1L3 Q28d (FIG. 4). The PK/PD model-predicted, placebo-adjusted mean change from baseline in LDL-C at week 12 ranged from −36.4 mg/dL for L1L3 50-mg Q14d to −72.2 mg/dL for L1L3 150-mg Q14d (FIG. 4).

Prior to L1L3 dose reductions (up to week 6 for Q14d and week 8 for Q28d), placebo-adjusted mean reductions in LDL-C were greater than those observed at week 12 (FIGS. 5A and 5B). No dose reductions occurred in the 50-mg Q14d group and reductions in LDL-C were similar at weeks 8, 10, and 12 (−34.78 mg/dL, −33.33 mg/dL, and −34.28 mg/dL, respectively; FIG. 5A). For the 100-mg and 150-mg Q14d groups, reductions in LDL-C were maximal at week 6 (−59.85 mg/dL) and 8 (−66.90 mg/dL), respectively (FIG. 5A). For the Q28d regimen, changes were greatest at week 4 for both the 200-mg (−30.91 mg/dL) and the 300-mg (−54.85 mg/dL) groups (FIG. 5B). Reductions in LDL-C were maintained between doses in subjects who received L1L3Q14d but not in those receiving L1L3 Q28d (FIGS. 6A and 6B).

The individual subject LDL-C responses for subjects receiving L1L3 150-mg Q14d who had their dose reduced but did not miss a dose are depicted in FIG. 7, together with the percentage of these subjects on each L1L3 dose at each dosing visit, highlighting the effect of L1L3 dose reduction on LDL-C levels. The detailed dosing schedule and the observed LDL-C are provided below in Table 1:

TABLE 1

| Subject ID | DOSE | ADY | AVISIT | AVAL |
|---|---|---|---|---|
| A | 150 mg, Q14d | −5 | Baseline | 100 |
|  | 150 mg, Q14d | 1 | Baseline | 118 |
|  | 150 mg, Q14d | 15 | Day 15 | 14 |
|  | 150 mg, Q14d | 29 | Day 29 | 23 |
|  | 100 mg, Q14d | 43 | Day 43 | 19 |
|  | 100 mg, Q14d | 57 | Day 57 | 13 |
|  | 50 mg, Q14d | 71 | Day 71 | 18 |
|  | 50 mg, Q14d | 85 | Day 85 | 28 |
|  | 50 mg, Q14d | 102 | Day 99 | 73 |
|  | 50 mg, Q14d | 116 | Day 113 | 51 |
|  | 50 mg, Q14d | 127 | Day 127 | 20 |
|  | 25 mg, Q14d | 141 | Day 141 | 52 |
|  | 25 mg, Q14d | 155 | Day 155 | 82 |
|  | 25 mg, Q14d | 169 | Day 169 | 73 |
|  | 25 mg, Q14d | 176 | Day 169 | 80 |
| B | 150 mg, Q14d | −4 | Baseline | 92 |
|  | 150 mg, Q14d | 1 | Baseline | 106 |
|  | 150 mg, Q14d | 17 | Day 15 | 54 |
|  | 150 mg, Q14d | 29 | Day 29 | 17 |
|  | 150 mg, Q14d | 43 | Day 43 | 9 |
|  | 100 mg, Q14d | 57 | Day 57 | 9 |
|  | 100 mg, Q14d | 72 | Day 71 | 21 |
|  | 50 mg, Q14d | 84 | Day 85 | 40 |
|  | 50 mg, Q14d | 99 | Day 99 | 61 |
|  | 50 mg, Q14d | 113 | Day 113 | 77 |
|  | 50 mg, Q14d | 127 | Day 127 | 50 |
|  | 50 mg, Q14d | 141 | Day 141 | 85 |
|  | 50 mg, Q14d | 155 | Day 155 | 64 |
|  | 50 mg, Q14d | 169 | Day 169 | 54 |
| C | 150 mg, Q14d | −6 | Baseline | 115 |
|  | 150 mg, Q14d | 1 | Baseline | 106 |
|  | 150 mg, Q14d | 15 | Day 15 | 16 |
|  | 150 mg, Q14d | 29 | Day 29 | 7 |
|  | 100 mg, Q14d | 43 | Day 43 | 11 |
|  | 100 mg, Q14d | 57 | Day 57 | 20 |
|  | 50 mg, Q14d | 71 | Day 71 | 9 |
|  | 50 mg, Q14d | 86 | Day 85 | 45 |

TABLE 1-continued

| Subject ID | DOSE | ADY | AVISIT | AVAL |
|---|---|---|---|---|
| | 50 mg, Q14d | 100 | Day 99 | 38 |
| | 50 mg, Q14d | 114 | Day 113 | 26 |
| | 50 mg, Q14d | 127 | Day 127 | 49 |
| | 50 mg, Q14d | 141 | Day 141 | 41 |
| | 50 mg, Q14d | 155 | Day 155 | 60 |
| | 50 mg, Q14d | 157 | Day 155 | 54 |
| | 50 mg, Q14d | 169 | Day 169 | 46 |
| | 50 mg, Q14d | 176 | Day 169 | 74 |
| D | 150 mg, Q14d | −6 | Baseline | 90 |
| | 150 mg, Q14d | 1 | Baseline | 95 |
| | 150 mg, Q14d | 16 | Day 15 | 10 |
| | 150 mg, Q14d | 28 | Day 29 | 8 |
| | 100 mg, Q14d | 45 | Day 43 | 45 |
| | 100 mg, Q14d | 56 | Day 57 | 31 |
| | 100 mg, Q14d | 73 | Day 71 | 44 |
| | 100 mg, Q14d | 86 | Day 85 | 37 |
| | 100 mg, Q14d | 100 | Day 99 | 35 |
| | 100 mg, Q14d | 115 | Day 113 | 49 |
| | 100 mg, Q14d | 128 | Day 127 | 28 |
| | 100 mg, Q14d | 142 | Day 141 | 39 |
| | 100 mg, Q14d | 155 | Day 155 | 28 |
| | 100 mg, Q14d | 168 | Day 169 | 29 |
| E | 150 mg, Q14d | −7 | Baseline | 135 |
| | 150 mg, Q14d | 1 | Baseline | 100 |
| | 150 mg, Q14d | 15 | Day 15 | 39 |
| | 150 mg, Q14d | 30 | Day 29 | 37 |
| | 150 mg, Q14d | 44 | Day 43 | 30 |
| | 150 mg, Q14d | 58 | Day 57 | 28 |
| | 150 mg, Q14d | 72 | Day 71 | 20 |
| | 150 mg, Q14d | 84 | Day 85 | 25 |
| | 100 mg, Q14d | 99 | Day 99 | 39 |
| | 100 mg, Q14d | 113 | Day 113 | 34 |
| | 100 mg, Q14d | 129 | Day 127 | 33 |
| | 100 mg, Q14d | 141 | Day 141 | 39 |
| | 100 mg, Q14d | 155 | Day 155 | 39 |
| | 100 mg, Q14d | 156 | Day 155 | 30 |
| | 100 mg, Q14d | 169 | Day 169 | 43 |
| F | 150 mg, Q14d | −7 | Baseline | 85 |
| | 150 mg, Q14d | 1 | Baseline | 71 |
| | 150 mg, Q14d | 15 | Day 15 | 41 |
| | 150 mg, Q14d | 29 | Day 29 | 27 |
| | 150 mg, Q14d | 43 | Day 43 | 31 |
| | 150 mg, Q14d | 57 | Day 57 | 17 |
| | 100 mg, Q14d | 71 | Day 71 | 14 |
| | 100 mg, Q14d | 85 | Day 85 | 20 |
| | 50 mg, Q14d | 113 | Day 113 | 50 |
| | 50 mg, Q14d | 127 | Day 127 | 35 |
| | 50 mg, Q14d | 140 | Day 141 | 42 |
| | 50 mg, Q14d | 155 | Day 155 | 53 |
| | 50 mg, Q14d | 169 | Day 169 | 52 |
| G | 150 mg, Q14d | −7 | Baseline | 97 |
| | 150 mg, Q14d | 1 | Baseline | 111 |
| | 150 mg, Q14d | 15 | Day 15 | 30 |
| | 150 mg, Q14d | 29 | Day 29 | 33 |
| | 150 mg, Q14d | 43 | Day 43 | 19 |
| | 150 mg, Q14d | 57 | Day 57 | 20 |
| | 100 mg, Q14d | 71 | Day 71 | 19 |
| | 100 mg, Q14d | 85 | Day 85 | 19 |
| | 50 mg, Q14d | 99 | Day 99 | 37 |
| | 50 mg, Q14d | 113 | Day 113 | 59 |
| | 50 mg, Q14d | 127 | Day 127 | 50 |
| | 50 mg, Q14d | 141 | Day 141 | 46 |
| | 50 mg, Q14d | 155 | Day 155 | 61 |
| | 50 mg, Q14d | 156 | Day 155 | 57 |
| | 50 mg, Q14d | 169 | Day 169 | 72 |
| H | 150 mg, Q14d | −7 | Baseline | 108 |
| | 150 mg, Q14d | 1 | Baseline | 123 |
| | 150 mg, Q14d | 15 | Day 15 | 40 |
| | 150 mg, Q14d | 29 | Day 29 | 27 |
| | 150 mg, Q14d | 43 | Day 43 | 23 |
| | 150 mg, Q14d | 57 | Day 57 | 21 |
| | 100 mg, Q14d | 71 | Day 71 | 21 |
| | 100 mg, Q14d | 85 | Day 85 | 31 |
| | 100 mg, Q14d | 101 | Day 99 | 35 |
| | 100 mg, Q14d | 113 | Day 113 | 26 |
| | 50 mg, Q14d | 127 | Day 127 | 26 |
| | 50 mg, Q14d | 141 | Day 141 | 49 |
| | 50 mg, Q14d | 155 | Day 155 | 61 |
| | 50 mg, Q14d | 157 | Day 155 | 47 |
| | 50 mg, Q14d | 170 | Day 169 | 66 |
| I | 150 mg, Q14d | −7 | Baseline | 92 |
| | 150 mg, Q14d | 1 | Baseline | 116 |
| | 150 mg, Q14d | 15 | Day 15 | 27 |
| | 150 mg, Q14d | 29 | Day 29 | 30 |
| | 150 mg, Q14d | 43 | Day 43 | 18 |
| | 150 mg, Q14d | 57 | Day 57 | 17 |
| | 100 mg, Q14d | 71 | Day 71 | 26 |
| | 100 mg, Q14d | 86 | Day 85 | 22 |
| | 50 mg, Q14d | 98 | Day 99 | 23 |
| | 50 mg, Q14d | 112 | Day 113 | 35 |
| | 50 mg, Q14d | 126 | Day 127 | 50 |
| | 50 mg, Q14d | 140 | Day 141 | 46 |
| | 50 mg, Q14d | 154 | Day 155 | 58 |
| | 50 mg, Q14d | 168 | Day 169 | 57 |
| J | 150 mg, Q14d | −7 | Baseline | 105 |
| | 150 mg, Q14d | 15 | Day 15 | 50 |
| | 150 mg, Q14d | 30 | Day 29 | 20 |
| | 150 mg, Q14d | 45 | Day 43 | 20 |
| | 100 mg, Q14d | 58 | Day 57 | 15 |
| | 100 mg, Q14d | 72 | Day 71 | 20 |
| | 50 mg, Q14d | 87 | Day 85 | 28 |
| | 50 mg, Q14d | 100 | Day 99 | 48 |
| | 50 mg, Q14d | 142 | Day 141 | 70 |
| | 50 mg, Q14d | 155 | Day 155 | 66 |
| | 50 mg, Q14d | 158 | Day 155 | 33 |
| | 50 mg, Q14d | 169 | Day 169 | 90 |
| K | 150 mg, Q14d | −6 | Baseline | 104 |
| | 150 mg, Q14d | 1 | Baseline | 97 |
| | 150 mg, Q14d | 16 | Day 15 | 61 |
| | 150 mg, Q14d | 30 | Day 29 | 13 |
| | 150 mg, Q14d | 44 | Day 43 | 14 |
| | 100 mg, Q14d | 58 | Day 57 | 13 |
| | 100 mg, Q14d | 73 | Day 71 | 17 |
| | 50 mg, Q14d | 86 | Day 85 | 11 |
| | 50 mg, Q14d | 99 | Day 99 | 28 |
| | 25 mg, Q14d | 114 | Day 113 | 38 |
| | 25 mg, Q14d | 128 | Day 127 | 49 |
| | 25 mg, Q14d | 142 | Day 141 | 62 |
| | 25 mg, Q14d | 155 | Day 155 | 51 |
| | 25 mg, Q14d | 157 | Day 155 | 36 |
| | 25 mg, Q14d | 170 | Day 169 | 69 |
| L | 150 mg, Q14d | −7 | Baseline | 87 |
| | 150 mg, Q14d | 1 | Baseline | 101 |
| | 150 mg, Q14d | 14 | Day 15 | 18 |
| | 150 mg, Q14d | 29 | Day 29 | 24 |
| | 100 mg, Q14d | 43 | Day 43 | 29 |
| | 100 mg, Q14d | 57 | Day 57 | 31 |
| | 100 mg, Q14d | 71 | Day 71 | 48 |
| | 100 mg, Q14d | 85 | Day 85 | 53 |
| | 100 mg, Q14d | 98 | Day 99 | 31 |
| | 50 mg, Q14d | 113 | Day 113 | 59 |
| | 50 mg, Q14d | 127 | Day 127 | 62 |
| | 50 mg, Q14d | 141 | Day 141 | 73 |
| | 50 mg, Q14d | 155 | Day 155 | 69 |
| | 50 mg, Q14d | 157 | Day 155 | 52 |
| | 50 mg, Q14d | 170 | Day 169 | 72 |

AVAL is the variable for observed LDL-C,
AVISIT is the visit description,
ADY is analysis relative day Efficacy Outcomes—Other Lipids Starting at week 2, L1L3 therapy produced dose-related reductions in non-HDL-C, which were maintained in the Q14d 50 mg group throughout the 24-week treatment period. For the Q14d 100-mg and 150-mg groups, change from baseline in non-HDL-C diminished after weeks 8-10, which may have been due to dose reductions. The mean percent changes from baseline in non-HDL-C at week 12 are provided in Table 2.

TABLE 2

Baseline characteristics of all subjects randomized to placebo or L1L3, Q14d or Q28d

| | Q14d | | | | Q28d | | |
|---|---|---|---|---|---|---|---|
| | Placebo* | L1L3 | | | Placebo | L1L3 | |
| Variable | (n = 50) | 50 mg (n = 50) | 100 mg* (n = 52) | 150 mg* (n = 50) | (n = 51) | 200 mg (n = 50) | 300 mg (n = 51) |
| Age (years) | 60.5 ± 9.84 | 59.1 ± 11.26 | 61.9 ± 9.58 | 61.4 ± 9.75 | 58.4 ± 11.62 | 60.3 ± 9.64 | 60.2 ± 8.17 |
| Male gender | 25 (50.0) | 24 (48.0) | 26 (50.0) | 21 (42.0) | 29 (56.9) | 19 (38.0) | 25 (49.0) |
| Race | | | | | | | |
| White | 39 (78.0) | 33 (66.0) | 37 (71.2) | 36 (72.0) | 35 (68.6) | 39 (78.0) | 41 (80.4) |
| Black | 9 (18.0) | 15 (30.0) | 12 (23.1) | 10 (20.0) | 14 (27.5) | 9 (18.0) | 8 (15.7) |
| Asian and other | 2 (4.0) | 2 (4.0) | 3 (5.8) | 4 (8.0) | 2 (3.9) | 2 (4.0) | 2 (3.9) |
| Weight (kg) | 91.1 ± 21.76 | 91.4 ± 23.55 | 90.2 ± 21.27 | 90.4 ± 16.82 | 90.5 ± 21.27 | 88.3 ± 23.89 | 88.5 ± 19.22 |
| BMI (kg/m$^2$) | 32.3 ± 7.37 | 31.9 ± 7.53 | 31.8 ± 7.10 | 31.9 ± 5.69 | 30.7 ± 6.36 | 31.3 ± 6.66 | 30.7 ± 6.39 |
| LDL-C (mg/dL) | 108.7 ± 31.50† | 107.9 ± 20.17 | 113.4 ± 25.66† | 105.8 ± 17.98† | 118.8 ± 44.77 | 105.7 ± 23.21 | 104.7 ± 22.09 |
| TC (mg/dL) | 188.8 ± 35.12† | 186.0 ± 34.85 | 194.5 ± 33.72† | 188.9 ± 25.30† | 198.4 ± 45.28 | 185.1 ± 29.56 | 178.9 ± 29.92 |
| TG (mg/dL) | 124.0 (82.0, 180.0)† | 109.0 (71.0, 155.0) | 135.0 (96.0, 176.0)† | 138.0 (100.0, 172.0)† | 109.0 (80.0, 169.0) | 122.5 (89.0, 158.0) | 113.0 (79.0, 149.0) |
| Non-HDL-C (mg/dL) | 136.5 ± 33.79† | 134.0 ± 35.90 | 143.4 ± 31.26† | 136.0 ± 23.44† | 145.8 ± 45.26 | 133.2 ± 26.61 | 129.8 ± 28.56 |
| HDL-C (mg/dL) | 52.3 ± 14.09† | 52.1 ± 15.90 | 51.2 ± 13.67† | 52.9 ± 14.05† | 52.6 ± 11.57 | 51.9 ± 14.36 | 49.2 ± 13.20 |
| PCSK9 (ng/mL) | 305.0 (260.0, 344.0) | 298.0 (257.0, 329.0) | 313.5 (238.0, 363.0) | 338.5 (308.0, 399.5) | 301.0 (233.0, 349.0) | 317.0 (271.0, 378.0) | 299.0 (252.0, 364.0) |
| Baseline statin dose | | | | | | | |
| Low‡ | 26 (52.0) | 25 (50.0) | 22 (42.3) | 20 (40.0) | 28 (54.9) | 23 (46.0)† | 22 (43.1)† |
| High§ | 24 (48.0) | 25 (50.0) | 30 (57.7) | 30 (60.0) | 23 (45.1) | 26 (52.0)† | 28 (54.9)† |

Values are mean ± SD, median (25$^{th}$, 75$^{th}$ percentile), n (%), or n = number of subjects randomized.
*Three subjects (one each from the placebo, 100-mg, and 150-mg Q14d groups) were randomized but did not receive treatment.
†Data are missing for one subject in each of these groups. ‡ Low statin dose defined as atorvastatin ≤10 mg, rosuvastatin ≤5 mg, simvastatin ≤20 mg, pravastatin ≤40 mg, lovastatin ≤80 mg, and fluvastatin ≤40 mg daily. § High statin dose defined as all higher doses of these statins.
BMI = body mass index;
F = female;
HDL-C = high-density lipoprotein cholesterol;
LDL-C = low-density lipoprotein cholesterol;
M = male;
SD = standard deviation;
TC = total cholesterol;
TG = triglycerides.

L1L3 increased HDL-C at weeks 12 (See Table 3) and 24. At week 12, the mean percent change from baseline in HDL-C ranged from +2.65% (150 mg) to +3.89% (50 mg) for subjects receiving L1L3 Q14d (versus +0.82% for Q14d placebo), and from +6.90% (300 mg) to +7.06% (200 mg) for those receiving L1L3 Q28d (versus −0.41% for Q28d placebo).

TABLE 3

Lipid efficacy outcomes from baseline at week 12 in subjects randomized to placebo or L1L3, Q14d or Q28d

| | Q14d | | | | Q28d | | |
|---|---|---|---|---|---|---|---|
| | Placebo | L1L3 | | | Placebo | L1L3 | |
| Variable | (n = 47) | 50 mg (n = 43-44) | 100 mg (n = 42-44) | 150 mg (n = 46) | (n = 46-47) | 200 mg (n = 48) | 300 mg (n = 50) |
| LDL-C | | | | | | | |
| Mean (SD) change, mg/dL | −2.8 (29.24) | −35.4 (26.58) | −52.3 (31.26) | −54.2 (26.98) | −1.3 (37.16) | −21.3 (28.03) | −38.3 (41.26) |
| Mean (95% | — | −34.28 (−45.06, | −45.07 (−55.93, | −53.42 (−64.14, | — | −27.58 (−40.49, | −44.85 (−57.65, |

TABLE 3-continued

Lipid efficacy outcomes from baseline at week 12 in subjects randomized to placebo or L1L3, Q14d or Q28d

| | | Q14d | | | | Q28d | |
|---|---|---|---|---|---|---|---|
| | | | L1L3 | | | | L1L3 |
| Variable | Placebo (n = 47) | 50 mg (n = 43-44) | 100 mg (n = 42-44) | 150 mg (n = 46) | Placebo (n = 46-47) | 200 mg (n = 48) | 300 mg (n = 50) |
| CI) placebo-adjusted change, mg/dL | | −23.50) | −34.21) | −42.70) | | −14.67) | −32.05) |
| P-value | — | <0.001 | <0.001 | <0.001 | — | <0.001 | <0.001 |
| Mean (SD) percent change, % | 0.57 (25.45) | −33.65 (23.31) | −44.87 (23.43) | −52.02 (24.65) | 3.34 (25.04) | −19.48 (26.60) | −33.26 (35.18) |
| Mean (95% CI) placebo-adjusted percent change, % | — | −35.00 (−44.91, −25.10) | −42.32 (−52.30, −32.33) | −53.12 (−62.97, −43.27) | — | −26.96 (−38.25, −15.67) | −41.13 (−52.32, −29.94) |
| P-value | | <0.001 | <0.001 | <0.001 | | <0.001 | <0.001 |
| Total cholesterol | | | | | | | |
| Mean (SD) change, mg/dL | −5.6 (29.58) | −35.8 (24.73) | −52.7 (32.67) | −58.6 (32.90) | −0.4 (40.0) | −19.5 (27.39) | −37.6 (43.58) |
| Mean (95% CI) placebo-adjusted change, mg/dL | — | −29.70 (−41.78, −17.63) | −42.45 (−54.49, −30.40) | −55.59 (−67.56, −43.63) | — | −24.81 (−38.94, −10.68) | −45.58 (−59.75, −31.42) |
| P-value | | <0.001 | <0.001 | <0.001 | | <0.001 | <0.001 |
| Mean (SD) percent change, % | −2.35 (14.41) | −18.96 (12.30) | −26.45 (14.94) | −31.64 (18.01) | 1.24 (16.62) | −10.51 (15.32) | −19.44 (22.05) |
| Mean (95% CI) placebo-adjusted percent change, % | — | −15.74 (−22.13, −9.34) | −22.15 (−28.53, −15.77) | −30.11 (−36.45, −23.77) | — | −13.78 (−20.89, −6.67) | −23.78 (−30.91, −16.66) |
| P-value | | <0.001 | <0.001 | <0.001 | | <0.001 | <0.001 |
| HDL-C | | | | | | | |
| Mean (SD) change, mg/dL | 0.1 (6.99) | 1.7 (7.08) | 2.1 (7.45) | 1.0 (7.47) | −1.0 (7.43) | 3.4 (9.15) | 3.1 (7.71) |
| Mean (95% CI) placebo-adjusted change, mg/dL | — | 1.64 (−1.35, 4.63) | 1.73 (−1.24, 4.71) | 0.53 (−2.43, 3.50) | — | 4.45 (1.21, 7.70) | 3.86 (0.63, 7.09) |
| P-value | — | 0.281 | 0.251 | 0.724 | — | 0.007 | 0.019 |
| Mean (SD) percent change, % | 0.82 (14.57) | 3.89 (14.98) | 3.85 (13.22) | 2.65 (12.74) | −0.41 (14.00) | 7.06 (17.08) | 6.9 (16.88) |
| Mean (95% CI) placebo-adjusted percent change, % | — | 3.41 (−2.38, 9.21) | 2.62 (−3.14, 8.38) | 1.35 (−4.40, 7.10) | — | 7.66 (1.33, 13.99) | 6.52 (0.22, 12.83) |
| P-value | | 0.246 | 0.371 | 0.643 | | 0.018 | 0.043 |
| Triglycerides | | | | | | | |
| Median (Q1, Q3) change, mg/dL | −18.0 (−52.0, 13.0) | −12.0 (−40.0, 9.0) | −13.0 (−43.5, 10.0) | −21.0 (−43.0, 9.0) | 5.0 (−23.0, 32.0) | −9.0 (−35.0, 11.5) | −14.5 (−51.0, 13.0) |
| Median (Q1, Q3) percent change, % | −14.52 (−32.5, 11.76) | −14.08 (−28.46, 7.82) | −14.77 (−35.62, 10.68) | −18.58 (−34.48, 4.95) | 3.73 (−11.26, 31.07) | −7.60 (−24.21, 14.65) | −13.78 (−32.71, 11.25) |
| Non-HDL-C | | | | | | | |
| Mean (SD) change, mg/dL | −5.7 (26.92) | −37.5 (22.40) | −55.0 (32.75) | −59.6 (33.23) | 0.6 (38.04) | −22.9 (29.05) | −40.7 (44.91) |

TABLE 3-continued

Lipid efficacy outcomes from baseline at week 12 in subjects randomized to placebo or L1L3, Q14d or Q28d

| | | Q14d | | | | Q28d | |
|---|---|---|---|---|---|---|---|
| | | L1L3 | | | | L1L3 | |
| Variable | Placebo (n = 47) | 50 mg (n = 43-44) | 100 mg (n = 42-44) | 150 mg (n = 46) | Placebo (n = 46-47) | 200 mg (n = 48) | 300 mg (n = 50) |
| Mean (95% CI) placebo-adjusted change, mg/dL | — | −31.07 (−42.56, −19.58) | −44.09 (−55.56, −32.62) | −55.60 (−66.99, −44.20) | — | −29.34 (−43.54, −15.13) | −48.55 (−62.70, −34.40) |
| P-value | — | <0.001 | <0.001 | <0.001 | — | <0.001 | <0.001 |
| Mean (SD) percent change, % | −2.28 (20.23) | −28.34 (15.84) | −38.52 (21.36) | −44.86 (24.26) | 2.76 (20.34) | −17.30 (22.32) | −28.68 (30.86) |
| Mean (95% CI) placebo-adjusted percent change, % | — | −24.59 (−33.26, −15.91) | −33.22 (−41.88, −24.56) | −42.80 (−51.41, −34.20) | — | −22.58 (−32.39, −12.76) | −34.67 (−44.45, −24.90) |
| P-value | — | <0.001 | <0.001 | <0.001 | — | <0.001 | <0.001 |

HDL-C = high-density lipoprotein cholesterol;
LDL-C = low-density lipoprotein cholesterol;
M = male;
SD = standard deviation;
TC = total cholesterol;
TG = triglycerides.

Safety Outcomes

The percentage of subjects reporting AEs (adverse events) or serious AEs (SAEs) was similar across placebo- and L1L3-treatment groups. See Table 4.

TABLE 4

Percentage of subjects with all-causality and treatment-related* AEs following randomization to placebo or L1L3 doses Q14d, or placebo or L1L3 doses Q28d.

| | | Q14d | | | | Q28d | |
|---|---|---|---|---|---|---|---|
| | | L1L3 | | | | L1L3 | |
| Variable | Placebo (n = 49) | 50 mg (n = 50) | 100 mg (n = 51) | 150 mg (n = 49) | Placebo (n = 51) | 200 mg (n = 50) | 300 mg (n = 51) |
| AEs | 83.7 [28.6] | 74.0 [24.0] | 84.3 [31.4] | 81.6 [36.7] | 80.4 [15.7] | 90.0 [28.0] | 82.4 [33.3] |
| Serious AEs | 14.3 [0] | 8.0 [0] | 3.9 [0] | 8.2 [2.0] | 3.9 [0] | 10.0 [0] | 7.8 [0] |
| Discontinuation of treatment due to AE | 2.0 [0] | 2.0 [2.0] | 3.9 [0] | 10.2 [8.2] | 0 | 0 | 9.8 [3.9] |
| Most frequent AEs (≥~10%) | | | | | | | |
| Nasopharyngitis | 12.2 [0] | 16.0 [0] | 13.7 [0] | 10.2 [0] | 13.7 [0] | 12.0 [0] | 11.8 [0] |
| Upper respiratory tract infection | 14.3 [0] | 8.0 [0] | 9.8 [0] | 6.1 [2.0†] | 17.6 [0] | 10.0 [2.0] | 5.9 [0] |
| Diarrhea | 8.2 [0] | 6.0 [0] | 7.8 [3.9] | 10.2 [2.0] | 3.9 [0] | 4.0 [0] | 7.8 [0] |
| Urinary tract infection | 6.1 [0] | 2.0 [0] | 9.8 [0] | 8.2 [2.0] | 2.0 [0] | 4.0 [0] | 3.9 [0] |
| Bronchitis | 8.2 [0] | 4.0 [0] | 5.9 [0] | 10.2 [0] | 5.9 [0] | 6.0 [0] | 3.9 [0] |
| Arthralgia | 4.1 [0] | 0 | 11.8 [2.0] | 8.2 [0] | 5.9 [0] | 0 | 3.90 [0] |
| Injection site erythema | 4.1 [4.1] | 4.0 [2.0] | 7.8 [5.9] | 10.2 [10.2] | 0 | 8.0 [8.0] | 9.8 [7.8] |

TABLE 4-continued

Percentage of subjects with all-causality and treatment-related* AEs following randomization to placebo or L1L3 doses Q14d, or placebo or L1L3 doses Q28d.

| | Q14d | | | | Q28d | | |
| --- | --- | --- | --- | --- | --- | --- | --- |
| | | L1L3 | | | | L1L3 | |
| Variable | Placebo (n = 49) | 50 mg (n = 50) | 100 mg (n = 51) | 150 mg (n = 49) | Placebo (n = 51) | 200 mg (n = 50) | 300 mg (n = 51) |
| Injection site reaction | 2.0 [2.0] | 6.0 [6.0] | 2.0 [0] | 12.2 [8.2] | 2.0 [2.0] | 2.0 [2.0] | 9.8 [7.8] |
| Gastroesophageal reflux disease | 2.0 [0] | 0 | 9.8 [0] | 4.1 [0] | 2.0 [0] | 2.0 [0] | 0 |
| Cough | 10.2 [0] | 4.0 [0] | 2.0 [0] | 4.1 [0] | 2.0 [0] | 2.0 [0] | 2.0 [0] |
| Anemia | 2.0 [2.0] | 0 | 9.8 [0] | 4.1 [0] | 0 | 4.0 [0] | 0 |

Values are % of subjects with all-causality [treatment-related] AEs or n = number of subjects treated.
*Investigator-determined treatment relatedness.
†Specified as viral upper respiratory tract infection.

Irrespective of investigator-determined causality, nasopharyngitis and upper respiratory tract infections were the most frequently reported all-causality AEs and showed a similar incidence in the placebo and L1L3 groups. See Table 4. The most frequently reported treatment-related AEs were injection site events, of which the most common was injection site erythema (Table 4). One L1L3 150-mg Q14d subject experienced two concurrent SAEs that were considered treatment-related: a viral upper respiratory tract infection and severe dyspnea. One subject—a 74-year-old male in the L1L3 50-mg Q14d treatment group—died from an accidental head injury following a fall during the follow-up period (57 days after last dose). This death was not considered related to study treatment.

Overall, 14 subjects (4.0%) discontinued treatment due to all-causality AEs, with more subjects in the higher than the lower dose L1L3 groups stopping treatment (Table 3); there was no pattern or trend in the types of AEs that led to discontinuation of treatment. Seven subjects discontinued treatment due to treatment-related AEs (Table 2). These were: from the 50-mg Q14d group, urticaria (n=1); from the 150-mg Q14d group, asthenia and fatigue, viral upper respiratory tract infection, renal impairment, and lip swelling (n=1 for each AE); and from the 300-mg Q28d group, abdominal pain and injection site reaction (n=1 for each AE).

Two subjects experienced non-serious adverse events (AEs) of memory loss: one (0.02%) in the L1L3 100-mg Q14d group (considered treatment-related) and one (0.02%) in the L1L3 300-mg Q28d group (not considered treatment-related). Neither subject had their L1L3 doses reduced due to persistent LDL-C values≤25 mg/dL nor discontinued treatment. The subject receiving L1L3 100-mg Q14d had a minimum LDL-C value of 43 mg/dL recorded. In addition to being on concomitant statin therapy with labelling indicating that it can cause amnesia, this subject was also receiving zolpidem tartrate, which has been associated with amnesia. This subject also reported a serious AE of retinal detachment. The subject receiving L1L3 300-mg Q28d had LDL-C levels of 18 mg/dL on day 15, 17 mg/dL on day 43, and 7 mg/dL on day 71. This subject was also receiving concomitant statin therapy with labelling indicating that it can cause amnesia.

The incidence of AEs was similar among L1L3-treated subjects who had an LDL-C≤25 mg/dL during the study compared with those who did not (~80-90% across most groups), and no trend was seen in the type of AEs reported between the two subgroups (Table 5). No placebo subjects had an LDL-C≤25 mg/dL. The most frequently reported AEs were nasopharyngitis and injection site erythema in subjects who had an LDL-C≤25 mg/dL, and nasopharyngitis and upper respiratory tract infections in those whose LDL-C levels remained >25 mg/dL (Table 5).

TABLE 5

Incidence of all-causality AEs in subjects randomized to placebo or L1L3 doses Q14d, or placebo or L1L3 doses Q28d, with or without an LDL-C ≤25 mg/dL.

| | Subjects with LDL-C ≤25 mg/dL | | | | | | |
| --- | --- | --- | --- | --- | --- | --- | --- |
| | Q14d | | | | Q28d | | |
| | | L1L3 | | | | L1L3 | |
| Variable | Placebo (n = 0) | 50 mg (n = 3) | 100 mg (n = 21) | 150 mg (n = 25) | Placebo (n = 0) | 200 mg (n = 34) | 300 mg (n = 38) |
| AEs | 0 | 1 (33.3) | 18 (85.7) | 20 (80.0) | 0 | 30 (88.2) | 31 (81.6) |
| Most frequent AEs (≥~10%)† | | | | | | | |
| Nasopharyngitis | 0 | 0 | 3 (14.3) | 2 (8.0) | 0 | 5 (14.7) | 3 (7.9) |
| Injection site erythema | 0 | 0 | 2 (9.5) | 3 (12.0) | 0 | 4 (11.8) | 3 (7.9) |

TABLE 5-continued

Incidence of all-causality AEs in subjects randomized to placebo or L1L3
doses Q14d, or placebo or L1L3 doses Q28d, with or without an LDL-C ≤25 mg/dL.

| | | | | | | | |
|---|---|---|---|---|---|---|---|
| Upper respiratory tract infection | 0 | 0 | 3 (14.3) | 0 | 0 | 5 (14.7) | 2 (5.3) |
| Diarrhea | 0 | 0 | 2 (9.5) | 2 (8.0) | 0 | 2 (5.9) | 4 (10.5) |
| Bronchitis | 0 | 0 | 0 | 4 (16.0) | 0 | 3 (8.8) | 2 (5.3) |
| Sinusitis | 0 | 0 | 3 (14.3) | 2 (8.0) | 0 | 2 (5.9) | 0 |
| Vomiting | 0 | 0 | 1 (4.8) | 3 (12.0) | 0 | 2 (5.9) | 1 (2.6) |
| Arthralgia | 0 | 0 | 3 (14.3) | 3 (12.0) | 0 | 0 | 0 |
| Back pain | 0 | 0 | 2 (9.5) | 0 | 0 | 4 (11.8) | 0 |
| Fall | 0 | 0 | 3 (14.3) | 1 (4.0) | 0 | 1 (2.9) | 1 (2.6) |
| Contusion | 0 | 0 | 3 (14.3) | 0 | 0 | 0 | 0 |
| Depression | 0 | 1 (33.3) | 1 (4.8) | 0 | 0 | 0 | 0 |
| Osteoarthritis | 0 | 1 (33.3) | 0 | 0 | 0 | 0 | 1 (2.6) |
| Benign prostatic hyperplasia | 0 | 1 (33.3) | 0 | 0 | 0 | 0 | 0 |
| Cerebrovascular accident | 0 | 1 (33.3) | 0 | 0 | 0 | 0 | 0 |
| Malaise | 0 | 1 (33.3) | 0 | 0 | 0 | 0 | 0 |

| | Subjects with LDL-C ≤25 mg/dL | | | | | | |
|---|---|---|---|---|---|---|---|
| | Q14d | | | | Q28d | | |
| | | L1L3 | | | | L1L3 | |
| Variable | Placebo (n = 49) | 50 mg (n = 47) | 100 mg (n = 30) | 150 mg (n = 24) | Placebo (n = 51) | 200 mg (n = 16) | 300 mg (n = 13) |
| AEs | 41 (83.7) | 36 (76.6) | 25 (83.3) | 20 (83.3) | 41 (80.4) | 15 (93.8) | 11 (84.6) |
| Most frequent AEs (≥~10%)‡ | | | | | | | |
| Nasopharyngitis | 6 (12.2) | 8 (17.0) | 4 (13.3) | 3 (12.5) | 7 (13.7) | 1 (6.3) | 3 (23.1) |
| Upper respiratory tract infection | 7 (14.3) | 4 (8.5) | 2 (6.7) | 3 (12.5) | 9 (17.6) | 0 | 1 (7.7) |
| Diarrhea | 4 (8.2) | 3 (6.4) | 2 (6.7) | 3 (12.5) | 2 (3.9) | 0 | 0 |
| Urinary tract infection | 3 (6.1) | 1 (2.1) | 5 (16.7) | 2 (8.3) | 1 (2.0) | 2 (12.5) | 0 |
| Bronchitis | 4 (8.2) | 2 (4.3) | 3 (10.0) | 1 (4.2) | 3 (5.9) | 0 | 0 |
| Injection site pain | 4 (8.2) | 4 (8.5) | 0 | 0 | 2 (3.9) | 0 | 2 (15.4) |
| Arthralgia | 2 (4.1) | 0 | 3 (10.0) | 1 (4.2) | 3 (5.9) | 0 | 2 (15.4) |
| Headache | 2 (4.1) | 2 (4.3) | 0 | 1 (4.2) | 1 (2.0) | 3 (18.8) | 2 (15.4) |
| Injection site reaction | 1 (2.0) | 3 (6.4) | 0 | 4 (16.7) | 1 (2.0) | 0 | 2 (15.4) |
| Injection site erythema | 2 (4.1) | 2 (4.3) | 2 (6.7) | 2 (8.3) | 0 | 0 | 2 (15.4) |
| Cough | 5 (10.2) | 2 (4.3) | 1 (3.3) | 0 | 1 (2.0) | 0 | 1 (7.7) |
| Hypertension | 4 (8.2) | 0 | 2 (6.7) | 3 (12.5) | 1 (2.0) | 0 | 0 |
| Gastroesophageal reflux disease | 1 (2.0) | 0 | 4 (13.3) | 2 (8.3) | 1 (2.0) | 0 | 0 |
| Gastroenteritis | 1 (2.0) | 1 (2.1) | 1 (3.3) | 0 | 2 (3.9) | 2 (12.5) | 0 |
| Dizziness | 1 (2.0) | 0 | 3 (10.0) | 0 | 2 (3.9) | 1 (6.3) | 0 |
| Anemia | 1 (2.0) | 0 | 3 (10.0) | 1 (4.2) | 0 | 1 (6.3) | 0 |
| Blood cortisol decreased | 0 | 2 (4.3) | 1 (3.3) | 0 | 0 | 0 | 2 (15.4) |
| Dyspepsia | 1 (2.0) | 0 | 1 (3.3) | 0 | 0 | 2 (12.5) | 0 |

Values are n (%) of subjects with all-causality AEs or n = number of subjects treated.
*Investigator-determined treatment relatedness;
†Only those AEs occurring in ≥~10% of subjects in any treatment group among subjects with an LDL-C ≤25 mg/dL are shown;
‡Only those AEs occurring in ≥~10% of subjects in any treatment group among subjects without an LDL-C ≤25 mg/dL are shown.

Positive ADA titers were found in 18 of 251 L1L3-treated subjects (7.2%), with one 150-mg Q14d L1L3-treated subject exhibiting reduced LDL-C lowering (0.4% of L1L3-treated subjects). In this subject, ADAs were detected on day 113 and, subsequently, LDL-C levels increased towards baseline. Otherwise, little variation was found in LDL-C response between subjects with and without ADAs. The AEs reported in subjects with ADAs were similar to those observed in subjects without ADAs, with no signs or symptoms of hypersensitivity associated with positive ADA titers.

The incidence of creatine kinase abnormalities (>2× the upper limit of normal [ULN]) was similar across placebo (12.0-14.6%) and L1L3 (5.9-14.3%) groups, and no subjects had elevated alanine aminotransferase or aspartate aminotransferase levels>3×ULN.

Discussions

In this phase 2b dose-ranging study of subjects with hypercholesterolemia on stable doses of statin, L1L3 significantly reduced LDL-C across all doses. This is despite protocol-stipulated dose reductions in a large proportion of subjects. L1L3 Q14d and Q28d dosing regimens produced placebo-adjusted reductions in LDL-C at week 12 of up to 53.4 mg/dL for the 150-mg Q14d dose and 44.9 mg/dL for the 300-mg Q28d dose.

L1L3 doses of up to 150-mg Q14d and 300-mg Q28d were generally well tolerated, with a similar incidence of AEs or SAEs across placebo- and L1L3-treatment groups, and few subjects discontinued treatment due to treatment-related AEs. Importantly, the incidence and type of AEs were similar among subjects in whom LDL-C levels fell to ≤25 mg/dL and those in whom LDL-C remained >25 mg/dL. Positive ADA titers were detected in ~7% of L1L3-treated subjects, with LDL-C lowering reduced in one of these subjects (0.4% of L1L3-treated subjects). The impact of ADAs on the efficacy and safety of the PCSK9 inhibitor class will be assessed in longer-term phase 3 trials.

In this study, two subjects receiving L1L3 experienced a non-serious AE of memory loss; however, these subjects were both receiving concomitant medications previously associated with memory loss.

The advent of PCSK9 inhibitors has meant that LDL-C levels of ≤25 mg/dL, and even <10 mg/dL, can be achieved within a few weeks of the first dose. Owing to the limited data available on the physiological effects of very low levels of LDL-C, a unique aspect of this study was the protocol-stipulated L1L3 dose reductions in subjects where LDL-C levels fell to ≤25 mg/dL on two consecutive visits in the first instance, or on any visit thereafter, to prevent persistent LDL-C values≤25 mg/dL. Up to 44.0% of subjects receiving higher doses of L1L3 had dose reductions due to LDL-C levels≤25 mg/dL, indicating that some subjects who showed the greatest response to L1L3 had their dose reduced, thus tempering individual LDL-C responses and the overall group mean LDL-C reductions observed at week 12. Reductions in LDL-C were greater before dose reduction, with maximal placebo-adjusted reductions of −59.9 mg/dL and −66.9 mg/dL for the 100-mg and 150-mg Q14d dose groups recorded at weeks 6 and 8, respectively, which were ~13-15 mg/dL greater than those at week 12. In the 200-mg and 300-mg Q28d dose groups, maximal placebo-adjusted LDL-C reductions of −30.9 mg/dL and −54.9 mg/dL, respectively, were recorded at week 4, which were ~3 mg/dL and ~10 mg/dL greater than the values for week 12. However, factors other than dose reduction, such as missed doses of study medication, may have had an effect on the outcomes of this study. A population PK/PD model was used to predict the expected LDL-C response assuming no dose reductions or missed doses. This analysis suggested that LDL-C would have been lowered at week 12 by up to −36.4 mg/dL to −72.2 mg/dL (an additional ~2-19 mg/dL) with L1L3 Q14d, and by −40.4 mg/dL to −55.4 mg/dL (an additional ~11-13 mg/dL) with L1L3 Q28d, in the absence of dose reductions or missed doses.

For LDL-C, an analysis of the Treating to New Targets trial demonstrated that visit-to-visit variability in LDL-C was an independent predictor of cardiovascular risk (see, e.g., Bangalore et al., Eur. Heart J. 33 (Suppl 1):958 Abstract 5243, 2012). Each 1-SD increase in LDL-C variability, measured as the average absolute difference between successive values, increased the risk of any coronary event by 16% and any cardiovascular event by 11%, independent of statin dose and achieved LDL-C (Bangalore et al., supra). This is a consideration with the dosing of PCSK9 mAbs, where high-dose monthly regimens can produce substantial fluctuations in LDL-C levels between doses, leading to large visit-to-visit LDL-C variability, as confirmed in this study. The magnitude of LDL-C reductions from baseline achieved with L1L3—up to −60% with 150-mg Q14d and up to ~74% at the nadir with 300-mg Q28d—was comparable to that reported for other PCSK9 inhibitors currently in clinical development (see, e.g., Giugliano et al., Lancet, 380:2007-2017, 2012); Koren et al., Lancet, 380:1995-2006, 2012; McKenney et al., J. Am. Coll. Cardiol., 59:2344-2353, 2012; Stein et al., Lancet, 380:29-36, 2012; Koren et al., J. am. Coll. Cardiol. Doi: 10.1016/j.jacc.2014.03.018, 2014; and Stroes et al., J. Am. Coll. Cardiol. Doi:10.1016/j.jacc.2014.03.019, 2014). Although greater maximal reductions in LDL-C were seen with higher doses of L1L3 administered Q28d, these reductions were not as well maintained between doses. Following the sharp decrease in LDL-C levels 2 weeks after administration of each Q28d L1L3 dose, LDL-C levels gradually increased in the 2 weeks post-nadir, resulting in a "saw-tooth" pattern (FIG. 5B) that has also been observed with monthly dosing of evolocumab (see, Giugliano et al., supra; and Koren et al., supra) and alirocumab (e.g., McKenney et al., supra; and Stein et al., supra). Lower doses of L1L3 administered Q14d eliminated the cycle of LDL-C fluctuation seen with monthly dosing while still resulting in significant LDL-C reductions (FIG. 5A). Given the potential for PCSK9 inhibition to produce rapid and marked reductions in LDL-C, a lower L1L3 dose administered more frequently may also help circumvent potential safety concerns associated with the very low levels of LDL-C observed following monthly high-dose treatment. In this current study, LDL-C levels at week 2 were reduced by ~70% from baseline with high-dose Q28d L1L3 therapy, with LDL-C values falling to ≤25 mg/dL in ~40% of subjects in the 2 weeks following the first dose. Together, these observations support a Q14d rather than a Q28d L1L3 dosing regimen for phase 3 studies.

The achievement of substantial reductions in LDL-C levels following PCSK9 inhibition is likely to be of clinical benefit, particularly in patients at high cardiovascular risk who continue to have elevated LDL-C on maximally tolerated statin therapy. However, there are challenges associated with the use of a new therapy, such as PCSK9 inhibitors, that can lead to very low levels of LDL-C. First is a reliable method for measuring and reporting very low LDL-C values by clinical laboratories. Although the Friedewald equation has been routinely used to calculate LDL-C for over 40 years, it can underestimate low levels of LDL-C when compared with direct measurement following ultracentrifugation (used in this study for LDL-C levels 25 mg/dL) (see, e.g., Friedwald et al., Clin. Chem. 18:499-502 (1972); and Scharnagl et al., Clin. Chem. Lab. Med. 39:426-431 (2001)). Newer, more accurate methods for calculation of LDL-C from a standard lipid profile have been proposed, most recently by Martin et al. (JAMA, 310:2061-2068 (2013). External validation of this new method may provide clinicians with a reliable and inexpensive method to assess LDL-C at the very low levels likely to be achieved with PCSK9 inhibition.

Significant, rapid reductions in LDL-C levels with PCSK9 inhibitors will also present physicians with a choice between starting with a low dose and up-titration if necessary, or starting with high doses and subsequent dose reduction if required, or ignoring LDL-C levels after initiation of therapy. Intensive initial therapy is often preferred to reduce cardiovascular outcomes, particularly in high-risk patients, and provides an argument for high initial doses. The LDL-C level at which dose reduction is triggered is crucial to attain maximal clinical benefit. This study employed a threshold LDL-C of ≤25 mg/dL for dose reduction; however, LDL-C values≤25 mg/dL were frequently achieved, and dose reduction occurred frequently and limited efficacy. LDL-C levels of ≤25 mg/dl were not associated with harm in this study and do not appear to be associated with harm in trials of other PCSK9 inhibitors conducted to date. Hence, further lowering the LDL-C threshold at which dose reduction is initiated (e.g., lowered to 0 mg/dL) is supported.

The L1L3 phase 3 SPIRE (Studies in PCSK9 Inhibition and Reduction in Events) program consists of additional trials assessing the lipid-lowering efficacy of L1L3 and two cardiovascular outcome studies. SPIRE-1 assesses whether lowering LDL-C to levels well below previously recommended targets lead to further reduction in cardiovascular events. This study includes high-risk patients with baseline LDL-C levels≥70 to <100 mg/dL. SPIRE-2 evaluates the efficacy and safety of L1L3 in a range of high-risk patients who have not achieved LDL-C levels<100 mg/dL despite high-dose statin therapy or who are partially or completely statin intolerant.

Conclusions

L1L3 150-mg Q14d significantly reduced LDL-C by 53.4 mg/dL versus placebo at week 12, inclusive of protocol-directed dose reductions at week 10 in 32.5% of these subjects. PK/PD modeling and simulation predicted greater reductions in LDL-C in the absence of L1L3 dose reductions.

Example 2—Phase 3 Randomized, Placebo-Controlled, Dose-Ranging Efficacy and Safety Study of L1L3 in Subjects with Primary Hyperlipidemia or Mixed Dyslipidemia at High or Very High Risk for CV Events This study is a Phase 3, double blind, placebo controlled, randomized, stratified, parallel group, multi-center clinical trial designed to compare the efficacy and safety of L1L3 150 mg subcutaneous Q2wks to placebo for LDL-C lowering in subjects with primary hyperlipidemia or mixed dyslipidemia at high or very high risk for CV events receiving a maximally tolerated dose of statin therapy and whose LDL-C is greater than or equal to 70 mg/dL (1.81 mmol/L). The study enrolls approximately 300 subjects in each of the 2 treatment arms, for a total of approximately 600 subjects randomized at approximately 100 sites, who receives study drug for 12 months.

Subjects are stratified based on pre-randomization TG (triglycerides) level (<200 mg/dL [2.26 mmol/L] or ≥200 mg/dL [2.26 mmol/L]) and geographic region, and then randomized within each stratum to receive either 150 mg Q2wks of L1L3 or placebo in a 1:1 ratio. Lipid levels are blinded to the investigator and staff, subject and sponsor. Dose modifications triggered by LDL-C levels≤10 mg/dL or 0.26 mmol/L are conducted through the Interactive Response Technologies (IRT) system to preserve study blind.

Study Treatments

Subjects are randomized to L1L3 150 mg or placebo Q2wks in a 1:1 ratio. Subjects self-inject, or if unable to self-inject, have study drug administered by a family member, health care assistant, or health care provider.

The dose selected for this study is a starting dose of 150 mg administered subcutaneously (SC), every 2 weeks (Q2wks), with a modification to a dose of 75 mg Q2wks for subjects with two consecutive low LDL-C concentrations (≤10 mg/dL or 0.26 mmol/L) at the end of the dosing interval. Additionally, subjects with two consecutive low LDL-C concentrations≤10 mg/dL (0.26 mmol/L), even after a dose reduction, have their dose frequency modified to 75 mg SC every 4 weeks (Q4wks). Based on population PK/PD modeling, a dose of 150 mg Q2wks is estimated to be equivalent to approximately 80% of the maximal response (ED80) of the dose response for LDL-C lowering (−67% CFB), and is a dose where the percentage of subjects with LDL-C≤10 mg/dL at the end of a dosing interval is approximately 8%.

Example 3—Further Study of Results from the Randomized, Placebo-Controlled, Dose-Ranging Study of L1L3 in Statin-Treated Subjects with Hypercholesterolemia Further results from the phase 2 study described in Example 1 were reviewed (Tables 6 and 7). A review of eye disorders in the shows a higher incidence in those subjects who received study drug compared to placebo in the 50 mg, 100 mg and 150 mg Q14 Day dosing regimen and a higher incidence in the 200 mg Q28 Day dosing regimen when compared to placebo, but not in the 300 mg Q28 Day dosing regimen. The individual Preferred Terms (PTs) occurred in 1 subject with the exception of conjunctivitis in 2 subjects in 100 mg Q14 Day dosing regimen and glaucoma in 2 subjects in the 200 mg Q28 Day Dosing regimen and conjunctivitis.

TABLE 6

Number (%) of Subjects Reporting Treatment Emergent Adverse Events (TEAEs) - Q14d Safety Analysis Set

|  | Placebo, Q14d (N = 49) | 50 mg, Q14d (N = 50) | 100 mg, Q14d (N = 51) | 150 mg, Q14d (N = 49) |
|---|---|---|---|---|
| Eye disorders | 1 (2.0) | 2 (4.0) | 4 (7.8) | 3 (6.1) |
| Cataract | 0 (0.0) | 1 (2.0) | 0 (0.0) | 0 (0.0) |
| Conjunctivitis | 0 (0.0) | 0 (0.0) | 2 (3.9) | 0 (0.0) |
| Dry eye | 0 (0.0) | 0 (0.0) | 1 (2.0) | 0 (0.0) |
| Eye hemorrhage | 0 (0.0) | 1 (2.0) | 0 (0.0) | 0 (0.0) |
| Eye pruritus | 0 (0.0) | 0 (0.0) | 0 (0.0) | 1 (2.0) |
| Eyelid pain | 0 (0.0) | 0 (0.0) | 1 (2.0) | 0 (0.0) |

Note:
Classifications of adverse events are based on the medical Dictionary for Regulatory Activities (MedDRA) Version 16.0.
a. Totals for the number of subjects at a higher level are not necessarily the sum of those at the lower levels since a subject may report two or more different adverse events within the higher level category.

TABLE 7

Number (%) of Subjects Reporting Treatment Emergent Adverse Events (TEAEs) - Q28d Safety Analysis Set

|  | Placebo, Q14d (N = 51) | 200 mg, Q28d (N = 50) | 300 mg, Q28d (N = 50) |
|---|---|---|---|
| Eye disorders | 1 (2.0) | 6 (12.0) | 1 (2.0) |
| Blepharitis | 0 (0.0) | 0 (0.0) | 1 (2.0) |
| Cataract | 0 (0.0) | 1 (2.0) | 0 (0.0) |
| Conjunctivitis | 1 (2.0) | 1 (2.0) | 0 (0.0) |
| Corneal erosion | 0 (0.0) | 1 (2.0) | 0 (0.0) |
| Glaucoma | 0 (0.0) | 2 (4.0) | 0 (0.0) |

TABLE 7-continued

Number (%) of Subjects Reporting Treatment Emergent Adverse Events (TEAEs) - Q28d Safety Analysis Set

| | Placebo, Q14d (N = 51) | 200 mg, Q28d (N = 50) | 300 mg, Q28d (N = 50) |
|---|---|---|---|
| Ocular hyperaemia | 0 (0.0) | 1 (2.0) | 0 (0.0) |
| Vitreous floaters | 0 (0.0) | 1 (2.0) | 0 (0.0) |

Note:
Classifications of adverse events are based on the medical Dictionary for Regulatory Activities (MedDRA) Version 16.0.
a. Totals for the number of subjects at a higher level are not necessarily the sum of those at the lower levels since a subject may report two or more different adverse events within the higher level category.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. A method for treating a patient diagnosed with a disorder characterized by an elevated low-density lipoprotein cholesterol (LDL-C) level in the blood, comprising delivering to the patient as a single administration or plurality of administrations an initial dose of at least about 100 mg of a proprotein convertase subtilisin kexin type 9 (PCSK9) antagonist antibody, and delivering to the patient a single administration or plurality of administrations at a subsequent dose that is about the same as the initial dose, or at least half the initial dose after the patient has a LDL-C level at or below about 25, 20, 15 or 10 mg/dL, wherein all administrations are separated in time from each other by at least about two weeks.

2. The method of claim 1, wherein the subsequent dose is about two thirds of the initial dose.

3. The method of claim 1, wherein the subsequent dose is about one half the initial dose.

4. The method of claim 1, wherein the initial dose is 150 mg, and the subsequent dose is reduced below 150 mg every two weeks after the patient has a LDL-C level below about 25, 20, 15 or 10 mg/dL.

5. The method of claim 4, wherein the subsequent dose is reduced to 75 mg after the patient has a LDL-C at or below about 25, 20, 15 or 10 mg/dL.

6. The method of claim 4, wherein the subsequent dose is 100 mg after the patient has a LDL-C at or below about 25, 20, 15 or 10 mg/dL.

7. The method of claim 1, wherein the subsequent dose is administered to the patient after the patient has at least about two consecutive assessments of LDL-C at or below about 25, 20, 15 or 10 mg/dL.

8. The method of claim 3, wherein said subsequent dose is reduced to half the initial dose and is administered every two weeks after the patient has a LDL-C at or below 25, 20, 15 or 10 mg/dL, and wherein a second subsequent dose is administered every two weeks and is even further reduced to one third or one quarter the initial dose, delivered as a single or plurality of administrations, after the patient has a LDL-C again at or below about 25, 20, 15 or 10 mg/dL while on the subsequent dose.

9. The method of claim 2, wherein said subsequent dose is reduced to two thirds the initial dose and is administered every two weeks after the patient has a LDL-C at or below 25, 20, 15 or 10 mg/dL, and wherein a second subsequent dose is administered every two weeks and is then even further reduced to one third or one quarter the initial dose, delivered as a single or plurality of administrations, after the patient had a LDL-C again at or below about 25, 20, 15 or 10 mg/dL while on the subsequent dose.

10. The method of claim 1, wherein said subsequent dose is reduced to half the initial dose and is administered every two weeks after the patient has at least about two consecutive assessments of LDL-C level at or below 25, 20, 15 or 10 mg/dL, and said subsequent dose is then administered every four weeks after the patient has at least about another two consecutive assessments of LDL-C level again at or below 25, 20, 15 or 10 mg/dL while on the subsequent dose every two weeks.

11. The method of claim 1, wherein said subsequent dose is reduced to half the initial dose and is administered every two weeks after the patient has a LDL-C level at or below 25, 20, 15 or 10 mg/dL, and said subsequent dose is then administered every four weeks after the patient has a LDL-C level again at or below 25, 20, 15 or 10 mg/dL while on the subsequent dose every two weeks.

12. The method of claim 11, wherein the initial dose is 150 mg and the subsequent dose is 75 mg.

13. The method of claim 1, wherein a statin has been administered prior to the initial dose of the PCSK9 antagonist antibody.

14. The method of claim 13, wherein the statin is atorvastatin, cerivastatin, fluvastatin, lovastatin, mevastatin, pitavastatin, pravastatin, rosuvastatin, simvastatin, or any pharmaceutically acceptable salts, or stereoisomers, thereof.

15. The method of claim 1, wherein the disorder is dyslipidemia, hyperlipidemia, hypercholesterolemia, atherosclerosis, cardiovascular disease, and/or coronary heart disease.

16. The method of claim 1, wherein the antibody blocks LDLR binding to the PCSK9 of SEQ ID NO: 1.

17. The method of claim 1, wherein the antibody is alirocumab, evolocumab, REGN728, LGT209, RG7652, LY3015014, J16, L1L3 (bococizumab), 31H4, 11F1, 12H11, 8A1, 8A3, 3C4, 300N, or 1D05.

18. The method of claim 1, wherein the antibody comprises a VH CDR1 having the amino acid sequence shown in SEQ ID NO: 4, 5, or 6, a VH CDR2 having the amino acid sequence shown in SEQ ID NO:7 or 8, a VH CDR3 having the amino acid sequence shown in SEQ ID NO: 9; and a VL CDR1 having the amino acid sequence shown in SEQ ID NO:10, a VL CDR2 having the amino acid sequence shown in SEQ ID NO:11, and a VL CDR3 having the amino acid sequence shown in SEQ ID NO: 12.

19. The method of claim 1, wherein the LDL-C level is at least about or lower than 65, 60, 55, 45, 40, 35, 30, 25, 20, or 15 mg/dL after administration of the initial dose or both the initial dose and the subsequent dose.

* * * * *

```
                       SEQUENCE LISTING

<160> NUMBER OF SEQ ID NOS: 36

<210> SEQ ID NO 1
<211> LENGTH: 692
<212> TYPE: PRT
<213> ORGANISM: Homo sapiens

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220
```

```
Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Leu Leu Pro
            275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
                435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys His Ala Pro Gly Leu Glu Cys
            595                 600                 605

Lys Val Lys Glu His Gly Ile Pro Ala Pro Gln Glu Gln Val Thr Val
            610                 615                 620

Ala Cys Glu Glu Gly Trp Thr Leu Thr Gly Cys Ser Ala Leu Pro Gly
625                 630                 635                 640
```

```
Thr Ser His Val Leu Gly Ala Tyr Ala Val Asp Asn Thr Cys Val Val
            645                 650                 655

Arg Ser Arg Asp Val Ser Thr Thr Gly Ser Thr Ser Glu Gly Ala Val
        660                 665                 670

Thr Ala Val Ala Ile Cys Cys Arg Ser Arg His Leu Ala Gln Ala Ser
        675                 680                 685

Gln Glu Leu Gln
        690

<210> SEQ ID NO 2
<211> LENGTH: 118
<212> TYPE: PRT
<213> ORGANISM: Artificial
<220> FEATURE:
<223> OTHER INFORMATION: Synthetic Construct

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Glu Ile Ser Pro Phe Gly Gly Arg Thr Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
                100                 105                 110

Thr Val Thr Val Ser Ser
            115

<210> SEQ ID NO 3
<211> LENGTH: 107
<212> TYPE: PRT
<213> ORGANISM: Artificial
<220> FEATURE:
<223> OTHER INFORMATION: Synthetic Construct

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
                100                 105

<210> SEQ ID NO 4
```

```
<211> LENGTH: 5
<212> TYPE: PRT
<213> ORGANISM: Artificial
<220> FEATURE:
<223> OTHER INFORMATION: Synthetic Construct

<400> SEQUENCE: 4

Ser Tyr Tyr Met His
1               5

<210> SEQ ID NO 5
<211> LENGTH: 7
<212> TYPE: PRT
<213> ORGANISM: Artificial
<220> FEATURE:
<223> OTHER INFORMATION: Synthetic Construct

<400> SEQUENCE: 5

Gly Tyr Thr Phe Thr Ser Tyr
1               5

<210> SEQ ID NO 6
<211> LENGTH: 10
<212> TYPE: PRT
<213> ORGANISM: Artificial
<220> FEATURE:
<223> OTHER INFORMATION: Synthetic Construct

<400> SEQUENCE: 6

Gly Tyr Thr Phe Thr Ser Tyr Tyr Met His
1               5                   10

<210> SEQ ID NO 7
<211> LENGTH: 17
<212> TYPE: PRT
<213> ORGANISM: Artificial
<220> FEATURE:
<223> OTHER INFORMATION: Synthetic Construct

<400> SEQUENCE: 7

Glu Ile Ser Pro Phe Gly Gly Arg Thr Asn Tyr Asn Glu Lys Phe Lys
1               5                   10                  15

Ser

<210> SEQ ID NO 8
<211> LENGTH: 6
<212> TYPE: PRT
<213> ORGANISM: Artificial
<220> FEATURE:
<223> OTHER INFORMATION: Synthetic Construct

<400> SEQUENCE: 8

Ser Pro Phe Gly Gly Arg
1               5

<210> SEQ ID NO 9
<211> LENGTH: 9
<212> TYPE: PRT
<213> ORGANISM: Artificial
<220> FEATURE:
<223> OTHER INFORMATION: Synthetic Construct

<400> SEQUENCE: 9

Glu Arg Pro Leu Tyr Ala Ser Asp Leu
1               5
```

```
<210> SEQ ID NO 10
<211> LENGTH: 11
<212> TYPE: PRT
<213> ORGANISM: Artificial
<220> FEATURE:
<223> OTHER INFORMATION: Synthetic Construct

<400> SEQUENCE: 10

Arg Ala Ser Gln Gly Ile Ser Ser Ala Leu Ala
1               5                   10

<210> SEQ ID NO 11
<211> LENGTH: 7
<212> TYPE: PRT
<213> ORGANISM: Artificial
<220> FEATURE:
<223> OTHER INFORMATION: Synthetic Construct

<400> SEQUENCE: 11

Ser Ala Ser Tyr Arg Tyr Thr
1               5

<210> SEQ ID NO 12
<211> LENGTH: 9
<212> TYPE: PRT
<213> ORGANISM: Artificial
<220> FEATURE:
<223> OTHER INFORMATION: Synthetic Construct

<400> SEQUENCE: 12

Gln Gln Arg Tyr Ser Leu Trp Arg Thr
1               5

<210> SEQ ID NO 13
<211> LENGTH: 214
<212> TYPE: PRT
<213> ORGANISM: Artificial
<220> FEATURE:
<223> OTHER INFORMATION: Synthetic Construct

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
            165                 170                 175
Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 444
<212> TYPE: PRT
<213> ORGANISM: Artificial
<220> FEATURE:
<223> OTHER INFORMATION: Synthetic Construct

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Phe Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
```

```
             305                 310                 315                 320
Ser Asn Lys Gly Leu Pro Ser Ser Ile Glu Lys Thr Ile Ser Lys Thr
                    325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 15
<211> LENGTH: 40
<212> TYPE: PRT
<213> ORGANISM: Homo sapiens

<400> SEQUENCE: 15

```
Gly Thr Asn Glu Cys Leu Asp Asn Asn Gly Gly Cys Ser His Val Cys
1               5                   10                  15

Asn Asp Leu Lys Ile Gly Tyr Glu Cys Leu Cys Pro Asp Gly Phe Gln
                20                  25                  30

Leu Val Ala Gln Arg Arg Cys Glu
            35                  40
```

<210> SEQ ID NO 16
<211> LENGTH: 860
<212> TYPE: PRT
<213> ORGANISM: Homo sapiens

<400> SEQUENCE: 16

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
                20                  25                  30

Gln Cys Gln Asp Gly Lys Cys Ile Ser Tyr Lys Trp Val Cys Asp Gly
            35                  40                  45

Ser Ala Glu Cys Gln Asp Gly Ser Asp Glu Ser Gln Glu Thr Cys Leu
        50                  55                  60

Ser Val Thr Cys Lys Ser Gly Asp Phe Ser Cys Gly Gly Arg Val Asn
65              70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
```

```
           145                 150                 155                 160
    Ile Pro Gln Leu Trp Ala Cys Asp Asn Asp Pro Asp Cys Glu Asp Gly
                       165                 170                 175
    Ser Asp Glu Trp Pro Gln Arg Cys Arg Gly Leu Tyr Val Phe Gln Gly
                       180                 185                 190
    Asp Ser Ser Pro Cys Ser Ala Phe Glu Phe His Cys Leu Ser Gly Glu
                       195                 200                 205
    Cys Ile His Ser Ser Trp Arg Cys Asp Gly Pro Asp Cys Lys Asp
                       210                 215                 220
    Lys Ser Asp Glu Glu Asn Cys Ala Val Ala Thr Cys Arg Pro Asp Glu
    225                 230                 235                 240
    Phe Gln Cys Ser Asp Gly Asn Cys Ile His Gly Ser Arg Gln Cys Asp
                       245                 250                 255
    Arg Glu Tyr Asp Cys Lys Asp Met Ser Asp Glu Val Gly Cys Val Asn
                       260                 265                 270
    Val Thr Leu Cys Glu Gly Pro Asn Lys Phe Lys Cys His Ser Gly Glu
                       275                 280                 285
    Cys Ile Thr Leu Asp Lys Val Cys Asn Met Ala Arg Asp Cys Arg Asp
                       290                 295                 300
    Trp Ser Asp Glu Pro Ile Lys Glu Cys Gly Thr Asn Glu Cys Leu Asp
    305                 310                 315                 320
    Asn Asn Gly Gly Cys Ser His Val Cys Asn Asp Leu Lys Ile Gly Tyr
                       325                 330                 335
    Glu Cys Leu Cys Pro Asp Gly Phe Gln Leu Val Ala Gln Arg Arg Cys
                       340                 345                 350
    Glu Asp Ile Asp Glu Cys Gln Asp Pro Asp Thr Cys Ser Gln Leu Cys
                       355                 360                 365
    Val Asn Leu Glu Gly Gly Tyr Lys Cys Gln Cys Glu Glu Gly Phe Gln
                       370                 375                 380
    Leu Asp Pro His Thr Lys Ala Cys Lys Ala Val Gly Ser Ile Ala Tyr
    385                 390                 395                 400
    Leu Phe Phe Thr Asn Arg His Glu Val Arg Lys Met Thr Leu Asp Arg
                       405                 410                 415
    Ser Glu Tyr Thr Ser Leu Ile Pro Asn Leu Arg Asn Val Val Ala Leu
                       420                 425                 430
    Asp Thr Glu Val Ala Ser Asn Arg Ile Tyr Trp Ser Asp Leu Ser Gln
                       435                 440                 445
    Arg Met Ile Cys Ser Thr Gln Leu Asp Arg Ala His Gly Val Ser Ser
    450                 455                 460
    Tyr Asp Thr Val Ile Ser Arg Asp Ile Gln Ala Pro Asp Gly Leu Ala
    465                 470                 475                 480
    Val Asp Trp Ile His Ser Asn Ile Tyr Trp Thr Asp Ser Val Leu Gly
                       485                 490                 495
    Thr Val Ser Val Ala Asp Thr Lys Gly Val Lys Arg Lys Thr Leu Phe
                       500                 505                 510
    Arg Glu Asn Gly Ser Lys Pro Arg Ala Ile Val Val Asp Pro Val His
                       515                 520                 525
    Gly Phe Met Tyr Trp Thr Asp Trp Gly Thr Pro Ala Lys Ile Lys Lys
                       530                 535                 540
    Gly Gly Leu Asn Gly Val Asp Ile Tyr Ser Leu Val Thr Glu Asn Ile
    545                 550                 555                 560
    Gln Trp Pro Asn Gly Ile Thr Leu Asp Leu Leu Ser Gly Arg Leu Tyr
                       565                 570                 575
```

Trp Val Asp Ser Lys Leu His Ser Ile Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 17
<211> LENGTH: 441
<212> TYPE: PRT
<213> ORGANISM: Artificial
<220> FEATURE:
<223> OTHER INFORMATION: Synthetic Construct

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                 85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 18
<211> LENGTH: 215
<212> TYPE: PRT
<213> ORGANISM: Artificial
<220> FEATURE:
<223> OTHER INFORMATION: Synthetic Construct

<400> SEQUENCE: 18

```
Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 19
<211> LENGTH: 115
<212> TYPE: PRT
<213> ORGANISM: Artificial
<220> FEATURE:
<223> OTHER INFORMATION: Synthetic Construct

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65              70                  75                  80

Met Glu Leu Arg Ser Leu Arg Ser Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 20
```

```
<211> LENGTH: 112
<212> TYPE: PRT
<213> ORGANISM: Artificial
<220> FEATURE:
<223> OTHER INFORMATION: Synthetic Construct

<400> SEQUENCE: 20

Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu Gly Gln Pro
            100                 105                 110

<210> SEQ ID NO 21
<211> LENGTH: 10
<212> TYPE: PRT
<213> ORGANISM: Artificial
<220> FEATURE:
<223> OTHER INFORMATION: Synthetic Construct

<400> SEQUENCE: 21

Gly Tyr Thr Leu Thr Ser Tyr Gly Ile Ser
1               5                   10

<210> SEQ ID NO 22
<211> LENGTH: 12
<212> TYPE: PRT
<213> ORGANISM: Artificial
<220> FEATURE:
<223> OTHER INFORMATION: Synthetic Construct

<400> SEQUENCE: 22

Val Ser Phe Tyr Asn Gly Asn Thr Asn Tyr Ala Gln
1               5                   10

<210> SEQ ID NO 23
<211> LENGTH: 9
<212> TYPE: PRT
<213> ORGANISM: Artificial
<220> FEATURE:
<223> OTHER INFORMATION: Synthetic Construct

<400> SEQUENCE: 23

Cys Ala Arg Gly Tyr Gly Met Asp Val
1               5

<210> SEQ ID NO 24
<211> LENGTH: 14
<212> TYPE: PRT
<213> ORGANISM: Artificial
<220> FEATURE:
<223> OTHER INFORMATION: Synthetic Construct

<400> SEQUENCE: 24

Thr Gly Thr Ser Ser Asp Val Gly Gly Tyr Asn Ser Val Ser
```

<210> SEQ ID NO 25
<211> LENGTH: 9
<212> TYPE: PRT
<213> ORGANISM: Artificial
<220> FEATURE:
<223> OTHER INFORMATION: Synthetic Construct

<400> SEQUENCE: 25

Asn Ser Tyr Thr Ser Thr Ser Met Val
1               5

<210> SEQ ID NO 26
<211> LENGTH: 7
<212> TYPE: PRT
<213> ORGANISM: Artificial
<220> FEATURE:
<223> OTHER INFORMATION: Synthetic Construct

<400> SEQUENCE: 26

Glu Val Ser Asn Arg Pro Ser
1               5

<210> SEQ ID NO 27
<211> LENGTH: 447
<212> TYPE: PRT
<213> ORGANISM: Artificial
<220> FEATURE:
<223> OTHER INFORMATION: Synethetic Construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 28
<211> LENGTH: 220
<212> TYPE: PRT
<213> ORGANISM: Artificial
<220> FEATURE:
<223> OTHER INFORMATION: Synthetic Construct

<400> SEQUENCE: 28

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 29
<211> LENGTH: 118
<212> TYPE: PRT
<213> ORGANISM: Artificial
<220> FEATURE:
<223> OTHER INFORMATION: Synthetic Construct

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser
        115

<210> SEQ ID NO 30
<211> LENGTH: 115
<212> TYPE: PRT
<213> ORGANISM: Artificial
<220> FEATURE:
<223> OTHER INFORMATION: Synthetic Construct

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile

```
                    100                 105                 110
Lys Arg Thr
        115

<210> SEQ ID NO 31
<211> LENGTH: 10
<212> TYPE: PRT
<213> ORGANISM: Artificial
<220> FEATURE:
<223> OTHER INFORMATION: Synthetic Construct

<400> SEQUENCE: 31

Gly Phe Thr Phe Asn Asn Tyr Ala Met Asn
1               5                   10

<210> SEQ ID NO 32
<211> LENGTH: 16
<212> TYPE: PRT
<213> ORGANISM: Artificial
<220> FEATURE:
<223> OTHER INFORMATION: Synthetic Construct

<400> SEQUENCE: 32

Ile Ser Gly Ser Gly Gly Thr Thr Asn Tyr Ala Asp Ser Val Lys Gly
1               5                   10                  15

<210> SEQ ID NO 33
<211> LENGTH: 9
<212> TYPE: PRT
<213> ORGANISM: Artificial
<220> FEATURE:
<223> OTHER INFORMATION: Synthetic Construct

<400> SEQUENCE: 33

Asp Ser Asn Trp Gly Asn Phe Asp Leu
1               5

<210> SEQ ID NO 34
<211> LENGTH: 17
<212> TYPE: PRT
<213> ORGANISM: Artificial
<220> FEATURE:
<223> OTHER INFORMATION: Synthetic Construct

<400> SEQUENCE: 34

Lys Ser Ser Gln Ser Val Leu Tyr Arg Ser Asn Asn Arg Asn Phe Leu
1               5                   10                  15

Gly

<210> SEQ ID NO 35
<211> LENGTH: 7
<212> TYPE: PRT
<213> ORGANISM: Artificial
<220> FEATURE:
<223> OTHER INFORMATION: Synthetic Construct

<400> SEQUENCE: 35

Trp Ala Ser Thr Arg Glu Ser
1               5

<210> SEQ ID NO 36
<211> LENGTH: 9
<212> TYPE: PRT
<213> ORGANISM: Artificial
<220> FEATURE:
<223> OTHER INFORMATION: Synthetic Construct
```

```
<400> SEQUENCE: 36

Gln Tyr Tyr Thr Thr Pro Tyr Thr Phe
1               5
```